US008415293B2

(12) United States Patent
Bielicki et al.

(10) Patent No.: US 8,415,293 B2
(45) Date of Patent: Apr. 9, 2013

(54) PEPTIDE MEDIATORS OF CHOLESTEROL EFFLUX

(75) Inventors: John K. Bielicki, San Ramon, CA (US); Jan Johansson, Portola Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/999,966

(22) PCT Filed: Jun. 17, 2009

(86) PCT No.: PCT/US2009/047694
§ 371 (c)(1),
(2), (4) Date: Apr. 13, 2011

(87) PCT Pub. No.: WO2009/155366
PCT Pub. Date: Dec. 23, 2009

(65) Prior Publication Data
US 2011/0190196 A1    Aug. 4, 2011

Related U.S. Application Data

(60) Provisional application No. 61/073,708, filed on Jun. 18, 2008.

(51) Int. Cl.
*A61K 38/10* (2006.01)
*A61P 9/10* (2006.01)

(52) U.S. Cl.
USPC ............................ 514/1.9; 514/21.4; 530/326

(58) Field of Classification Search .................... 530/324
See application file for complete search history.

(56) References Cited

FOREIGN PATENT DOCUMENTS
WO    WO 2005/058938 A2    6/2005
WO    WO 2008/115303 A2    9/2008

OTHER PUBLICATIONS

Pierce et al., Environ. Microbiol. (2008) 10: 2550-2573.*
International Search Report from PCT/US2009/047694, dated Feb. 2, 2010.
Bielicki et al.; "A Highly Potent ABCA1 Cholesterol Efflux Peptide (ATI-5261) Greatly Reduces Established Altherosclerosis in Hypercholesterolerric Mouse Models"; Abstract #8080503; 6th annual CardiovascularBiomarker and Surrogate Endpoint Symposium "Building a Framework for Biomarker Application" Sep. 10-12, 2008. Retrieved from the Internet Jan. 16, 2010: http://www.cmod.org/2008_Program%20FINAL.pdf/ p. 38 of the pdf.
Vedhachalam et al.; "The C-terminal lipid-binding domain of apoliprotein E is a highly eddicient mediator of ABCA1-dependent cholesterol efflux that promotes the assembly of high-density lipoproteins"; *Biochemistry*: 46:2583-2593 (Mar. 2007) ePub Feb. 17, 2007.
Wang et al.; "Regulation and mechanisms of ATP-binding cassette transporter A1-mediated cellular cholesterol efflux"; *Arterioscler. Thromb. Vasc. Biol.*; 23(7):1178-1184 (Jul. 2003) ePub May 2003.

* cited by examiner

*Primary Examiner* — Karlheinz R Skowronek
*Assistant Examiner* — Catherine Mader
(74) *Attorney, Agent, or Firm* — Kilpatrick Townsend & Stockton LLP

(57) ABSTRACT

The present invention provides a family of non-naturally occurring polypeptides having cholesterol efflux activity that parallels that of full-length apolipoproteins (e.g., Apo AI and Apo E), and having high selectivity for ABAC1 that parallels that of full-length apolipoproteins. The invention also provides compositions comprising such polypeptides, methods of identifying, screening and synthesizing such polypeptides, and methods of treating, preventing or diagnosing diseases and disorders associated with dyslipidemia, hypercholesterolemia and inflammation.

19 Claims, 21 Drawing Sheets

SEQUENCE LISTING

<160> NUMBER OF SEQ ID NOS: 62

<210> SEQ ID NO 1
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity
<220> FEATURE:
<221> NAME/KEY: VARIANT
<222> LOCATION: (1)...(1)
<223> OTHER INFORMATION: Xaa = Glu or Asp
<220> FEATURE:
<221> NAME/KEY: VARIANT
<222> LOCATION: (2)...(2)
<223> OTHER INFORMATION: Xaa = Phe, Leu, Trp, Ile, Val or Ala
<220> FEATURE:
<221> NAME/KEY: VARIANT
<222> LOCATION: (3)...(3)
<223> OTHER INFORMATION: Xaa = Arg, Lys or Cys
<220> FEATURE:
<221> NAME/KEY: VARIANT
<222> LOCATION: (4)...(4)
<223> OTHER INFORMATION: Xaa = Glu, Asp, Ala or Gly
<220> FEATURE:
<221> NAME/KEY: VARIANT
<222> LOCATION: (5)...(5)
<223> OTHER INFORMATION: Xaa = Arg, Lys or Cys
<220> FEATURE:
<221> NAME/KEY: VARIANT
<222> LOCATION: (6)...(6)
<223> OTHER INFORMATION: Xaa = Phe, Leu, Trp, Ile, Val or Ala
<220> FEATURE:
<221> NAME/KEY: VARIANT
<222> LOCATION: (7)...(7)
<223> OTHER INFORMATION: Xaa = Glu or Asp
<220> FEATURE:
<221> NAME/KEY: VARIANT
<222> LOCATION: (8)...(8)
<223> OTHER INFORMATION: Xaa = Ala, Gly or Val
<220> FEATURE:
<221> NAME/KEY: VARIANT
<222> LOCATION: (9)...(10)
<223> OTHER INFORMATION: Xaa = Phe, Leu, Trp, Ile, Val or Ala
<220> FEATURE:
<221> NAME/KEY: VARIANT
<222> LOCATION: (11)...(11)
<223> OTHER INFORMATION: Xaa = Glu, Asp, Ala or Gly
<220> FEATURE:
<221> NAME/KEY: VARIANT
<222> LOCATION: (12)...(13)
<223> OTHER INFORMATION: Xaa = Phe, Leu, Trp, Ile, Val or Ala
<220> FEATURE:
<221> NAME/KEY: VARIANT
<222> LOCATION: (14)...(14)
<223> OTHER INFORMATION: Xaa = Arg, Ala, Glu or Cys
<220> FEATURE:
<221> NAME/KEY: VARIANT
<222> LOCATION: (15)...(15)
<223> OTHER INFORMATION: Xaa = Glu or Asp
<220> FEATURE:
<221> NAME/KEY: VARIANT
<222> LOCATION: (16)...(17)
<223> OTHER INFORMATION: Xaa = Phe, Leu, Trp, Ile, Val or Ala
<220> FEATURE:
<221> NAME/KEY: VARIANT
<222> LOCATION: (18)...(18)
<223> OTHER INFORMATION: Xaa = Glu, Asp, Ala or Gly
<220> FEATURE:
<221> NAME/KEY: VARIANT
<222> LOCATION: (19)...(19)
<223> OTHER INFORMATION: Xaa = Arg, Lys or Cys
<220> FEATURE:
<221> NAME/KEY: VARIANT
<222> LOCATION: (20)...(20)

```
<223> OTHER INFORMATION: Xaa = Phe, Leu, Trp, Ile, Val or Ala

<400> SEQUENCE: 1

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa
            20

<210> SEQ ID NO 2
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 2

Glu Leu Arg Glu Lys Leu Glu Ala Trp Phe Glu Leu Phe Arg Glu Phe
 1               5                  10                  15

Leu Glu Arg Phe
            20

<210> SEQ ID NO 3
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 3

Glu Leu Arg Glu Arg Leu Glu Ala Trp Phe Glu Leu Phe Arg Glu Phe
 1               5                  10                  15

Leu Glu Arg Phe
            20

<210> SEQ ID NO 4
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 4

Glu Leu Arg Asp Lys Leu Glu Ala Trp Phe Asp Leu Phe Arg Glu Phe
 1               5                  10                  15

Leu Glu Arg Phe
            20

<210> SEQ ID NO 5
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 5

Asp Leu Arg Asp Lys Leu Asp Ala Trp Phe Asp Leu Phe Arg Asp Phe
 1               5                  10                  15

Leu Asp Arg Phe
```

```
<210> SEQ ID NO 6
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 6

Glu Leu Arg Asp Arg Leu Glu Ala Trp Phe Asp Leu Phe Arg Glu Phe
 1               5                  10                  15

Leu Glu Arg Phe
         20

<210> SEQ ID NO 7
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 7

Asp Leu Arg Asp Arg Leu Asp Ala Trp Phe Asp Leu Phe Arg Asp Phe
 1               5                  10                  15

Leu Asp Arg Phe
         20

<210> SEQ ID NO 8
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 8

Glu Leu Arg Glu Lys Leu Glu Ala Trp Leu Glu Leu Leu Arg Glu Leu
 1               5                  10                  15

Leu Glu Arg Leu
         20

<210> SEQ ID NO 9
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 9

Glu Leu Arg Glu Arg Leu Glu Ala Trp Leu Glu Leu Leu Arg Glu Leu
 1               5                  10                  15

Leu Glu Arg Leu
         20

<210> SEQ ID NO 10
<211> LENGTH: 20
<212> TYPE: PRT
<213> ORGANISM: Artificial Sequence
<220> FEATURE:
```

-continued

<223> OTHER INFORMATION: synthetic amphipathic alpha-helix peptide
      ligand for ATP-binding cassette transporter A1 (ABCA1)
      having cholesterol efflux activity

<400> SEQUENCE: 10

Glu Leu Arg Asp Lys Leu Glu Ala Trp Leu Asp Leu Leu Arg Glu Leu
1               5                   10                  15

Leu Glu Arg Leu
            20

<210> SEQ ID NO 11
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 11

Asp Leu Arg Asp Lys Leu Asp Ala Trp Leu Asp Leu Leu Arg Asp Leu
1               5                   10                  15

Leu Asp Arg Leu
            20

<210> SEQ ID NO 12
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 12

Glu Leu Arg Asp Arg Leu Glu Ala Trp Leu Asp Leu Leu Arg Glu Leu
1               5                   10                  15

Leu Glu Arg Leu
            20

<210> SEQ ID NO 13
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 13

Asp Leu Arg Asp Arg Leu Asp Ala Trp Leu Asp Leu Leu Arg Asp Leu
1               5                   10                  15

Leu Asp Arg Leu
            20

<210> SEQ ID NO 14
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 14

Glu Val Arg Glu Lys Leu Glu Ala Trp Phe Glu Ala Phe Arg Glu Phe
1               5                   10                  15

Ala Glu Arg Phe Lys Ser
            20

<210> SEQ ID NO 15
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 15

Glu Val Arg Glu Lys Leu Glu Ala Trp Phe Glu Leu Phe Arg Glu Phe
1               5                   10                  15

Ala Glu Arg Phe Lys Ser
            20

<210> SEQ ID NO 16
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 16

Glu Val Arg Glu Lys Leu Glu Ala Trp Phe Glu Leu Phe Arg Glu Phe
1               5                   10                  15

Ala Glu Arg Phe Leu Ser
            20

<210> SEQ ID NO 17
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 17

Glu Val Arg Glu Lys Leu Glu Ala Trp Phe Glu Leu Phe Arg Glu Phe
1               5                   10                  15

Leu Glu Arg Phe Lys Ser
            20

<210> SEQ ID NO 18
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 18

Glu Val Arg Glu Lys Leu Glu Ala Trp Phe Glu Leu Phe Arg Glu Phe
1               5                   10                  15

Leu Glu Arg Phe Leu Ser
            20

<210> SEQ ID NO 19
<211> LENGTH: 21
<212> TYPE: PRT

```
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 19

Glu Val Arg Glu Lys Leu Glu Ala Trp Phe Glu Leu Phe Arg Glu Phe
1               5                   10                  15

Leu Glu Arg Phe Leu
            20

<210> SEQ ID NO 20
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 20

Glu Val Arg Glu Lys Leu Glu Ala Trp Phe Glu Leu Phe Arg Glu Phe
1               5                   10                  15

Leu Glu Arg Phe
            20

<210> SEQ ID NO 21
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 21

Glu Ile Arg Glu Lys Ile Glu Ala Trp Ile Glu Ile Ile Arg Glu Ile
1               5                   10                  15

Ile Glu Arg Ile
            20

<210> SEQ ID NO 22
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 22

Glu Leu Arg Glu Lys Leu Glu Ala Trp Phe Glu Leu Phe Glu Glu Phe
1               5                   10                  15

Phe Ala Arg Phe Lys Ser
            20

<210> SEQ ID NO 23
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 23
```

```
Glu Leu Arg Glu Lys Leu Glu Ala Trp Phe Glu Leu Phe Ala Glu Phe
1               5                   10                  15

Phe Ala Arg Phe Lys Ser
            20

<210> SEQ ID NO 24
<211> LENGTH: 21
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 24

Glu Leu Arg Glu Lys Leu Glu Ala Trp Phe Glu Leu Phe Ala Glu Phe
1               5                   10                  15

Phe Ala Arg Phe Lys
            20

<210> SEQ ID NO 25
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 25

Glu Leu Arg Glu Lys Leu Glu Ala Trp Phe Glu Leu Phe Ala Glu Phe
1               5                   10                  15

Phe Ala Arg Phe
            20

<210> SEQ ID NO 26
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 26

Glu Leu Arg Ala Lys Leu Glu Ala Trp Phe Glu Ala Phe Ala Glu Phe
1               5                   10                  15

Phe Ala Arg Phe
            20

<210> SEQ ID NO 27
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity
<220> FEATURE:
<221> NAME/KEY: VARIANT
<222> LOCATION: (1)...(1)
<223> OTHER INFORMATION: Xaa = Glu or Asp
<220> FEATURE:
<221> NAME/KEY: VARIANT
<222> LOCATION: (2)...(2)
<223> OTHER INFORMATION: Xaa = Leu, Ile or Val
<220> FEATURE:
<221> NAME/KEY: VARIANT
<222> LOCATION: (3)...(3)
```

```
<223> OTHER INFORMATION: Xaa = Lys or Arg
<220> FEATURE:
<221> NAME/KEY: VARIANT
<222> LOCATION: (4)...(4)
<223> OTHER INFORMATION: Xaa = Asp, Glu or Ala
<220> FEATURE:
<221> NAME/KEY: VARIANT
<222> LOCATION: (5)...(5)
<223> OTHER INFORMATION: Xaa = Lys or Arg
<220> FEATURE:
<221> NAME/KEY: VARIANT
<222> LOCATION: (6)...(6)
<223> OTHER INFORMATION: Xaa = Phe, Leu, Ile or Trp
<220> FEATURE:
<221> NAME/KEY: VARIANT
<222> LOCATION: (7)...(7)
<223> OTHER INFORMATION: Xaa = Glu or Asp
<220> FEATURE:
<221> NAME/KEY: VARIANT
<222> LOCATION: (9)...(9)
<223> OTHER INFORMATION: Xaa = Trp, Phe or Leu
<220> FEATURE:
<221> NAME/KEY: VARIANT
<222> LOCATION: (10)...(10)
<223> OTHER INFORMATION: Xaa = Phe, Leu, Ile or Trp
<220> FEATURE:
<221> NAME/KEY: VARIANT
<222> LOCATION: (11)...(11)
<223> OTHER INFORMATION: Xaa = Asp, Glu or Ala
<220> FEATURE:
<221> NAME/KEY: VARIANT
<222> LOCATION: (12)...(13)
<223> OTHER INFORMATION: Xaa = Phe, Leu, Ile or Trp
<220> FEATURE:
<221> NAME/KEY: VARIANT
<222> LOCATION: (14)...(14)
<223> OTHER INFORMATION: Xaa = Arg, Glu or Ala
<220> FEATURE:
<221> NAME/KEY: VARIANT
<222> LOCATION: (15)...(15)
<223> OTHER INFORMATION: Xaa = Glu or Asp
<220> FEATURE:
<221> NAME/KEY: VARIANT
<222> LOCATION: (16)...(17)
<223> OTHER INFORMATION: Xaa = Phe, Leu, Ile or Trp
<220> FEATURE:
<221> NAME/KEY: VARIANT
<222> LOCATION: (18)...(18)
<223> OTHER INFORMATION: Xaa = Glu or Asp
<220> FEATURE:
<221> NAME/KEY: VARIANT
<222> LOCATION: (19)...(19)
<223> OTHER INFORMATION: Xaa = Lys or Arg
<220> FEATURE:
<221> NAME/KEY: VARIANT
<222> LOCATION: (20)...(20)
<223> OTHER INFORMATION: Xaa = Phe, Leu, Ile or Trp

<400> SEQUENCE: 27

Xaa Xaa Xaa Xaa Xaa Xaa Xaa Ala Xaa Xaa Xaa Xaa Xaa Xaa Xaa Xaa
 1               5                   10                  15

Xaa Xaa Xaa Xaa
            20

<210> SEQ ID NO 28
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity
<220> FEATURE:
<221> NAME/KEY: VARIANT
<222> LOCATION: (1)...(1)
<223> OTHER INFORMATION: Xaa = Asp or Glu
<220> FEATURE:
```

```
<221> NAME/KEY: VARIANT
<222> LOCATION: (5)...(5)
<223> OTHER INFORMATION: Xaa = Lys or Arg
<220> FEATURE:
<221> NAME/KEY: VARIANT
<222> LOCATION: (7)...(7)
<223> OTHER INFORMATION: Xaa = Asp or Glu
<220> FEATURE:
<221> NAME/KEY: VARIANT
<222> LOCATION: (9)...(9)
<223> OTHER INFORMATION: Xaa = Trp, Leu or Phe
<220> FEATURE:
<221> NAME/KEY: VARIANT
<222> LOCATION: (10)...(10)
<223> OTHER INFORMATION: Xaa = Phe or Leu
<220> FEATURE:
<221> NAME/KEY: VARIANT
<222> LOCATION: (12)...(13)
<223> OTHER INFORMATION: Xaa = Phe or Leu
<220> FEATURE:
<221> NAME/KEY: VARIANT
<222> LOCATION: (15)...(15)
<223> OTHER INFORMATION: Xaa = Asp or Glu
<220> FEATURE:
<221> NAME/KEY: VARIANT
<222> LOCATION: (16)...(17)
<223> OTHER INFORMATION: Xaa = Phe or Leu
<220> FEATURE:
<221> NAME/KEY: VARIANT
<222> LOCATION: (18)...(18)
<223> OTHER INFORMATION: Xaa = Asp or Glu
<220> FEATURE:
<221> NAME/KEY: VARIANT
<222> LOCATION: (20)...(20)
<223> OTHER INFORMATION: Xaa = Phe or Leu

<400> SEQUENCE: 28

Xaa Leu Arg Ala Xaa Leu Xaa Ala Xaa Xaa Ala Xaa Xaa Arg Xaa Xaa
 1               5                  10                  15

Xaa Xaa Arg Xaa
            20

<210> SEQ ID NO 29
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity
<220> FEATURE:
<221> NAME/KEY: VARIANT
<222> LOCATION: (1)...(1)
<223> OTHER INFORMATION: Xaa = Asp or Glu
<220> FEATURE:
<221> NAME/KEY: VARIANT
<222> LOCATION: (4)...(4)
<223> OTHER INFORMATION: Xaa = Asp or Glu
<220> FEATURE:
<221> NAME/KEY: VARIANT
<222> LOCATION: (5)...(5)
<223> OTHER INFORMATION: Xaa = Lys or Arg
<220> FEATURE:
<221> NAME/KEY: VARIANT
<222> LOCATION: (7)...(7)
<223> OTHER INFORMATION: Xaa = Asp or Glu
<220> FEATURE:
<221> NAME/KEY: VARIANT
<222> LOCATION: (9)...(9)
<223> OTHER INFORMATION: Xaa = Phe, Leu or Trp
<220> FEATURE:
<221> NAME/KEY: VARIANT
<222> LOCATION: (10)...(10)
<223> OTHER INFORMATION: Xaa = Phe or Leu
<220> FEATURE:
<221> NAME/KEY: VARIANT
<222> LOCATION: (11)...(11)
```

```
<223> OTHER INFORMATION: Xaa = Asp or Glu
<220> FEATURE:
<221> NAME/KEY: VARIANT
<222> LOCATION: (12)...(13)
<223> OTHER INFORMATION: Xaa = Phe or Leu
<220> FEATURE:
<221> NAME/KEY: VARIANT
<222> LOCATION: (15)...(15)
<223> OTHER INFORMATION: Xaa = Asp or Glu
<220> FEATURE:
<221> NAME/KEY: VARIANT
<222> LOCATION: (16)...(17)
<223> OTHER INFORMATION: Xaa = Phe or Leu
<220> FEATURE:
<221> NAME/KEY: VARIANT
<222> LOCATION: (18)...(18)
<223> OTHER INFORMATION: Xaa = Asp or Glu
<220> FEATURE:
<221> NAME/KEY: VARIANT
<222> LOCATION: (20)...(20)
<223> OTHER INFORMATION: Xaa = Phe or Leu

<400> SEQUENCE: 29

Xaa Leu Arg Xaa Xaa Leu Xaa Ala Xaa Xaa Xaa Xaa Arg Xaa Xaa
 1               5                   10                  15

Xaa Xaa Arg Xaa
            20

<210> SEQ ID NO 30
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity
<220> FEATURE:
<221> NAME/KEY: VARIANT
<222> LOCATION: (4)...(4)
<223> OTHER INFORMATION: Xaa = Asp or Glu
<220> FEATURE:
<221> NAME/KEY: VARIANT
<222> LOCATION: (5)...(5)
<223> OTHER INFORMATION: Xaa = Lys or Arg
<220> FEATURE:
<221> NAME/KEY: VARIANT
<222> LOCATION: (9)...(9)
<223> OTHER INFORMATION: Xaa = Trp, Phe or Leu
<220> FEATURE:
<221> NAME/KEY: VARIANT
<222> LOCATION: (10)...(10)
<223> OTHER INFORMATION: Xaa = Phe or Leu
<220> FEATURE:
<221> NAME/KEY: VARIANT
<222> LOCATION: (11)...(11)
<223> OTHER INFORMATION: Xaa = Asp or Glu
<220> FEATURE:
<221> NAME/KEY: VARIANT
<222> LOCATION: (13)...(13)
<223> OTHER INFORMATION: Xaa = Phe or Leu
<220> FEATURE:
<221> NAME/KEY: VARIANT
<222> LOCATION: (16)...(16)
<223> OTHER INFORMATION: Xaa = Phe or Leu
<220> FEATURE:
<221> NAME/KEY: VARIANT
<222> LOCATION: (20)...(20)
<223> OTHER INFORMATION: Xaa = Phe or Leu

<400> SEQUENCE: 30

Glu Leu Arg Xaa Xaa Leu Glu Ala Xaa Xaa Xaa Leu Xaa Arg Glu Xaa
 1               5                   10                  15

Leu Glu Arg Xaa
            20
```

-continued

<210> SEQ ID NO 31
<211> LENGTH: 22
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 31

Glu Leu Arg Glu Lys Leu Glu Ala Trp Phe Glu Leu Phe Arg Glu Phe
1               5                   10                  15

Leu Glu Arg Phe Lys Ser
            20

<210> SEQ ID NO 32
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 32

Glu Leu Arg Glu Lys Leu Glu Ala Leu Phe Glu Leu Phe Arg Glu Phe
1               5                   10                  15

Leu Glu Arg Phe
            20

<210> SEQ ID NO 33
<211> LENGTH: 20
<212> TYPE: PRT
<213> ORGANISM: Artificial Sequence
<220> FEATURE:
<223> OTHER INFORMATION: synthetic amphipathic alpha-helix peptide
      ligand for ATP-binding cassette transporter A1 (ABCA1)
      having cholesterol efflux activity

<400> SEQUENCE: 33

Glu Leu Arg Glu Lys Leu Glu Ala Phe Phe Glu Leu Phe Arg Glu Phe
1               5                   10                  15

Leu Glu Arg Phe
            20

<210> SEQ ID NO 34
<211> LENGTH: 22
<212> TYPE: PRT
<213> ORGANISM: Artificial Sequence
<220> FEATURE:
<223> OTHER INFORMATION: synthetic amphipathic alpha-helix peptide
      N257-11 ligand for ATP-binding cassette transporter A1
      (ABCA1) having cholesterol efflux activity

<400> SEQUENCE: 34

Glu Leu Arg Glu Lys Leu Glu Ala Trp Arg Glu Ala Phe Glu Glu Phe
1               5                   10                  15

Phe Ala Arg Phe Lys Ser
            20

<210> SEQ ID NO 35
<211> LENGTH: 22
<212> TYPE: PRT
<213> ORGANISM: Artificial Sequence
<220> FEATURE:
<223> OTHER INFORMATION: synthetic amphipathic alpha-helix peptide
      N356-1 ligand for ATP-binding cassette transporter A1

(ABCA1) having cholesterol efflux activity

<400> SEQUENCE: 35

Glu Leu Arg Glu Lys Leu Glu Ala Trp Phe Glu Ala Phe Glu Glu Phe
1               5                   10                  15

Phe Ala Arg Phe Lys Ser
            20

<210> SEQ ID NO 36
<211> LENGTH: 22
<212> TYPE: PRT
<213> ORGANISM: Artificial Sequence
<220> FEATURE:
<223> OTHER INFORMATION: synthetic amphipathic alpha-helix peptide
      N356-2 ligand for ATP-binding cassette transporter A1
      (ABCA1) having cholesterol efflux activity

<400> SEQUENCE: 36

Glu Leu Arg Glu Lys Leu Glu Ala Trp Arg Glu Leu Phe Glu Glu Phe
1               5                   10                  15

Phe Ala Arg Phe Lys Ser
            20

<210> SEQ ID NO 37
<211> LENGTH: 22
<212> TYPE: PRT
<213> ORGANISM: Artificial Sequence
<220> FEATURE:
<223> OTHER INFORMATION: synthetic amphipathic alpha-helix peptide
      N356-3 ligand for ATP-binding cassette transporter A1
      (ABCA1) having cholesterol efflux activity

<400> SEQUENCE: 37

Glu Leu Arg Glu Lys Leu Glu Ala Trp Phe Glu Leu Phe Glu Glu Phe
1               5                   10                  15

Phe Ala Arg Phe Lys Ser
            20

<210> SEQ ID NO 38
<211> LENGTH: 22
<212> TYPE: PRT
<213> ORGANISM: Artificial Sequence
<220> FEATURE:
<223> OTHER INFORMATION: synthetic amphipathic alpha-helix peptide
      N356-4 ligand for ATP-binding cassette transporter A1
      (ABCA1) having cholesterol efflux activity

<400> SEQUENCE: 38

Glu Leu Arg Glu Lys Leu Glu Ala Trp Phe Glu Leu Phe Ala Glu Phe
1               5                   10                  15

Phe Ala Arg Phe Lys Ser
            20

<210> SEQ ID NO 39
<211> LENGTH: 21
<212> TYPE: PRT
<213> ORGANISM: Artificial Sequence
<220> FEATURE:
<223> OTHER INFORMATION: synthetic amphipathic alpha-helix peptide
      N356-5 ligand for ATP-binding cassette transporter A1
      (ABCA1) having cholesterol efflux activity

<400> SEQUENCE: 39

Glu Leu Arg Glu Lys Leu Glu Ala Trp Phe Glu Leu Phe Ala Glu Phe
1               5                   10                  15

Phe Ala Arg Phe Lys

20

<210> SEQ ID NO 40
<211> LENGTH: 20
<212> TYPE: PRT
<213> ORGANISM: Artificial Sequence
<220> FEATURE:
<223> OTHER INFORMATION: synthetic amphipathic alpha-helix peptide
      N356-6 ligand for ATP-binding cassette transporter A1
      (ABCA1) having cholesterol efflux activity

<400> SEQUENCE: 40

Glu Leu Arg Glu Lys Leu Glu Ala Trp Phe Glu Leu Phe Ala Glu Phe
1               5                   10                  15

Phe Ala Arg Phe
            20

<210> SEQ ID NO 41
<211> LENGTH: 20
<212> TYPE: PRT
<213> ORGANISM: Artificial Sequence
<220> FEATURE:
<223> OTHER INFORMATION: synthetic amphipathic alpha-helix peptide
      N356-7 ligand for ATP-binding cassette transporter A1
      (ABCA1) having cholesterol efflux activity

<400> SEQUENCE: 41

Glu Leu Arg Ala Lys Leu Glu Ala Trp Phe Glu Ala Phe Ala Glu Phe
1               5                   10                  15

Phe Ala Arg Phe
            20

<210> SEQ ID NO 42
<211> LENGTH: 22
<212> TYPE: PRT
<213> ORGANISM: Artificial Sequence
<220> FEATURE:
<223> OTHER INFORMATION: synthetic amphipathic alpha-helix peptide
      N965-1 ligand for ATP-binding cassette transporter A1
      (ABCA1) having cholesterol efflux activity

<400> SEQUENCE: 42

Glu Val Arg Glu Lys Leu Glu Ala Trp Phe Glu Ala Phe Arg Glu Phe
1               5                   10                  15

Ala Glu Arg Phe Lys Ser
            20

<210> SEQ ID NO 43
<211> LENGTH: 22
<212> TYPE: PRT
<213> ORGANISM: Artificial Sequence
<220> FEATURE:
<223> OTHER INFORMATION: synthetic amphipathic alpha-helix peptide
      N965-2 ligand for ATP-binding cassette transporter A1
      (ABCA1) having cholesterol efflux activity

<400> SEQUENCE: 43

Glu Val Arg Glu Lys Leu Glu Ala Trp Phe Glu Leu Phe Arg Glu Phe
1               5                   10                  15

Ala Glu Arg Phe Lys Ser
            20

<210> SEQ ID NO 44
<211> LENGTH: 22
<212> TYPE: PRT
<213> ORGANISM: Artificial Sequence
<220> FEATURE:

```
<223> OTHER INFORMATION: synthetic amphipathic alpha-helix peptide
      N965-3 ligand for ATP-binding cassette transporter A1
      (ABCA1) having cholesterol efflux activity

<400> SEQUENCE: 44

Glu Val Arg Glu Lys Leu Glu Ala Trp Phe Glu Leu Phe Arg Glu Phe
1               5                   10                  15

Ala Glu Arg Phe Leu Ser
            20

<210> SEQ ID NO 45
<211> LENGTH: 22
<212> TYPE: PRT
<213> ORGANISM: Artificial Sequence
<220> FEATURE:
<223> OTHER INFORMATION: synthetic amphipathic alpha-helix peptide
      N965-4 ligand for ATP-binding cassette transporter A1
      (ABCA1) having cholesterol efflux activity

<400> SEQUENCE: 45

Glu Val Arg Glu Lys Leu Glu Ala Trp Phe Glu Leu Phe Arg Glu Phe
1               5                   10                  15

Leu Glu Arg Phe Lys Ser
            20

<210> SEQ ID NO 46
<211> LENGTH: 22
<212> TYPE: PRT
<213> ORGANISM: Artificial Sequence
<220> FEATURE:
<223> OTHER INFORMATION: synthetic amphipathic alpha-helix peptide
      N965-5 ligand for ATP-binding cassette transporter A1
      (ABCA1) having cholesterol efflux activity

<400> SEQUENCE: 46

Glu Val Arg Glu Lys Leu Glu Ala Trp Phe Glu Leu Phe Arg Glu Phe
1               5                   10                  15

Leu Glu Arg Phe Leu Ser
            20

<210> SEQ ID NO 47
<211> LENGTH: 21
<212> TYPE: PRT
<213> ORGANISM: Artificial Sequence
<220> FEATURE:
<223> OTHER INFORMATION: synthetic amphipathic alpha-helix peptide
      N965-6 ligand for ATP-binding cassette transporter A1
      (ABCA1) having cholesterol efflux activity

<400> SEQUENCE: 47

Glu Val Arg Glu Lys Leu Glu Ala Trp Phe Glu Leu Phe Arg Glu Phe
1               5                   10                  15

Leu Glu Arg Phe Leu
            20

<210> SEQ ID NO 48
<211> LENGTH: 20
<212> TYPE: PRT
<213> ORGANISM: Artificial Sequence
<220> FEATURE:
<223> OTHER INFORMATION: synthetic amphipathic alpha-helix peptide
      N965-7 ligand for ATP-binding cassette transporter A1
      (ABCA1) having cholesterol efflux activity

<400> SEQUENCE: 48

Glu Val Arg Glu Lys Leu Glu Ala Trp Phe Glu Leu Phe Arg Glu Phe
1               5                   10                  15
```

```
Leu Glu Arg Phe
            20

<210> SEQ ID NO 49
<211> LENGTH: 20
<212> TYPE: PRT
<213> ORGANISM: Artificial Sequence
<220> FEATURE:
<223> OTHER INFORMATION: synthetic amphipathic alpha-helix peptide
      N965-8 ligand for ATP-binding cassette transporter A1
      (ABCA1) having cholesterol efflux activity

<400> SEQUENCE: 49

Glu Leu Arg Glu Lys Leu Glu Ala Trp Phe Glu Leu Phe Arg Glu Phe
1               5                   10                  15

Leu Glu Arg Phe
            20

<210> SEQ ID NO 50
<211> LENGTH: 22
<212> TYPE: PRT
<213> ORGANISM: Artificial Sequence
<220> FEATURE:
<223> OTHER INFORMATION: synthetic amphipathic alpha-helix peptide
      N965-9 ligand for ATP-binding cassette transporter A1
      (ABCA1) having cholesterol efflux activity

<400> SEQUENCE: 50

Glu Leu Arg Glu Lys Leu Glu Ala Trp Arg Glu Leu Phe Glu Glu Phe
1               5                   10                  15

Phe Ala Arg Phe Leu Ser
            20

<210> SEQ ID NO 51
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-1 ligand for ATP-binding cassette transporter A1
      (ABCA1) having cholesterol efflux activity

<400> SEQUENCE: 51

Glu Leu Arg Glu Arg Leu Glu Ala Trp Phe Glu Leu Phe Arg Glu Phe
1               5                   10                  15

Leu Glu Arg Phe
            20

<210> SEQ ID NO 52
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-2 ligand for ATP-binding cassette transporter A1
      (ABCA1) having cholesterol efflux activity

<400> SEQUENCE: 52

Glu Leu Arg Asp Lys Leu Glu Ala Trp Phe Asp Leu Phe Arg Glu Phe
1               5                   10                  15

Leu Glu Arg Phe
            20

<210> SEQ ID NO 53
<211> LENGTH: 20
<212> TYPE: PRT
```

```
<213> ORGANISM: Artificial Sequence
<220> FEATURE:
<223> OTHER INFORMATION: synthetic amphipathic alpha-helix peptide
      N1154-3 ligand for ATP-binding cassette transporter A1
      (ABCA1) having cholesterol efflux activity

<400> SEQUENCE: 53

Asp Leu Arg Asp Lys Leu Asp Ala Trp Phe Asp Leu Phe Arg Asp Phe
 1               5                  10                  15

Leu Asp Arg Phe
         20

<210> SEQ ID NO 54
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-4 ligand for ATP-binding cassette transporter A1
      (ABCA1) having cholesterol efflux activity

<400> SEQUENCE: 54

Glu Leu Arg Asp Arg Leu Glu Ala Trp Phe Asp Leu Phe Arg Glu Phe
 1               5                  10                  15

Leu Glu Arg Phe
         20

<210> SEQ ID NO 55
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-5 ligand for ATP-binding cassette transporter A1
      (ABCA1) having cholesterol efflux activity

<400> SEQUENCE: 55

Asp Leu Arg Asp Arg Leu Asp Ala Trp Phe Asp Leu Phe Arg Asp Phe
 1               5                  10                  15

Leu Asp Arg Phe
         20

<210> SEQ ID NO 56
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-6 ligand for ATP-binding cassette transporter A1
      (ABCA1) having cholesterol efflux activity

<400> SEQUENCE: 56

Glu Leu Arg Glu Lys Leu Glu Ala Trp Leu Glu Leu Leu Arg Glu Leu
 1               5                  10                  15

Leu Glu Arg Leu
         20

<210> SEQ ID NO 57
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-7 ligand for ATP-binding cassette transporter A1
      (ABCA1) having cholesterol efflux activity

<400> SEQUENCE: 57
```

-continued

Glu Leu Arg Glu Arg Leu Glu Ala Trp Leu Glu Leu Leu Arg Glu Leu
1               5                   10                  15

Leu Glu Arg Leu
            20

<210> SEQ ID NO 58
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-8 ligand for ATP-binding cassette transporter A1
      (ABCA1) having cholesterol efflux activity

<400> SEQUENCE: 58

Glu Leu Arg Asp Lys Leu Glu Ala Trp Leu Asp Leu Leu Arg Glu Leu
1               5                   10                  15

Leu Glu Arg Leu
            20

<210> SEQ ID NO 59
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-9 ligand for ATP-binding cassette transporter A1
      (ABCA1) having cholesterol efflux activity

<400> SEQUENCE: 59

Asp Leu Arg Asp Lys Leu Asp Ala Trp Leu Asp Leu Leu Arg Asp Leu
1               5                   10                  15

Leu Asp Arg Leu
            20

<210> SEQ ID NO 60
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-10 ligand for ATP-binding cassette transporter A1
      (ABCA1) having cholesterol efflux activity

<400> SEQUENCE: 60

Glu Leu Arg Asp Arg Leu Glu Ala Trp Leu Asp Leu Leu Arg Glu Leu
1               5                   10                  15

Leu Glu Arg Leu
            20

<210> SEQ ID NO 61
<211> LENGTH: 20
<212> TYPE: PRT
<213> ORGANISM: Artificial Sequence
<220> FEATURE:
<223> OTHER INFORMATION: synthetic amphipathic alpha-helix peptide
      N1154-11 ligand for ATP-binding cassette transporter A1
      (ABCA1) having cholesterol efflux activity

<400> SEQUENCE: 61

Asp Leu Arg Asp Arg Leu Asp Ala Trp Leu Asp Leu Leu Arg Asp Leu
1               5                   10                  15

Leu Asp Arg Leu
            20

<210> SEQ ID NO 62

-continued

```
<211> LENGTH: 6
<212> TYPE: PRT
<213> ORGANISM: Artificial Sequence
<220> FEATURE:
<223> OTHER INFORMATION: synthetic Factor Xa cleavage site

<400> SEQUENCE: 62

Met His Ile Glu Gly Arg
1               5
```

PEPTIDE MEDIATORS OF CHOLESTEROL EFFLUX

CROSS-REFERENCES TO RELATED APPLICATIONS

This application is a U.S. National Stage Application of International Application No. PCT/US2009/047694, filed Jun. 17, 2009, which claims the benefit of U.S. Provisional Patent Application No. 61/073,708, filed on Jun. 18, 2008, is the disclosures of which are herein incorporated by reference in their entirety for all purposes.

Subject matter in this application is also related to PCT application number PCT/US07/87477, filed Dec. 13, 2007, the disclosure of which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Grant (Contract) No. R03-AG023153 awarded by the National Institutes of Aging. The Government has certain rights in this invention.

The research leading to this invention was also funded by a sponsored research agreement with Artery Therapeutics, Inc. (LBNL Work for Other Agreement No. LB05-001119) and by Grant No. 13IT-0025 awarded by the Tobacco Related Disease Research Program of the State of California.

BACKGROUND OF THE INVENTION

Cardiovascular disease (CVD) is a leading cause of morbidity and mortality in the United States and throughout the world. The accumulation of cholesterol in macrophages in the artery wall promotes foam-cell formation and atherosclerosis constituting a main cause of CVD (Schmitz, G. and Kaminski, W. E., "ATP-binding cassette (ABC) transporters in atherosclerosis," *Curr Atheroscler Rep.,* 4(3):243-51 (2002). Cholesterol accumulation in macrophages is largely dependent on the balance between the deposition by Apolipoprotein B-containing lipoprotein particles, such as VLDL, IDL and LDL, and the cholesterol removal by ApoA-I and ApoE particles. Lowering of plasma LDL concentrations by statins and other cholesterol lowering medications prevents approximately one-third of the CVD events, while two-thirds of the events remain (see, e.g., "Randomized trial of cholesterol lowering in 4444 patients with coronary heart disease: the Scandinavian Simvastatin Survival Study (4S), *Lancet,* 344 (8934):1383-1389 (1994); and "Influence of pravastatin and plasma lipids on clinical events in the West of Scotland Coronary Prevention Study (WOSCOPS), *Circulation,* 197(15): 1440-5 (1998). The latter constitutes a huge unmet medical need.

Elevated levels of plasma HDL cholesterol are associated with reduced risk of atherosclerosis (Gordon et al., "High Density Lipoprotein As A Protective Factor Against Coronary Heart Disease," *Am. J. Med.,* 62:707-14 (1977)). Recent epidemiological studies have been able to ascribe the HDL protective effect to its main apolipoprotein, Apo A-I (Walldius, G, et al., High Apolipoprotein B, Low Apolipoprotein A-I, And Improvement In The Prediction of Fatal Myocardial Infarction (AMORIS study): A Prospective Study," *Lancet,* 358(9298):2026-33 (2001); and Yusuf et al., "Effect of Potentially Modifiable Risk Factors Associated With Myocardial Infarction in 52 Countries (the INTERHEART study): Case-control Study," *Lancet,* 364(9438):937-52 (2004)). The beneficial effects of HDL are related, in part, to activity in mediating the anti-atherogenic reverse cholesterol transport (RCT) pathway. RCT involves the transport of cholesterol from peripheral macrophages to the liver for excretion of sterol in feces (Lewis et al., "New Insights Into The Regulation of HDL Metabolism and Reverse Cholesterol Transport," *Circ. Res.,* 96:1221-32 (2005)). The rate-limiting step of RCT involves stimulation of cholesterol efflux from macrophages, mediated by native apolipoproteins such as Apo A-I and Apo E. This process of cholesterol efflux generates nascent HDL and requires the ATP-binding cassette transporter A1 (ABCA1) or else atherosclerosis is developed (Calpe-Berdiel et al., "Direct Evidence In Vivo of Impaired Macrophage-Specific Reverse Cholesterol Transport in ATP-Binding Cassette Transporter A1-Deficient Mice," *Biochim. Biophys. Acta.,* 1738 (1-3):6-9 (2005). ABCA1 is the defective molecule in Tangiers disease, which is characterized by severe deficiency in plasma HDL and premature atherosclerosis (Attie et al., "Pivotal Role of ABCA1 in Reverse Cholesterol Transport Influencing HDL Levels and Susceptibility to Atherosclerosis," *J Lipid Res.,* 42(11):1717-26 (2001)). Apolipoproteins A and E also stabilize cellular ABCA1 protein by preventing its degradation, which ensures high-levels of cellular cholesterol export and HDL assembly.

The clinical importance of HDL has sparked interest in the development of strategies to manipulate RCT for therapeutic purposes. Explorative proof of concept studies have shown that injections with full length Apo A-I variants, e.g., proApoA-I, Apo A-I Milano, and Apo A-I2 wild type in phospholipid complexes increases RCT (Eriksson et al., Stimulation of Fecal Steroid Excretion After Infusion of Recombinant Proapolipoprotein A-I. Potential Reverse Cholesterol Transport in Humans," *Circulation,* 100(6):594-8 (1999)), and regress coronary atherosclerosis (Nissen et al., "Effect of Recombinant ApoA-I Milano on Coronary Atherosclerosis in Patients with Acute Coronary Syndromes: A Randomized Controlled Trial," *JAMA,* 290(17):2292-300 (2003); and Tardif et al., "Effect of rHDL on Atherosclerosis-Safety and Efficacy (ERASE) Investigators," *JAMA,* 297:1675-82. Epub March 26 (2007)). Albeit promising full length ApoA-I protein have several drawbacks as a therapeutics if they are to be developed into commercial products. For instance, Apo A-I is a 243 amino acid long protein that is far from trivial to produce in the quantities needed for a commercial product. In addition, Apo A-I variants, such as the Milano and Paris variants, may evoke immunologic responses due to their foreign nature.

Thus, there is a need in the art for additional compositions and methods utilizing the potent RCT pathway to mediate cholesterol efflux for stabilizing and regressing atherosclerotic plaques, i.e., for treating cardiovascular disease. Surprisingly, the present invention fulfills this need as well as other needs by providing such compositions and methods.

SUMMARY OF THE INVENTION

The present invention relates to peptides that have effects on lipid metabolism. Lipids are an important cell structural component and provide source material for fundamental cell signaling including prostaglandins, reactive oxidative species, and the like. Through signaling pathways, lipids also contribute to the orchestration of cytokine responses, e.g., to inflammatory stimuli. Such lipid effects are implicated in several disease states including but not limited to, atherosclerosis and neurological, inflammatory and infectious disease manifestations. The peptides exert their effects directly or through mediators. Mediators include, but are not limited to, HDL, ABC transporters, and mediators for oxidation and inflammation.

In one aspect, the invention therefore provides a family of polypeptides having cholesterol efflux activity that parallels, and preferably exceeds on a weight basis, that of full-length apolipoproteins (e.g., Apo AI and Apo E); and having high selectivity for ABCA1 that parallels that of full-length apolipoproteins. More particularly, the present invention provides a family of non-naturally occurring polypeptides that act as high-affinity functional ligands for ABCA1 and that stimulate cellular cholesterol efflux with approximately the capacity and potency of native apolipoproteins on a per molecule basis. The polypeptides of the present invention stimulate cholesterol efflux from macrophage foam cells in vivo, promote a sustained increase in fecal sterol secretion, and reduce the severity of atherosclerosis in hypercholesterolemic mice.

As such, the polypeptides of the present invention, i.e., polypeptides that have potent and selective activity for ABCA1, can be used therapeutically to promote ABCA1-stabilization as well as ABCA1-lipid efflux activity, and can be used alone or, alternatively, in combination with other known pharmacological agents for the treatment of cardiovascular disease to reduce atherosclerosis. In addition, the polypeptides of the present invention can be used alone or, alternatively, in combination with other known pharmacological agents for the treatment of acute coronary syndrome to reduce plaque lipid content and to stabilize vulnerable plaques. Further, the polypeptides of the present invention can be used alone or, alternatively, in combination with other known pharmacological agents for the treatment of dyslipidemia, hypercholesterolemia and inflammation to raise plasma HDL concentrations and/or to promote reverse cholesterol transport.

The peptides of the invention comprise certain features that together define the pharmacokinetic and pharmacodynamic properties of the peptides. These features include an α-helix structure and amphipathic orientation of amino acids along the axis of the α-helix structure. The peptides comprise two separate acidic residue foci along the hydrophilic axis. The α-helix structure is further enforced by natural amino acid salt bridge formation in the lipid-water inter phase. The peptides also lack substantial stereo-specific effect, e.g., peptides that comprise L and D amino acids and inverted forms work equally well. The peptides comprise a core sequence of 20 amino acid residues that selectively bind to HDL in plasma and target the ABCA1 transporter in cells.

Pharmacodynamics are facilitated by the hydrophobic properties, e.g., the hydrophobic wedge angle along the axis of the α-helix positions the peptide in the cell membrane in the vicinity of the ABCA1 transporter, thereby allowing functional interaction. Thus the peptides interact with cell membranes in a physiological way in that they confer ABCA1-specific lipid efflux with minimal non-specific cell membrane effects.

In a further aspect, the invention is based, in part, on the discovery that the non-polar surface area of a single helix can be expanded (i.e., the hydrophobic footprint can be increased) in a small peptide of 20 amino acids in length by using hydrophobic residues such as L, F, I, W, at appropriate positions in the helix, e.g., positions 10, 12, etc., to provided a small single helix peptide that has the 20 amino acid core sequence and has native ABCA1 efflux stimulating activity, i.e., achieves an ABCA1 efflux activity that is comparable to the cholesterol efflux activity of a native protein, e.g., ApoAI, that has multiple amphipathic α-helices linked via prolines.

Further, in some embodiments, the invention provides a peptide of 20 amino acids in length that has an expanded hydrophobic footprint where the peptide is able to bind to HDL at a level that obviates the need for phospholipid formulation.

In one aspect, the present invention provides an isolated polypeptide that comprises (and, in certain embodiments, consists of or, alternatively, consists essentially of) the amino acid sequence: $X_1X_2X_3X_4X_5X_6X_7X_8X_9X_{10}X_{11}X_{12}$, $X_{13}$, $X_{14}$, $X_{15}X_{16}X_{17}X_{18}X_{19}X_{20}$ wherein: $X_1$, $X_7$, $X_{11}$, and $X_{15}$ are amino acids independently selected from the group consisting of E and D; $X_4$ and $X_{18}$ are amino acids independently selected from the group consisting of E, D, and A; $X_9$, $X_{10}$, $X_{13}$, $X_{16}$ and $X_{20}$ are amino acids independently selected from the group consisting of F, L, and W; $X_{17}$ is an amino acid L, A, F, or W; $X_3$, $X_5$, and $X_{19}$ are amino acids independently selected from the group consisting of R and K; $X_{14}$ is an amino acid R, A, or E; and $X_2$, $X_6$, $X_8$, and $X_{12}$ are amino acids independently selected from the group consisting of L, V and A; wherein each letter stands for the conventional one-letter amino acid code.

The invention also provides a polypeptide that comprises (and, in certain embodiments, consists of or, alternatively, consists essentially of) the amino acid sequence: $X_1X_2X_3X_4X_5X_6X_7X_8X_9X_{10}X_{11}X_{12}X_{13}X_{14}X_{15}X_{16}X_{17}X_{18}X_{19}X_{20}$ (SEQ ID NO:1) wherein: $X_1$, $X_7$, and $X_{15}$ are amino acids independently selected from the group consisting of E and D; $X_4$, $X_{11}$, and $X_{18}$ are amino acids independently selected from the group consisting of E, D, A and G; $X_2$, $X_6$, $X_9$, $X_{10}$, $X_{12}$, $X_{13}$, $X_{16}$, $X_{17}$, and $X_{20}$ are amino acids independently selected from the group consisting of F, L, W, I, V, and A; $X_3$, $X_5$, and $X_{19}$ are amino acids independently selected from the group consisting of R, K, and C; $X_{14}$ is an amino acid R, A, E, or C; and $X_8$ is A, G, or V. In some embodiments of such peptides of the invention, $X_2$, $X_6$, $X_9$, $X_{10}$, $X_{12}$, $X_{13}$, $X_{16}$, $X_{17}$, and $X_{20}$ are independently selected from the group consisting of F, L, I and W. In some embodiments, $X_4$, $X_{11}$, and $X_{18}$ are independently selected from the group consisting of A, D, and E. In some embodiments, positions $X_4$ and $X_{11}$ are A. In some embodiments, positions $X_4$ and $X_{11}$ are independently selected from the group consisting of D and E. In some embodiments, $X_9$ is L, F, or W. In some embodiments, at least three of positions $X_2$, $X_6$, $X_{12}$, and $X_{17}$ are L. In some embodiments, $X_{14}$ is R; and $X_{17}$ is L or F. In some embodiments $X_8$ is A. In some embodiments, $X_2$ is L or V. In some embodiments $X_6$, $X_{10}$, $X_{12}$, $X_{13}$, $X_{16}$, $X_{17}$, and $X_{20}$ are independently selected from the group consisting of F, L, I, and W. In some embodiments, $X_6$, $X_{10}$, $X_{12}$, $X_{13}$, $X_{16}$, $X_{17}$, and $X_{20}$ are independently selected from the group consisting of F and L.

In some embodiments, a peptide of the invention comprises (and, in certain embodiments, consists of or, alternatively, consists essentially of), the amino acid sequence: $X_1X_2X_3X_4X_5X_6X_7AX_9X_{10}X_{11}X_{12}X_{13}X_{14}X_{15}X_{16}X_{17}X_{18}X_{19}X_{20}$ (SEQ ID NO:27), wherein: $X_1$, $X_7$, $X_{15}$, and $X_{18}$ are independently selected from the group consisting of D and E; $X_2$ is L, I, or V; $X_4$ and $X_{11}$ are independently selected from the group consisting of D, E, and A; $X_3$, $X_5$ and $X_{19}$ are independently selected from the group consisting of K and R; $X_9$ is W, F or L; $X_{14}$ is R, E, or A; and $X_6$, $X_{10}$, $X_{12}$, $X_{13}$, $X_{16}$, $X_{17}$, and $X_{20}$ are independently selected from the group consisting of F, L, I, and W. In some embodiments, $X_{10}$, $X_{12}$, $X_{13}$, $X_{16}$, $X_{17}$, and $X_{20}$ are independently selected from the group consisting of F and L.

In some embodiments, the invention provides a peptide that comprises (and, in certain embodiments, consists of or, alternatively, consists essentially of), the amino acid sequence:

$X_1LRAX_5LX_7AX_9X_{10}AX_{12}X_{13}RX_{15}X_{16}X_{17}X_{18}RX_{20}$ (SEQ ID NO:28), wherein $X_1$, $X_7$, $X_{15}$, and $X_{18}$ are independently selected from the group consisting of D and E; $X_5$ is K or R; $X_9$ is W, L or F; and $X_{10}$, $X_{12}$, $X_{13}$, $X_{16}$, $X_{17}$, and $X_{20}$ are independently selected from the group consisting of F and L.

In some embodiments, the invention provides a peptide that comprises (and, in certain embodiments, consists of or, alternatively, consists essentially of) the amino acid sequence: $X_1LRX_4X_5LX_7X_8X_9X_{10}X_{11}X_{12}X_{13}RX_{15}X_{16}X_{17}X_{18}RX_{20}$ (SEQ ID NO:29), wherein $X_1$, $X_4$, $X_7$, $X_{11}$, $X_{15}$, and $X_{18}$ are independently selected from the group consisting of D and E; $X_5$ is K or R; $X_9$ is F, L or W; and $X_{10}$, $X_{12}$, $X_{13}$, $X_{16}$, $X_{17}$, and $X_{20}$ are independently selected from the group consisting of F and L.

In some embodiments, a peptide of the invention comprises (and, in certain embodiments, consists of or, alternatively, consists essentially of):

```
                                          (SEQ ID NO: 30)
ELR(D/E)(K/R)LEA(W/F/L)(F/L)(D/E)L(F/L)RE(F/L)

LER(F/L).
```

In some embodiments, the peptides of the invention as described herein further comprises $X_{21}$, wherein $X_{21}$ is selected from the group consisting of C, K, Y, or L. In some embodiments, the polypeptide of the invention further comprises $X_{21}$ and $X_{22}$, wherein $X_{21}$ is selected from the group consisting of C, K, Y, and L, and $X_{22}$ is S or C. In some embodiments, $X_{21}$ is K. In some embodiments, $X_{22}$ is S. In some embodiments, $X_{21}$ or $X_{22}$ is C. The polypeptides of the invention have cholesterol efflux activity and ABCA1-stabilization activity.

In some embodiments, a cysteine is introduced into a peptide of the invention, e.g., a peptide selected from the group consisting of SEQ ID NO:2-33, as a substitution for a positively charged amino acid, e.g., arginine or lysine, at the lipid-water interface of the amphipathic α-helix. Typically, a peptide of the invention comprising a cysteine substitution has one cysteine per peptide and/or helical segment. Thus in some embodiments, a cysteine is present at position 3, 5, 14, or 19 of SEQ ID NO:1, or is substituted at position 3, 5, 14, or 19 of SEQ ID NO:27, 28, 39, or 30. For example, in certain embodiments a peptide of the invention, e.g., SEQ ID NO:2, comprises one of the following substitutions: R3-->C, K5-->C, R14-->C and R19-->C. In some embodiments, a peptide of SEQ ID NO:27, 28, 29, or 30 may also comprise a cysteine substitution at position 3, 5, 14, or 19. In certain embodiments, a peptide of the invention may comprise a cysteine at SEQ ID NO:1 or a cysteine that is substituted at position 3, 5, 14, or 19 of SEQ ID NO:27, 28, 39, or 30, and a second cysteine residue at position 21 or 22.

In some embodiments a polypeptide of the present invention comprises (and, in certain embodiments, consists of or, alternatively, consists essentially of) an amino acid sequence selected from the group consisting of:

```
ELREKLEAWFELFREFLERF,     (SEQ ID NO: 2)

ELRERLEAWFELFREFLERF,     (SEQ ID NO: 3)

ELRDKLEAWFDLFREFLERF,     (SEQ ID NO: 4)

DLRDKLDAWFDLFRDFLDRF,     (SEQ ID NO: 5)

ELRDRLEAWFDLFREFLERF,     (SEQ ID NO: 6)

DLRDRLDAWFDLFRDFLDRF,     (SEQ ID NO: 7)

ELREKLEAWLELLRELLERL,     (SEQ ID NO: 8)

ELRERLEAWLELLRELLERL,     (SEQ ID NO: 9)

ELRDKLEAWLDLLRELLERL,     (SEQ ID NO: 10)

DLRDKLDAWLDLLRDLLDRL,     (SEQ ID NO: 11)

ELRDRLEAWLDLLRELLERL,     (SEQ ID NO: 12)

DLRDRLDAWLDLLRDLLDRL,     (SEQ ID NO: 13)

EVREKLEAWFEAFREFAERFKS.   (SEQ ID NO: 14)

EVREKLEAWFELFREFAERFKS,   (SEQ ID NO: 15)

EVREKLEAWFELFREFAERFLS,   (SEQ ID NO: 16)

EVREKLEAWFELFREFLERFKS,   (SEQ ID NO: 17)

EVREKLEAWFELFREFLERFLS,   (SEQ ID NO: 18)

EVREKLEAWFELFREFLERFL,    (SEQ ID NO: 19)

EVREKLEAWFELFREFLERF,     (SEQ ID NO: 20)

EIREKIEAWIEIIREIIERI,     (SEQ ID NO: 21)

ELREKLEAWFELFEEFFARFKS,   (SEQ ID NO: 22)

ELREKLEAWFELFAEFFARFKS,   (SEQ ID NO: 23)

ELREKLEAWFELFAEFFARFK,    (SEQ ID NO: 24)

ELREKLEAWFELFAEFFARF,     (SEQ ID NO: 25)

ELRAKLEAWFEAFAEFFARF,     (SEQ ID NO: 26)

ELREKLEAWFELFREFLERFKS    (SEQ ID NO: 31)

ELREKLEALFELFREFLERF,     (SEQ ID NO: 32)
and

ELREKLEAFFELFREFLERF.     (SEQ ID NO: 33)
```

In another aspect, the present invention provides polypeptide variants of the polypeptides having and amino acid sequence of SEQ ID NOs:2-26, 31, 32, or 33. In one embodiment, the polypeptide has at least 75% identity to an amino acid sequence selected from the group consisting of SEQ ID NOs:2-26, 31, 32, and 33. In a preferred embodiment, the polypeptide has at least 75% identity, preferably 80%, 85%, 90%, 91%, 92%, 93%, 94%, 95%, 96%, 97%, 98%, 99% or 100% identity to a polypeptide selected from the group consisting of SEQ ID NOs:2-26, 31, 32, and 33.

The invention also provides a polypeptide having cholesterol efflux activity, where the polypeptide is a polypeptide having a sequence set forth in Example 2 in Table A, Table B, or Table C.

In some embodiments, the a peptide of the invention is linked, e.g., via a proline residue, to another amphipathic alpha helical peptide having cholesterol efflux activity. In some embodiments, a peptide of the invention is linked to a second peptide of the invention. The second peptide of the invention may be the same peptide, or a different peptide. Thus, the invention also provides a polypeptide having cholesterol efflux activity that comprises one or more peptides of the invention.

In one embodiment, the polypeptides of the present invention further comprise a protecting group. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. Thus, in one embodiment, the polypeptides of the present invention further comprise a protecting group coupled to the amino or carboxy terminus. In one embodiment, the polypeptides further comprise a first protecting group coupled to the amino terminus and a second protecting group coupled to the carboxyl terminus.

Suitable protecting groups include, but are not limited to, acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl—Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-butyl (tBu), and trifluoroacetyl (TFA).

In a preferred embodiment, the polypeptides comprise a first protecting group coupled to the amino terminus, the first protecting group including, but not limited to, acetyl, propionyl, and a 3 to 20 carbon alkyl. In a preferred embodiment, the first protecting group is an acetyl. In another preferred embodiment, the polypeptides comprise a second protecting group coupled to the carboxyl terminus, the second protecting being a amide.

The polypeptides of the present invention can comprise all "L" amino acids, all "D" amino acids or a mixture of "L" and "D" amino acids. It has surprisingly been found that polypeptides comprising all D-amino acids stimulate cholesterol efflux with high-capacity and high-affinity like the L-amino acid polypeptides.

Polypeptides of the invention have cholesterol efflux activity. In some embodiments, a polypeptide of the present invention has ABCA1 stabilizing activity. In one embodiment, a polypeptide of the present invention protects phospholipids from oxidation by an oxidizing agent (i.e., the polypeptide has anti-oxidant activity). In one embodiment, a polypeptide of the present invention has anti-inflammatory activity. In preferred embodiments, a polypeptide of the present invention comprises one or more of these activities. In even more preferred embodiments, a polypeptide of the present invention comprises each of these activities.

Peptides of the invention typically induce preβ-1 HDL formation in human plasma by binding/interacting with a distinct alpha-HDL particles, which is the majority of HDL particles in human plasma, and remodel the alpha-HDL particles to displace apoA-I, thereby producing pre-βHDL particles.

Further, the peptides of the invention are potent and induce preβ-1 and ABCA1-mediated cholesterol efflux at a molar ratio of peptide:apoA-I (in plasma) of 2:1, more typically at a molar ratio of 1:1; even more often at a ratio of 1:5 or 1:10, or lower.

A further embodiment of the invention provides pharmaceutical compositions comprising at least one polypeptide described herein and a pharmaceutically acceptable carrier or excipient. In some embodiments, the pharmaceutical compositions comprise an additional therapeutic agent (e.g., a statin such as atorvastatin, lovastatin, pravastatin, simvastatin, fluvastatin, or rosuvastatin; a bile acid binder such as cholestyramine or colestipol; a Nieman-Pick C1-Like 1 sterol transporter channel inhibitor such as Ezetimibe; a platelet clumping inhibitor such as aspirin, ticlopidine, or clopidogrel, niacin/nicotinamide, a PPAR activator, Vitamin E, or combinations thereof, for treating a disease or disorder associated with cholesterol efflux (e.g., cardiovascular disease).

Another aspect of the present invention provides peptidomimetics of the polypeptides disclosed herein. In one embodiment, the present invention provides a peptidomimetic having a substantially three-dimensional conformation as a polypeptide having an amino acid sequence of SEQ ID NO:1, SEQ ID NO:27, SEQ ID NO:28, SEQ ID NO:29, or SEQ ID NO:30. In another embodiment, the present invention provides a peptidomimetic having a substantially three-dimensional conformation as a polypeptide having an amino acid sequence selected from the group consisting of SEQ ID NOs:2-26, 31, 32, and 33. In one embodiment, the peptidomimetic is a retro-inverso analog. In another embodiment, the peptidomimetic is a retro-enantio analog. In yet another embodiment, the peptidomimetic is a trans-olefin analog. As disclosed herein, the peptidomimetics of the present invention can comprise other back-bone modifications. As with the polypeptides of the present invention, the peptidomimetics of the present invention can further comprise a protecting group and, preferably, a protecting group at both the amino and carboxyl termini.

In another aspect, the invention provides an amphipatic α-helical peptide that binds to the same ABCA1 binding site as a peptide that comprises one α-helical segment and has cholesterol efflux activity, e.g., a peptide selected from the group consisting of SEQ ID NO:1-33. The invention additionally provides an amphipatic α-helical peptide that binds to HDL. Furthermore, the invention further provides an isolated amphipatic α-helix peptide, e.g., that has a single 20 amino acid α-helix peptide element, and in some embodiments a 21 amino acid or 22 amino acid α-helix peptide element, that stimulates ABCA1-specific cholesterol efflux.

In a further aspect, the present invention provides a composition comprising a polypeptide of the present invention, such as a polypeptide having an amino acid sequence selected from the group consisting of SEQ ID NO:1-33, or a peptidomimetic thereof complexed with lipid. In one embodiment, the lipid is a phospholipid. In another embodiment, the phospholipids is 1-palmitoyl-2-oleoyl-sn-glycerol-3-phosphatidylcholine ("POPC"). In yet another embodiment, the composition further comprises a pharmaceutically acceptable carrier.

Yet another aspect of the invention provides methods of mediating cholesterol efflux in a mammalian subject (e.g., a primate such as a human or chimpanzee or a rodent such as a rat or mouse) by administering at least one polypeptide or peptidomimetic described herein to the subject. Those of skill in the art will appreciate that a nucleic acid encoding such a polypeptide (or peptidomimetic) can be administered to the subject in lieu of administering the polypeptide (or peptidomimetic). The present invention provides such nucleic acids. Based on their cholesterol efflux activity, the polypeptides and peptidomimetics of the present invention can be advantageously used to treat, ameliorate or prevent a disease or condition associated with dyslipidemia, hypercholesterolemia and inflammation.

In another aspect, the invention provides synthetic lipid particles, e.g., a synthetic LDL or HDL particle, for the delivery of therapeutic or diagnostic agents that comprise the polypeptides described herein, e.g., a polypeptide having a sequence selected from the group consisting of SEQ ID NO:1-33. Such particles can be used, e.g., to deliver therapeutic agents for the treatment of cancer or for the treatment of an infection.

Still another aspect of the present invention provides methods for treating or preventing a symptom of atherosclerosis in a mammal by administering at least one polypeptide or peptidomimetic described herein to the subject. Again, those of skill in the art will appreciate that a nucleic acid encoding such a polypeptide (or peptidomimetic) can be administered to the subject in lieu of administering the polypeptide (or peptidomimetic). Such nucleic acids are provided by the present invention. In one embodiment of this method, the mammal is a mammal diagnosed as having one or more symptoms of atherosclerosis. In another embodiment, the mammal is diagnosed as at risk for atherosclerosis. Preferably, the mammal is a human, but can also be a non-human animal. In one exemplary embodiment, the polypeptide has an amino acid sequence of SEQ ID NO:1, SEQ ID NO:27, SEQ ID NO:28, SEQ ID NO:29, or SEQ ID NO:30, or an amino acid sequence selected from the group consisting of SEQ ID NOs:2-26, 31, 32, and 33.

In another related embodiment, the methods further comprise administering at least one additional therapeutic agent. Examples of such therapeutic agents include, but are not limited to, an antibody, an enzyme inhibitor, an antibacterial agent, an antiviral agent, a steroid, a non-steroidal anti-inflammatory agent, an anti-metabolite, a cytokine, or a soluble cytokine receptor. The enzyme inhibitor may be a protease inhibitor or a cyclooxygenase inhibitor. The additional agent may be added as a part of a pharmaceutical composition, or may be administered concomitantly or within a time period when the physiological effect of the additional agent overlaps with the physiological effect of the polypeptide(s) or peptidomimetic(s) of the present invention. More specifically, an additional agent may be administered concomitantly or one week, several days, 24 hours, 8 hours, or immediately before the administration of the polypeptide(s) or peptidomimetic(s). Alternatively, an additional agent may be administered one week, several days, 24 hours, 8 hours, or immediately after the administration of the polypeptide(s) or peptidomimetic(s).

Yet another aspect of the present invention provides methods for stabilizing a vulnerable plaque, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having one or more vulnerable plaques. In another embodiment, the mammal is diagnosed as at risk for having a vulnerable plaque(s). Preferably, the mammal is a human, but can also be a non-human animal. In some embodiments, the polypeptide has an amino acid sequence of SEQ ID NO:1, SEQ ID NO:27, SEQ ID NO:28, SEQ ID NO:29, or SEQ ID NO:30. In some embodiments, the peptide has an amino acid sequence selected from the group consisting of SEQ ID NOs:2-26, 31, 32, and 33.

The present invention also provides kits for treating or preventing a disease or condition associated with dyslipidemia, hypercholesterolemia or inflammation. In a preferred embodiment, the present invention provides kits for treating or preventing a symptom of atherosclerosis, the kit comprising a container containing a polypeptide or peptidomimetic of the present invention. The kit can further comprise a pharmaceutically acceptable carrier. In addition, the kit can further comprise instructional materials teaching the use of the polypeptide or peptidomimetic for treating or preventing a disease or condition associated with dyslipidemia, hypercholesterolemia or inflammation, such as atherosclerosis. The polypeptides and peptidomimetics provided in the kits of the present invention can comprise all L amino acids, all D amino acids or a mixture of L and D amino acids.

In connection with the above kits, instructional material can include a document or recorded media including a written or audible instruction for the use of a pharmaceutical composition. Instruction material includes, for example, a label on a bottle, a paper inserted in a box, printing on the box or carton, instructions provided by a website at an address given in any of these locations, etc.

In another aspect, the present invention provides methods of making a variant polypeptide having cholesterol efflux activity and/or ABCA stabilization activity, the method comprising: (a) providing a parent polypeptide having an amino acid sequence of SEQ ID NO:1, SEQ ID NO:27, SEQ ID NO:28, SEQ ID NO:29, or SEQ ID NO:30 or having an amino acid sequence selected from the group consisting of SEQ ID NOs:2-26, 31, 32, and 33; (b) modifying at least one amino acid position of the polypeptide to generate a polypeptide variant; (c) screening the polypeptide variant for cholesterol efflux activity and/or ABCA stabilization activity; (d) selecting the polypeptide variant that has at least 80% of the cholesterol efflux activity of the parent polypeptide and/or selecting the polypeptide variant that has at least 80% of the ABCA stabilization activity of the parent polypeptide; and (e) synthesizing the selected polypeptide variant. In some embodiments, the polypeptide is modified, e.g., by substitution, deletion, or insertion of one, two, three, or more amino acids. For example, in some embodiments, a 22-mer can be modified to produce a 20-mer that has cholesterol efflux activity. In one embodiment, one or more of the amino acids is substituted with a conservative amino acid. The polypeptide can comprise one or more D amino acids. In some embodiments of this method, the modified or variant polypeptide comprises all D amino acids. In addition, to modifying one or more amino acids of the polypeptides, the backbone of the polypeptide can also be modified to make peptidomimetics as described herein.

In yet another aspect, the present invention provides use of at least one polypeptide or peptidomimetic of the present invention in the preparation of a medicament for mediating cholesterol efflux in a mammal. In exemplar embodiments, the polypeptide has an amino acid sequence selected from the group consisting of SEQ ID NO:1-33 or, alternatively, a peptidomimetic thereof. In one embodiment, the peptidomimetic has a substantially three-dimensional conformation as a polypeptide having an amino acid sequence selected from the group consisting of SEQ ID NO:1-33.

In a further aspect, the present invention provides use of at least one polypeptide or peptidomimetic of the present invention in the preparation of a medicament for treating a symptom of atherosclerosis in a mammal. In exemplar embodiments, the polypeptide has an amino acid sequence selected from the group consisting of SEQ ID NO:1-33 or, alternatively, a peptidomimetic thereof. In one embodiment, the peptidomimetic has a substantially three-dimensional conformation as a polypeptide having an amino acid sequence selected from the group consisting of SEQ ID NO:1-33.

In yet a further aspect, the present invention provides use of at least one polypeptide or peptidomimetic of the present invention in the preparation of a medicament for stabilizing a vulnerable plaque in a mammal. In exemplar embodiments, the polypeptide has an amino acid sequence selected from the group consisting of SEQ ID NO:1-33 or, alternatively, a peptidomimetic thereof. In one embodiment, the peptidomimetic has a substantially three-dimensional conformation as a polypeptide having an amino acid sequence selected from the group consisting of SEQ ID NO:1-33.

Another aspect of the invention provides an isolated nucleic acid encoding a polypeptide of the present invention, an expression vector comprising the nucleic acid, and a host cell comprising the expression vector.

A polypeptide and peptidomimetic of the invention is also useful as a research tool and/or diagnostic tool. For example, such a peptide can be used to identify subjects having reverse cholesterol deficient plasma and those subjects that are responders to reverse cholesterol treatment. Also, a polypeptide of the invention can be used to evaluate the anti-atherosclerotic potential of other compounds (including, e.g., peptidomimetics).

In addition, a polypeptide or peptidomimetic of the invention can be used for investigating lipoprotein-receptor interactions in animals and animal models, particularly when a polypeptide or peptidomimetic of the present invention is labeled (e.g., radioactive label, fluorescent label, etc.).

A polypeptide or peptidomimetic of the invention can also be used to identify appropriate animal models for elucidation of lipid metabolic pathways. For example, a polypeptide or peptidomimetic can be used to identify animal models and gene and/or drug interactions that have an effect on reverse cholesterol transport.

Other features, objects and advantages of the invention and its preferred embodiments will become apparent from a reading of the detailed description, examples, claims and figures that follow.

BRIEF DESCRIPTION OF THE DRAWINGS

FIG. 15 shows the percentage of cellular [$^3$H]cholesterol that appeared in the medium in response to treatment with the indicated peptides.

Figure 1:
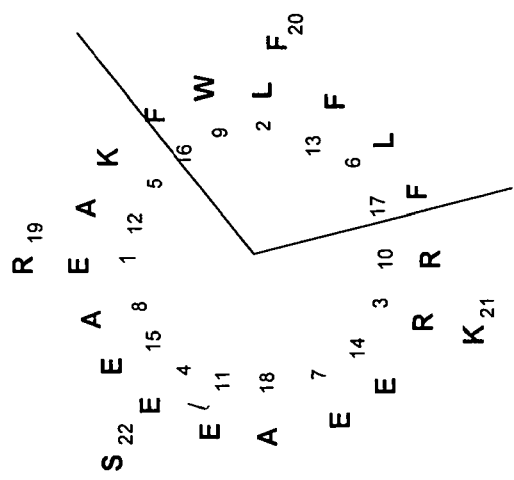
FIG. 1 shows a helical wheel diagram of peptide N257-11 (SEQ ID NO:34).

BRIEF DESCRIPTION OF EXEMPLARY
SEQUENCES OF THE INVENTION

| Postn[1] | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| SEQ ID NO: 1 is: |
| AA(s) | E | F | R | E | K | F | E | V | F | F | E | F | F | R | E | F | F | E | R | F |
|  | D | L | K | D | R | L | D | A | L | L | D | L | L | A | D | L | L | D | K | L |
|  |  | W | C | A | C | W |  | G | W | W | A | W | W | E |  | W | W | A | C | W |
|  |  | I |  | G |  | I |  |  | I | I | G | I | I | C |  | I | I | G |  | I |
|  |  | V |  |  |  | V |  |  | V | V |  | V | V |  |  | V | V |  |  | V |
|  |  | A |  |  |  | A |  |  | A | A |  | A | A |  |  | A | A |  |  | A |
| SEQ ID NO: 27 is: |
| AA(s) | E | L | R | E | K | F | E | A | F | F | E | F | F | R | E | F | F | E | R | F |
|  | D | I | K | D | R | L | D |  | L | L | D | L | L | E | D | L | L | D | K | L |
|  |  | V |  | A |  | I |  |  | W | I | A | I | I | A |  | I | I |  |  | I |
|  |  |  |  |  |  | W |  |  |  | W |  | W | W |  |  | W | W |  |  | W |
| SEQ ID NO: 28 is: |
| AA(s) | E | L | R | A | K | L | E | A | F | F | E | F | F | R | A | F | F | E | R | F |
|  | D |  |  |  | R |  | D |  | L | L | D | L | L |  |  | L | L | D |  | L |
|  |  |  |  |  |  |  |  |  | W |  |  |  |  |  |  |  |  |  |  |  |
| SEQ ID NO: 29 is: |
| AA(s) | E | L | R | E | K | L | E | A | F | F | E | F | F | R | E | F | F | E | R | F |
|  | D |  |  | D | R |  | D |  | L | L | D | L | L |  | D | L | L | D |  | L |
|  |  |  |  |  |  |  |  |  | W |  |  |  |  |  |  |  |  |  |  |  |
| SEQ ID NO: 30 is: |
| ELR(D/E)(K/R)LEA(W/F/L)(F/L)(D/E)L(F/L)RE(F/L)LER(F/L) |

In some embodiments, any of the peptides of SEQ ID NOs. 27-30 further comprise a position 21 that is C, K or L. In some embodiments, such a peptide further comprises a position 22, where position 22 is S or C. In some embodiments, the peptide further comprises positions 21 and 22 where position 21 is K and position 22 is S.

DETAILED DESCRIPTION OF THE INVENTION
AND PREFERRED EMBODIMENTS

I. Introduction

The present invention provides, inter alia, polypeptides that possess strong cholesterol efflux activity and ABCA stabilization activity. The polypeptides of the present invention have cholesterol efflux activity and ABCA1 stabilization activity that parallels that of the native apolipoproteins, such as Apo A-I and Apo E, which is extremely surprising in view of the fact that such polypeptides are non-naturally occurring. In some cases, the polypeptides of the present invention also possess an antioxidant activity and/or an anti-inflammatory activity.

Thus, the polypeptides of the present invention are unique in that they are small in size and possess an amino acid sequence not found in nature, while possessing activities similar in nature to the native apolipoproteins. Therefore, the polypeptides of the present invention are important biological tools for in vitro and in vivo studies of ABCA1 as well as important therapeutic agents for numerous therapeutic applications.

Preferred embodiments of such polypeptides are based on the sequences of SEQ ID NOS:1-33, as well as conservative variants thereof. In some embodiments, a polypeptide of the invention has the amino acid sequence SEQ ID NO:1, SEQ ID NO:27, 28, 29, or 30. In some embodiments, a polypeptide of the invention has the amino acid sequence of any one of SEQ ID NOs:2-26 and 31-33. The invention provides compositions comprising such polypeptides, methods of identifying, screening and synthesizing such polypeptides, and methods of treating, preventing, or diagnosing diseases and disorders associated with dyslipidemia, hypercholesterolemia and inflammation, such as, e.g., heart disease, atherosclerotic lesions, stroke, Alzheimer's (i.e., by ameliorating plaque deposition), and storage disorders by administering such polypeptides. The invention further provides kits for treating, preventing, or diagnosing diseases and disorders associated with dyslipidemia, hypercholesterolemia and inflammation as well as lipid storage disorders.

II. Definitions

The term "ABC" or "ATP Binding Cassette" refers to multidomain membrane proteins, responsible for the controlled efflux and influx of allocrites (e.g. cholesterol) across cellular membranes. ABC proteins comprise four domains, with two transmembrane domains (TMDs) responsible for allocrite binding and transport and two nucleotide-binding domains (NBDs) responsible for coupling the energy of ATP hydrolysis to conformational changes in the TMDs. The family members include, e.g., ABCA1 and ABCA7 (see, e.g., Dean et al., *J. Lipid Res.*, 42:1007-1017 (2001)). ABCA1 is characterized in Denis et al., *J Biol. Chem.*, 279(40):41529-36 (2004). ABCA1 plays a role in cholesterol efflux and is upregulated in cells that are exposed to cholesterol enriching conditions and is the defective molecule in Tangiers Disease (Brooks-Wilson et al., *Nat. Gen.*, 22:336-344 (1999); Bodzioch et al., *Nat. Gen.*, 22:347-351 (1999); Rust et al., *Nat. Gen.*, 22:352-355 (1999)). ABCA1 turns over rapidly and has a half life of about 1 hour in the absence of a suitable stabilizer, such as an apolipoprotein (see, e.g., Wang et al., *J. Clin. Invest.*, 111:99-107 (2003)) ABCA1 sequences are set forth in Genbank Accession Nos.: AJ012376; NM_173076; NM_015657; NM_005502; NP 005493; O95477. The promoter structure and genomic organization of the human ABCA7 gene is described in Broccardo et al., *Cytogenet Cell Genet.*, 92 (3-4): 264-70 (2001). ABCA7 sequences are set forth in Genbank Accession Nos.: NM_033308; NM_019112; NP_150651; NP_061985; AAK00959. A family of related ATP-binding proteins has been characterized (see, e.g., Higgins et al., *J Bioenerg Biomembr.*, 22(4):571-92 (1990); Higgins et al *Bioessay*, 8(4):111-6 (1988); Higgins et al., *Nature*, 323(6087):448-50 (1986); Doolittle et al., *Nature*, 323(6087):451-3 (1986); and Blight and Holland, *Mol. Microbiol.*, 4(6):873-80 (1990)). The proteins belonging to this family also contain one or two copies of the 'A' consensus sequence (see, e.g., Walker et al., *EMBO*, 1(8):945-51 (1982)) or the 'P-loop' (see, e.g., Saraste et al., *Trends Biochem Sci.*, 15(11):430-4 6155 (1990)). ABCA family members are reviewed in Broccardo et al., *Biochimica et Biophysica Acta*, 1461:395-404 (1999).

The term "amphipathic alpha helix" or "amphipathic α helix" refers to a polypeptide sequence that can adopt a secondary structure that is helical with one surface, i.e., face, being polar and comprised primarily of hydrophilic amino acids (e.g., Asp, Glu, Lys, Arg, His, Gly, Ser, Thr, Cys, Tyr, Asn and Gln), and the other surface being a nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Biophys. Chem.*, 16:561 (1987), and *Science*, 223:249 (1984)).

The polar face of an amphipathic α helix can, in some instances, display an "alignment of negatively charged amino acids" or "an alignment of acidic amino acids," i.e., a series of negatively charged or acidic amino acids (e.g., Asp and/or Glu) positioned approximately evenly (e.g., at about every one, two or three helical turns) within the polypeptide secondary structure. Amphipathic α helices play a role in both intra- and inter-molecular protein-protein interactions, and proteins and lipoproteins (e.g., including apolipoproteins) comprising amphipathic α helices have been postulated to play a role in lipid (e.g., HDL) transport and metabolism (see, e.g., Anantharamaiah et al., *Adv. Exp. Med. Biol.*, 285:131-40 (1991)). The structure and function of amphipathic α helices has been reviewed in, e.g., Segrest et al., *Proteins*, 8(2):103-17 (1990). In silico methods of identifying amphipathic α helices have been described by, e.g., Jones et al., *J. Lipid Res.*, 33(2):141-66 (1992). Multiple proteins comprising amphipathic α helices have been identified including, e.g., apolipoproteins and serum amyloid proteins.

A structure that is "substantially similar to a three-dimensional conformation" of a polypeptide of the invention refers to structure that comprises a core sequence, e.g., of 24 residues in length, that adopts an amphipathic α helix secondary structure that has an amphipathic orientation of amino acids along the axis of the α-helix structure, with one surface, i.e., face, being polar and comprised primarily of hydrophilic residues and the other surface being a nonpolar face that comprises primarily hydrophobic residues. Two separate acidic residue foci are present along the hydrophilic axis. A polypeptide or peptidomimetic that has a structure substantially similar to a three-dimensional conformation of a polypeptide of the invention also has the ability to stimulate ABCA1-mediated cholesterol efflux.

The term "apolipoprotein" or "Apo" or "exchangeable apolipoprotein" refers to any one of several water soluble proteins that combine with a lipid (i.e., solubilize the lipid) to form a lipoprotein and are constituents of chylomicrons, HDL, LDL and VLDL. Apolipoproteins exert their physiological effect on lipid metabolism by binding to and activating specific enzymes or lipid-transfer proteins or cell-surface receptors or ATP binding cassette transporters (e.g., ABC transporters). The interaction between apolipoproteins and ABCA1 produces cholesterol efflux and HDL particle assembly. Apolipoproteins include, e.g., Apo A-I, Apo A-II, Apo A-IV, Apo C-I, Apo C-II, Apo C-III, Apo E, and serum amyloid proteins such as, serum amyloid A.

The term "Apolipoprotein AI" or Apo A-I refers to a polypeptide comprising 243 amino acids forming N- and C-terminal domains (see, e.g., Saito et al., *J. Biol. Chem.*, 278:23227-23232 (2003) and Saito et al., *Prog. Lipid Res.*, 43:350-380 (2004)). The tertiary structure of apoA-I comprises an N-terminal four-helix bundle domain and a C-terminal domain that binds lipid strongly (see, e.g., Saito et al., *Prog. Lipid Res.*, 43:350-380 (2004) and Mishra et al., *Biochemistry*, 37:10313-10324 (1998)). Residues 44-243 of apoA-I contain the necessary structural determinants for mediating cholesterol efflux via ABCA1 (see, e.g., Chroni et al., *J. Biol. Chem.*, 278:6719-6730 (2003) and Natarajan et al., *J. Biol. Chem.*, 279:24044-24052 (2004)). This region of apoA-I (aa44-243) is comprised of a series of ten amphipathic α-helices of 11- and 22-amino acids separated by proline residues, as defined by exon 4 of the apoA-I gene (see, e.g., Borhani et al., *Proc. Natl. Acad. Sci.*, 94:12291-6 (1997)). The individual α-helical segments of apoA-I are defined, in part, by the relative distribution of positively charged residues and are designated as Class A or Y (see, e.g., Saito et al., *J. Biol. Chem.*, 278:23227-23232 (2003)). Class A helices possess positively charged amino acids at the lipid-water interface, while class Y helices exhibit a positively charged amino acid toward the middle of the polar surface in addition to interfacial cationic residues. The intact apoA-I molecule has been crystallized, along with a truncated form of the protein (A-I Δ1-43) (see, e.g., Ajees et al. *PNAS*, 103:2126-2131 (2006); Borhani et al., *Acta Crystallogr. D. Biol. Crystallogr.*, 55:1578-1583 (1999) and Segrest et al., *J. Biol. Chem.*, 274:31755-31758 (1999)). Apo AI sequences are set forth in, e.g., Genbank Accession Nos.: P02647, J0009; AAB64381; AAB22835; 1613168A; 1403292A; CAA25519; CAA26097; and LPHUA1.

Each of the amphipathic α-helices represented by aa 44-243 of apoA-I is theoretically capable of binding to phospholipid surfaces. Helices 1 (aa 44-65) and 10 (aa 220-241) of apoA-I possess the highest lipid-binding affinity in isolated form as synthetic 22-mer polypeptides (see, e.g., Gillotte et al., *J. Biol. Chem.*, 274:2021-2028 (1999)). As such, helices 1 and 10 have been implicated as mediators of cellular cholesterol efflux and nascent HDL assembly (Palgunachari et. al., *Arterioeler. Thromb. Vase. Biol.*, 16:328-338 (1996); Panagotopulos et. al., *J. Biol. Chem.*, 277:39477-39484 (2002); Chroni et al., *J. Biol. Chem.*, 278:6719-6730 (2003)). However, individual helices of apoA-I with high lipid-binding activity, such as helices 1 and 10, are not able to stimulate ABCA1-dependent cholesterol efflux (see e.g. Natarajan et al., *J. Biol. Chem.*, 279:24044-24052 (2004)). In nature, relatively long stretches of several apoA-I amphipathic α-helices arranged in series and joined end-to-end via proline residues are required for mediating productive ABCA1 interactions, i.e., cholesterol efflux and HDL assembly (see, Beckstead et al., *Biochem.* 44:4591-4599 (2005); Natarajan et al., *J. Biol. Chem.*, 279:24044-24052 (2004); Chroni et al. *J. Biol. Chem.*, 278:6719-6730 (2003) and Chroni et al., *Biochem.* 43:2126-2139 (2004)). The joining of apoA-I helices 9 with 10 creates a minimum element with activity in stimulating ABCA1 lipid efflux, although the activity of this minimum helix set is somewhat weaker than full-length apoA-I protein (see, Natarajan et al., *J. Biol. Chem.*, 279:24044-24052 (2004) and Vedhachalam et al. *J. Biol. Chem.*, 279:49931-49939 (2004)).

The term "Apolipoprotein E" or "Apo E" refers to a blood plasma protein that plays an important role in lipid homeostasis in the artery wall as well as in the brain (see, e.g., Wahrle et al., *J. Biol. Chem.*, 279:40987-40993 (2004)). Apo E is synthesized and secreted by macrophage foam-cells within atherosclerotic lesions where it functions to maintain cellular cholesterol homeostasis (see, e.g. Basu et al., *Proc. Natl. Acad. Sci. USA*, 78:7545-7549 (1981), Basu et al., *Science*, 219:871-873 (1983); Rosenfeld et al., *Arterioscler. Thromb.*, 13:1382-1389 (1993); O'Brien et al., *Am. J. Pathol.*, 144:538-548 (1994)) by reversing the macrophage foam-cell phenotype. These effects are related to the ability of apoE to stimulate cellular cholesterol efflux via ABCA1 as well as to its role in reverse cholesterol transport (Nara et al., *J. Biol. Chem.*, 266:3080-3086 (1991); Smith et al., *J. Biol. Chem.*, 271:30647-30655 (1996); Oram et al., *J. Lipid Res.*, 37:2473-2491 (1996); Zhang et al., *J. Biol. Chem.*, 271:28641-28646 (1996); Remaley et al., *Biochem. Biophys. Res. Comm.*, 280:818-823 (2001), and Mahley, *Science*, 240:622-630 (1988)). ApoE can compete with apoA-I for binding to ABCA1 expressing cells and it can form a molecular complex with ABCA1 (Krimbou et al., *J. Lipid Res.*, 45:839-848 (2004)). Defective Apo E/ABCA1 interactions in the brain dramatically reduce extracellular Apo E levels and interfere with intercellular lipid transport contributing to the development of neurological disorders (see, e.g., Hirsch-Reinshagen et al., *J. Biol. Chem.*, 279:41197-41207 (2004); Wahrle et al., *J. Biol. Chem.*, 279:40987-40993 (2004) and Koldamavo et al., *J. Biol. Chem.*, 280:43224-43235 (2005)).

The apoE protein is composed of an N-terminal four-helix bundle domain and C-terminal helices, which is similar to apoA-I (Saito et al., *Prog. Lipid Res.*, 43:350-380 (2004); Saito et al., *J. Biol. Chem.*, 278:23227-23232 (2003); Ajees et al., *Proc. Natl. Acad. Sci. USA*, 103:2128-2131 (2006)). The C-terminal domain of apoE is composed of two long helical segments separated by a proline residue (see, e.g., Hatters et al., *Trends Biochem. Sci.*, 416, in press, www.sciencedirect-.com(2006); Weisgraber, *Adv. Prot. Chem.*, 45:249-302 (1994); Saito et al., *J. Biol. Chem.*, 278:23227-23232 (2003)). The first segment consists of 51 amino acids (residues 216-266) forming a class A α-helix and the second 33 amino acids (aa 267-299) that is a class G α-helix (Segrest et al., *J. Lipid Res.*, 33:141-165). Both helical segments comprising approximately 79 amino acids (residues 222-299) of the apoE CT domain are required for mediating ABCA1 lipid efflux and HDL assembly efficiently (Vedhachalam et. al., *J. Biol. Chem.*, 279(48):49931-49939 (2004)). Therefore, as is the case with Apo A-I, nature relies on relatively long stretches of multiple helical segments linked in series to elicit ABCA1-interactions and ABCA1-cellular cholesterol efflux (Vedhachalam et. al., supra). Apo E sequences are set forth in Genbank Accession Nos.: NM_000041; P02649; AAH03557; AAB59397; and AAB59518.

The terms "cholesterol efflux" and "cholesterol efflux activity" refer to efflux of cholesterol from any cell type. For example, macrophage foam-cells in the artery wall release (i.e., export) cholesterol to appropriate acceptors, such as apolipoproteins and/or HDL. A compound that mediates cholesterol efflux enhances the release, i.e., movement, of cholesterol out of the cell and into the extracellular medium or compartment. Cholesterol efflux is often accompanied by or preceded by, i.e., follows, the efflux of phospholipids from cells. The coordinated release of both cholesterol and phospholipids produces HDL in the presence of a suitable lipid acceptor, e.g., apolipoprotein or peptide. Therefore, the processes of cholesterol- and phospholipid-efflux are linked and synonymous with one another. A compound that enhances the release of cholesterol from cells increases the amount of cholesterol and/or phospholipids appearing outside the cell by at least 25%, 50%, 75%, 100% or by at least 2-fold, 4-fold, 8-fold, 10-fold or more compared to the level of cholesterol efflux in the absence of the compound.

The term "ABCA stabilization activity" or "ABCA1 stabilization" refers to enhancing and/or extending the half life of an ABCA protein by preventing its degradation. A compound that has ABCA1 stabilization activity will significantly delay the proteins degradation. This will produce an increase in cellular ABCA1 protein levels of at least 25%, 50%, 75%, 100% or at least 2-fold, 4-fold, 8-fold, 10-fold or higher compared to ABCA1 protein detected in the absence of the compound.

The term "anti-inflammatory activity" refers to prevention or reduction of inflammation. Inflammation will be recognized as playing a role in atherosclerosis development and associated with dyslipidemia, hypercholesterolemia and/or lipoprotein lipid oxidation. The inflammatory response can be local, such as in the artery wall or brain or other extravascular tissues, and systemic. Both local- and systemic-inflammation can be associated with generation of inflammatory mediators, such as oxidized lipids and/or cytokines. In general, the inflammatory response is associated with recruitment of blood monocyte-macrophages into extra-vascular compartments. The recruitment of monocyte-macrophages is associated with macrophage activation, differentiation and retention in the extra-vascular tissues. A compound that has anti-inflammatory activity will decrease an inflammatory response as measured by a decrease in inflammatory mediators (e.g., adhesion molecules, cytokines and/or oxidized lipids) and/or a decrease in macrophages and/or macrophage activation in plaques and tissues, compared to in the absence of the compound.

The term "antioxidant activity" refers to prevention or reduction of oxidation caused by reactive oxygen species (ROS) including, e.g., hydrogen peroxide ($H_2O_2$); hypochlorite ion (—OCl); hydroxyl radical (—OH); and the superoxide anion ($O_2$—). A number of naturally occurring substances (e.g., proteins and small molecules) possess antioxidant activity. For example, apolipoproteins can inhibit lipid peroxidation, thus protecting phospholipid surfaces from lipophilic, as well as, water soluble free radical initiators (see, e.g., *Biochemistry*, 41:2089-2096 (2002)). In addition, alpha-tocopherol (vitamin E) is an antioxidant. Moreover, proteins and peptides that promote the movement of oxidants, such as oxysterols and oxidized phospholipids, and antioxidants (vitamin E) in and out of cells via ABC transporters or any other means can be viewed as having anti-oxidant activity, to rid the artery wall of inflammatory mediators and/or affect restoration of a favorable redox balance in tissues. A compound with an antioxidant activity, has an antioxidant activity that is at least 25%, 50%, 75%, 100% or at least 2-fold, 4-fold, 8-fold, 10-fold or more higher than the antioxidant activity in the absence of the compound.

"Plaque stabilization," as used herein, refers to the stabilization of vulnerable plaques from risk of rupture or erosion by removing cholesterol from lipid rich plaques, including but not limited to, removal of cholesterol from foam cell macrophages. Plaques contain thrombogenic substances, i.e., substances that when exposed to plasma are very powerful in aggregating platelets with the risk of local thrombosis and vessel occlusion, such as tissue factor. The rupture of the plaque and exposure of such material is prevented by the fibrous cap separating the plaque from the vessel. Lipid removal confers plaque stability in two main ways. Firstly, anatomically, lipid removal by shrinking the gruel in the artery is conferring plaque stability by decreasing the risk of hemodynamical stress (expansion-contraction associated with heart beats and blood pressure changes). Secondly, as described in the literature, cholesterol accumulation is stimulating the synthesis and secretion of proteases, including matrix-metallo-proteinases (MMPs) having lysis effects on the fibrous cap; and production of tissue factor, a potent clotting factor.

"Reverse Cholesterol Transport (RCT)," as used herein, refers to the process of removing cholesterol from macrophage foam cells and the lipid rich plaque from the arterial wall, with subsequent transfer through plasma to the liver for uptake, processing and excretion as neutral sterols (cholesterol) or acidic sterols (hydroxylated cholesterol/bile) in feces. The efflux of cholesterol from macrophage foam cells is a requirement for RCT benefit in itself even though the cholesterol may be shifted to other less vulnerable adjacent cells. However, the further disposal of such cholesterol by transport in HDL-like particles to the liver for excretion is a favorable aspect of treatment. Such complete RCT provide a general rejuvenation of the arterial tree by actual net removal of the cholesterol content in the arteries. The RCT and plaque stabilizing effects are either conferred directly by the peptides, or the complexes that they naturally form with phospholipids in plasma and cells or, alternatively, apoA-I/HDL as the peptides bind to endogenous HDL particles, thereby changing their properties and making them more efficient to promote RCT.

The term "pre-β formation" in the context of this invention refers to formation of pre-β-HDL particles. Pre-β-HDL are lipid-poor particles comprising ApoA-I molecules, typically 2-3 ApoA-I molecules, and small amounts of phospholipids. Pre-β-HDL particles act as initial acceptors of cellular cholesterol efflux and/or mediate ABCA1 cholesterol efflux.

A disease or disorder associated with "dyslipidemia" is any disease or disorder in which lipid metabolism is disregulated, due to alterations in tissue (i.e., blood) lipids and lipoprotein concentrations and/or aberrant mediation of cholesterol efflux or aberrant ABCA stabilization. Such diseases include, for example, heart disease, atherosclerotic lesions, stroke, Alzheimer's, and storage disorders.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. A more detailed description of amino acid as well as conservative amino acid substitutions is provided below in the section entitled "Polypeptides."

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as an amino acid sequence of SEQ ID NO:2-26, 31, 32, or 33) or the first 20 amino acids of those sequences that are 21 or 22 amino acids in length, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes,* 8:91-98 (1994)). The term nucleic acid is used interchangeably with gene, cDNA, mRNA, oligonucleotide, and polynucleotide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the polypeptide, and used to detect antibodies specifically reactive with the polypeptide).

As used herein, "ameliorates" means alleviate, lessen, or decrease the extent of a symptom or decrease the number of occurrences of episodes of a disease manifestation.

The term "preventing" is art-recognized, and when used in relation to a condition, such as recurrence or onset of a disease such as hypercholesterolemia or atherosclerosis, is well understood in the art, and includes administration of a composition which reduces the frequency of, or delays the onset of, symptoms of a medical condition in a subject relative to a subject which does not receive the composition.

As used herein, "treating" means either slowing, stopping or reversing the progression of the disorder or disease. In a preferred embodiment, "treating" means reversing the progression to the point of eliminating the disorder or disease.

As used herein, "inhibits" means that the amount is reduced as compared with the amount that would occur in a control sample. In a preferred embodiment, inhibits means that the amount is reduced by more than 50%, even more preferably by more than 75% or even 100%.

A "subject," "patient" or "mammal" to be treated by the methods disclosed herein can mean either a human or non-human animal.

III. Polypeptides

The present invention provides a family of non-naturally occurring polypeptides that use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-oxidant activity as well as anti-inflammatory activity, any combination of these activities and, preferably, all of these activities.

The peptides of the invention are based on the surprising discovery of a core amino acid sequence, SEQ ID NO:1, that has an effect on cholesterol efflux. The polypeptides of the present invention are non-naturally occurring polypeptides, e.g., SEQ ID NOs. 2-26 and 31-33, that stimulate ABCA1-dependent cholesterol efflux with a molar potency similar to that of apolipoproteins (e.g., Apo A-I, Apo E, etc.). Interestingly, the polypeptide family members of the present invention are small in size, corresponding to a single helical segment that captures the full biological activity and potency of intact apolipoproteins and the long stretches of multiple α-helical segments found in nature that are required to exert cholesterol efflux activity via ABCA1.

Regarding amphipathic α-helix peptides, hydrophobic amino acids are concentrated on one side of the helix, usually with polar or hydrophilic amino acids on the other. This arrangement is common in alpha helices of apolipoproteins and globular proteins, where one face of the helix is oriented toward the hydrophobic core and one face is oriented toward the water-exposed surface. Different amino-acid sequences have different propensities for forming α-helical structure. Methionine, alanine, leucine, glutamate, and lysine all have especially high helix-forming propensities, whereas proline, glycine, tyrosine, and serine have relatively poor helix-forming propensities.

In one embodiment, the present invention provides an isolated polypeptide (and compositions comprising such peptides) comprising an amino acid sequence of SEQ ID NO:1. In some embodiments, the present invention provides an isolated polypeptide comprising the following amino acid sequence $X_1X_2X_3X_4X_5X_6X_7AX_9X_{10}X_{11}$, $X_{12}X_{13}$, $X_{14}X_{15}X_{16}X_{17}X_{18}X_{19}X_{20}$ (SEQ ID NO:27) wherein $X_1$, $X_7$, $X_{15}$, and $X_{18}$ are independently selected from the group consisting of D and E; $X_2$ is L, I, or V; $X_4$ and $X_{11}$ are independently selected from the group consisting of D, E, and A; $X_3$, $X_5$ and $X_{19}$ are independently selected from the group consisting of K and R; $X_9$ is W, F or L; $X_{14}$ is R, E, or A; and $X_6$, $X_{10}$, $X_{12}$, $X_{13}$, $X_{16}$, $X_{17}$, and $X_{20}$ are independently selected from the group consisting of F, L, I, and W.

In one embodiment, the isolated polypeptide comprises (and, in certain embodiments, consists of or, alternatively, consists essentially of) an amino acid sequence selected from the group consisting of SEQ ID NOs. 1-33.

In some embodiments, a peptide of the invention comprises a peptide having the amino acid sequence set forth in SEQ ID NO:2, or variants thereof having one or more of the following substitutions: a L or F substituted for the W at position 9; V substitutions for L on the non-polar surface, e.g., a V substitution for L at position 2; L or I substitutions for F residues on the nonpolar surface at positions 10, 13, 16, and/or 20; F or I substitutions for L residues at positions 2, 6, 12, and/or 17; R substitutions for K, e.g., at position 5; aspartic acid substitutions for one or more glutamic acid residues in SEQ ID NO:2; a W substitution for L at position 12; A substitutions on the polar surface, for example A substitutions for R at position 14, E at position 4, E at position 11 and/or E at position 18. In some embodiments, SEQ ID NO:2 or such variants may further comprise the residues KS added to the C-terminus. Thus, in some embodiments, variants of SEQ ID NO:2 have A residues on the polar surface; but not on the non-polar surface. In some embodiments, the non-polar surface can be increased by including the highly hydrophobic L or F at positions 12, 17 and 21, which are located at or near the lipid-water interface, to maximize hydrophobic surface.

It will be readily understood by those of skill in the art that the foregoing polypeptides are not fully inclusive of the family of polypeptides of the present invention. In fact, using the teachings provided herein, other suitable polypeptides (e.g., conservative variants) can be routinely produced by, for example, conservative or semi-conservative substitutions (e.g., D replaced by E), extensions, deletions and the like. In addition, using the assays provided herein, other suitable polypeptides can be routinely screened for desired biological activities.

Thus, in another embodiment, the present invention provides polypeptide variants of the polypeptides of SEQ ID NOS:2-26 and 31-33. In one exemplary embodiment, the polypeptides have at least 75%, at least 80%, at least 85%, at least 90%, at least 95% or at least 98% identity to the polypeptides of a polypeptide selected from the group consisting of SEQ ID NO:2-26, 31, 32, and 33. As will be appreciated by those of skill in the art, non-identical amino acid residues can be naturally or non-naturally occurring. The term "percent identical" refers to sequence identity between two amino acid sequences (or between two nucleotide sequences, which are also provided by the present invention). Identity can each be determined by comparing a position in each sequence that may be aligned for purposes of comparison. When an equivalent position in the compared sequences is occupied by the same amino acid or base, then the molecules are identical at that position; when the equivalent site is occupied by the same or a similar amino acid residue (e.g., similar in steric and/or electronic nature), then the molecules can be referred to as homologous (similar) at that position. Expression as a percentage of homology, i.e., similarity, or identity refers to a function of the number of similar or identical amino acids at positions shared by the compared sequences. Various alignment algorithms and/or programs can be used, including, for example, FASTA, BLAST and ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

In another embodiments, which can overlap with the embodiments described above, the polypeptides of SEQ ID NO:2-26 and 31-33 are substituted with conservative (or semi-conservative) amino acid residues. The term "conservative amino acid substitutions" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr.

In another exemplary embodiment, which again can overlap with the embodiments described above, "a conservative amino acid substitution" can refer to the substitution of an amino acid for another that is similar in molecular weight or similar in hydrophobicity. By "similar molecular weight" and "similar hyrdrophobicity" is meant a value that is within 25%, more preferably 20%, 15%, 10%, or less than 10% of the respective value. Data for amino acid molecular weights and hydrophobicities are set forth in Table 1. A hydrophobicity ranking is set forth in Table 2; a conservative substitution includes exchanging an amino acid that is designated "=" to another (e.g., Tyr=Trp) and exchanging one amino acid for another that is adjacent to it in the ranking order as delineated by the greater and lesser than symbols.

TABLE 1

Parameters for the Unmodified Physiological L-alpha-Amino Acids

| Amino Acid | 3-Letter Code | 1-Letter Code | Molecular Weight[†] | Hydrophobicity[‡] |
|---|---|---|---|---|
| Alanine | Ala | A | 89.09 | 0.616 |
| Cysteine | Cys | C | 121.16 | 0.680 |
| Aspartate | Asp | D | 133.10 | 0.028 |
| Glutamate | Glu | E | 147.13 | 0.043 |
| Phenylalanine | Phe | F | 165.19 | 1.00 |
| Glycine | Gly | G | 75.07 | 0.501 |
| Histidine | His | H | 155.16 | 0.165 |
| Isoleucine | Ile | I | 131.18 | 0.943 |
| Lysine | Lys | K | 146.19 | 0.283 |
| Leucine | Leu | L | 131.18 | 0.943 |
| Methionine | Met | M | 149.21 | 0.738 |
| Asparagine | Asn | N | 132.12 | 0.236 |
| Proline | Pro | P | 115.13 | 0.711 |
| Glutamine | Gln | Q | 146.15 | 0.251 |
| Arginine | Arg | R | 174.20 | 0.000 |
| Serine | Ser | S | 105.09 | 0.359 |
| Threonine | The | T | 119.12 | 0.450 |
| Valine | Val | V | 117.15 | 0.825 |
| Tryptophan | Trp | W | 204.23 | 0.878 |
| Tyrosine | Tyr | Y | 181.19 | 0.880 |

[†]The molecular weights given are those of the neutral, free ammo acids; residue weights can be obtained by subtraction of one equivalent of water (18 g/mol).
[‡]The hydrophobicities given are the "Scaled" values from computational log(P) determinations by the "Small Fragment Approach" (see, *"Development of Hydrophobicity Parameters to Analyze Proteins Which Bear Post- or Cotranslational Modifications"* Black, S. D. and Mould, D. R., *Anal Biochem.*, 193: 72-82 (1991)). The equation used to scale raw log(P) values to the scaled values given is as follows: Scaled Parameters = (Raw Parameters + 2.061)/4.484.

TABLE 2

Trend of Hydrophobicity Parameters for the Physiological L-alpha-Ammo Acids

Phe > Leu = Ile > Tyr = Trp > Val > Met > Pro > Cys > Ala > Gly > Thr > Ser > Lys > Gln > Asn > His > Glu > Asp > Arg

Aspartic acid and glutamic acid are acidic, providing a negative charge at physiological pH; and histidine, arginine and lysine are basic, providing a positive charge at physiological pH.

Another indication that two polypeptides are conservative variants of one another is that the two polypeptides carry out the same function and, in preferred embodiments, the same function at the same or very similar level of activity. Thus, in some embodiment, a conservative variant of a polypeptide of this invention will comprise an activity of at least 80%, 85%, 86%, 87%, 88%, 89%, 90%, 91%, 92%, 93%, 94%, 95%, 96%, 97%, 98%, 99%, or 100% of that found in a polypeptide of SEQ ID NO:1, 27, 28, 29, or 30; or, more particularly, to that found in a polypeptide selected from the group consisting of SEQ ID NOs:2-26 and 31-33. Again, in some embodiments, the polypeptides of this invention will possess more than one activity. For example, a polypeptide of the invention can comprise cholesterol efflux mediating activity, ABCA stabilization activity, anti-inflammatory activity as well as antioxidant activity, any combination of these activities or, ideally, all of these activities. Conservative variants can have one or more of the same activities and, ideally, all of the same activities. The screening assays described herein can be readily used by those of skill in the art to determine whether two or more polypeptides possess similar activities. In addition, those of skill in the art will know of other screening assays that can be used to determine whether two or more polypeptides possess similar biological properties or activities.

While in preferred embodiments, the polypeptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) can be used in the polypeptides of the present invention. As with the other amino acid substitutions, non-naturally occurring amino acids are typically substituted so that, upon substitution, they retain the spatial and ionic or non-ionic character of the residue that they substitute.

One of skill understands that amino acid residues may be added to either the C-terminus and/or N-terminus of the polypeptides of the present invention without effecting the activity of such polypeptides. Thus, a polypeptide of the invention that comprises α helical sequence as described herein (e.g., a polypeptide of SEQ ID NO:1-33), includes embodiments that are over 20, 21, or 22 amino acids in length, e.g., peptide that are 23, 24, 25, 26, 27, 30, 35, or 40 amino acids in length. One of skill also understands that polypeptides of the invention that in one embodiment, a polypeptide of the invention is linked, e.g., via a proline or other linker residues, to another amphipathic α helical peptide that can stimulate cholesterol efflux to form a bi-helix or multimer polypeptide, e.g., of 40, 50, 60, 70, 80, 90, or 100 amino acids in length. Accordingly, a sequence of any of SEQ ID NOs. 1-33 can have amino acid additions or can be joined. For example, one molecule of a polypeptide of the invention, e.g., SEQ ID NO: 2-26 or 31-33, may be joined to another molecule of the polypeptide through a proline residue to provide a polypeptide that is at least 41 amino acids in length. Similarly, two 20-mers, two 21-mers, two 22-mers, a 20-mer and a 22-mer, a 21-mer and 20-mer or a 21-mer and 22-mer can be joined e.g., using a proline, thereby resulting in a polypeptide that is 41-45 residues in length. Such a bi-helix or multimer peptide has activity that is equivalent to, or preferably, exceeds, the activity of a single-helix peptide of the invention comprised by the bi-helix or multimer peptide. Further, such a bi-helix or multimer polypeptide can have cholesterol efflux activity that exceeds that of a native full-length apolipoproteins (e.g., Apo AI and Apo E), or that of the cholesterol efflux-mediating domain of the apolipoprotein. Using the methodologies described herein, one of skill can readily add additional amino acids to either the C-terminus and/or N-terminus, and then screen the resulting polypeptides for the desired activity.

In some embodiments, α helix peptide as described herein may be modified by substituting or inserting a thiol-bearing amino acid (e.g., Cys) at the polar/nonpolar interface of the helix.

In a particularly preferred embodiment, the polypeptides of the present invention comprise one or more D-amino acids as described herein. In certain embodiments, every amino acid (e.g., every enantiomeric amino acid) is a D-amino acid. It has been found that polypeptides comprising all D-amino acids stimulate cholesterol efflux with high-capacity and high-affinity like the L-amino acid polypeptides. D-amino acids are readily incorporated at one or more positions in the polypeptide simply by using a D-form derivatized amino acid residue in the chemical synthesis. D-form residues for solid phase polypeptide synthesis are commercially available from a number of suppliers (see, e.g., Advanced Chem Tech, Louisville, Ky.; Nova Biochem, San Diego, Calif.; Sigma, St Louis, Mo.; Bachem California Inc., Torrance, Calif., etc.). The D-form amino acids can be incorporated at any position in the polypeptide as desired. Thus, for example, in one embodiment, the polypeptide can comprise a single D-amino acid, while in other embodiments, the polypeptide comprises at least two, generally at least three, more generally at least four, most generally at least five, preferably at least six, more preferably at least seven and most preferably at least eight D amino acids. In one embodiment, essentially every other (enantiomeric) amino acid is a D-form amino acid. In certain embodiments, at least 80%, preferably at least 90%, more preferably at least 95% of the enantiomeric amino acids are D-form amino acids. In one particularly preferred embodiment, essentially every enantiomeric amino acid is a D-form amino acid.

In yet another embodiment, peptidomimetics of the polypeptides of the present invention are provided. A "peptidomimetic" includes any modified form of an amino acid chain, including, but not limited to, phosphorylation, capping, fatty acid modifications and including unnatural backbone and/or side chain structures. It will be readily apparent to those of skill in the art that a peptidomimetic comprises the structural continuum between an amino acid chain and a non-peptide small molecule. Peptidomimetics generally retain a recognizable polypeptide-like polymer unit structure. Thus, a peptidomimetic typically retains the function of binding to any target molecule that a natural polypeptide binds to. Examples of suitable peptidomimetics are disclosed in U.S. Patent Application Publication No. 2006/0069030, the teachings of which are incorporated by reference for all purposes. Other peptidomimetics and methods of making same will be known to those of skill in the art.

In preferred embodiments, the peptidomimetics of the present invention fall into one of two categories: (i) surrogates; and (ii) analogs. Numerous surrogates have been developed for the amide bond of polypeptides. Frequently exploited surrogates for the amide bond include, but are not limited to, the following groups: (i) trans-olefins, (ii) fluoroalkene, (iii) methyleneamino, (iv) phosphonamides, and (v) sulfonamides. Examples of such surrogates are disclosed in U.S. Patent Application Publication No. 2006/0069030. Additionally, peptidomimetics based on more substantial modifications of the backbone of a polypeptide can be used. Peptidomimetics that fall in this category include (i) retro-inverso analogs, and (ii) N-alkyl glycine analogs (so-called peptoids). Again, examples of such analogs are disclosed in U.S. Patent Application Publication No. 2006/0069030.

In one embodiment of the present invention, the peptide or peptidomimetic is a retro-inverso analog. Retro-inverso analogs can be made according to the methods known in the art, in a manner similar to synthesizing L-amino acid based polypeptides. More specifically, examples of methods suitable for preparing such retro-inverso analogs are described in U.S. Pat. No. 4,522,752, which issued to Sisto et al. The final product, or intermediates thereof, can be purified by HPLC or any other suitable chromatographic method known to those of skill in the art.

In another embodiment, the peptide or peptidomimetic is a retro-enantio analog. Retro-enantio analogs can be synthesized from commercially available D-amino acids (or analogs thereof) using standard solid- or solution-phase polypeptide-synthesis techniques.

In still another embodiment, the peptidomimetic is a trans-olefin analog or derivative. Such trans-olefin analogs of a polypeptide can be readily synthesized according to the method of Shue et al., *Tetrahedron Lett.*, 28:3225 (1987). In addition, other methods known in the art can also be used. It will be appreciated that variations in the procedure of Sjue et al., or other procedures available, may be necessary depending on the nature of the reagents used in synthesizing the trans-olefin derivative.

It is also possible to couple the pseudodipeptides synthesized by the above method to other pseudodipeptides, to make pseudopeptides with several olefinic functionalities in place of amide functionalities. For example, pseudodipeptides corresponding to certain di-peptide sequences can be made and then coupled together by standard techniques to yield an analog of the polypeptide that has alternating olefinic bonds between residues.

Still another class of peptidomimetic derivatives includes phosphonate derivatives. The synthesis of such phosphonate derivatives can be adapted from known synthesis schemes (see, for example, Loots et al. in "Peptides: Chemistry and Biology," (Escom Science Publishers, Leiden, p. 118, 1988); Petrillo et al. in "Peptides: Structure and Function (Proceedings of the 9th American Peptide Symposium)," (Pierce Chemical Co. Rockland, Ill., 1985).

In other embodiments, the modification can be the introduction of carbohydrate or lipid moieties. Such modifications can change the solubility of the polypeptides in various mediums so that they can advantageously be prepared as a suitable pharmaceutical composition. Modifying lipid groups include, but are not limited to, farnesyl groups and myristoyl groups. Modifying carbohydrate groups include, but are not limited to, single sugars or oligosaccharides of any naturally occurring and/or synthetic sugar and sugar alcohols including, for example, glucose, galactose, rhamnose, mannose, arabinose, and other sugars, and their respective alcohols.

In certain embodiments, the peptidomimetics of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or mono-saccharide, and phosphates. Effects of such non-amino acid elements on the functionality of a peptidomimetic can be tested using the assay methods disclosed herein.

Thus, in a preferred embodiment, the peptidomimetics of the present invention have a three-dimensional conformation that is substantially similar to a polypeptide of SEQ ID NO:1-33. In particular embodiments, the peptidomimetics include at least one backbone linkage that is not an amide linkage in the amino to carboxy direction, such as a retro-inverso polypeptide relative to a naturally-occurring polypeptide, or at least one backbone linkage that is not an amide linkage.

The polypeptides as well as the peptidomimetics of the present invention, including, for example, the retro-inverso peptidomimetics, can be modified so that the R-groups on the constituent amino acids and/or the terminal amino acids are blocked, i.e., protected, by a protecting group. It has been found that blockage, particularly of the amino and/or carboxy termini, greatly improves oral delivery and significantly increases serum half-life. As used herein, "protecting group" refers to a temporary substituent that protects a potentially reactive functional group from undesired chemical transformations. Examples of such protecting groups generally include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

A wide number of protecting groups are suitable for this purpose. Such groups include, but are not limited to, acetyl, $CH_3$—$(CH_2)_n$—CO—, amide, Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3, 6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl—Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), and Trifluoroacetyl (TFA). The variable "n" is an integer from 0 to 12, typically 0 to 6 such as 0 to 4. Other suitable protecting groups are disclosed in U.S. Pat. No. 6,933,279, the teachings of which are incorporated by reference.

In one embodiment, preferred protecting groups include, but are not limited to, acetyl, amide, and alkyl groups with acetyl and alkyl groups being particularly preferred for N-terminal protection and amide groups being particularly preferred for carboxyl terminal protection. In one preferred embodiment, an acetyl group is used to protect the amino terminus and an amide group is used to protect the carboxyl terminus. In this embodiment, acetylation can be accomplished during the synthesis when the polypeptide is on the resin using acetic anhydride. Amide protection can be achieved by the selection of a proper resin for the synthesis. For instance, a rink amide resin can be used. After the completion of the synthesis, the semipermanent protecting groups on acidic bifunctional amino acids, such as Asp and Glu, and basic amino acids, such as Lys, as well as the hydroxyl of Tyr, are all simultaneously removed. The polypeptides released from such a resin using acidic treatment comes out with the N-terminal protected as acetyl and the C-terminal protected as $NH_2$, with the simultaneous removal of all of the other protecting groups.

A. Chemical Synthesis

The polypeptides can be chemically synthesized using methods well known in the art including, e.g., solid phase synthesis (see, e.g., Merrifield, *J. Am. Chem. Soc.*, 85:2149-2154 (1963) and Abelson et al., Methods in Enzymology, Volume 289: Solid-Phase Peptide Synthesis (1st ed. 1997)). Polypeptide synthesis can be performed using manual techniques or by automation. Automated synthesis can be achieved, for example, using Applied Biosystems 431A Peptide Synthesizer (Perkin Elmer). Alternatively, various fragments of the polypeptide can be chemically synthesized separately and then combined using chemical methods to produce the full length polypeptide. The sequence and mass of the polypeptides can be verified by GC mass spectroscopy. Once synthesized, the polypeptides can be modified, for example, by N-terminal acetyl- and C-terminal amide-groups as described above. Synthesized polypeptides can be further isolated by HPLC to a purity of at least about 80%, preferably 90%, and more preferably 95%.

B. Recombinant Expression

The polypeptides described herein can also be expressed recombinantly, especially when the polypeptide does not comprise a "D" amino acid residues. This embodiment relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

Polymerase chain reaction or other in vitro amplification methods may also be useful, for example, to clone nucleic acid sequences that code for the polypeptides to be expressed, to make nucleic acids to use as probes for detecting the presence of encoding mRNA in physiological samples, for nucleic acid sequencing, or for other purposes. Nucleic acids amplified by the PCR reaction can be purified from agarose gels and cloned into an appropriate vector.

Gene expression of a sequence of the invention can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

To obtain high level expression of a nucleic acid sequence, such as the nucleic acid sequences encoding a polypeptide of this invention, one typically subclones a nucleic acid sequence that encodes a polypeptide sequence of the invention into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding a polypeptide of the invention or a subsequence thereof. Suitable bacterial promoters are well known in the art and described, e.g., in Sambrook et al. and Ausubel et al. The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant polypeptides to provide convenient methods of isolation, e.g., His tags. In some case, enzymatic cleavage sequences (e.g., Met-(His)-Ile-Glu-Gly-Arg (SEQ ID NO:62) which form the Factor Xa cleavage site) are added to the recombinant polypeptides. Bacterial expression systems for expressing the polypeptides are available in, e.g., *E. coli*, *Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of polypeptides of the invention, which are then purified using standard techniques (see, e.g., Colley et al., *J. Biol. Chem.*, 264:17619-17622 (1989); Guide to Protein Purification, in Methods in Enzymology, vol. 182 (Deutscher, ed., 1990)). Transformation of cells is performed according to standard techniques (see, e.g., Morrison, *J. Bact.*, 132:349-351 (1977); Clark-Curtiss & Curtiss, *Methods in Enzymology*, 101:347-362 (Wu et al., eds, 1983). For example, any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of a polypeptide of the invention. Polypeptides of the invention are recovered from the culture using standard techniques identified below.

C. Purification of Polypeptides

Polypeptides are purified to substantial purity by standard techniques known in the art, including, for example, extraction and purification from inclusion bodies, size differential filtration, solubility fractionation (i.e., selective precipitation with such substances as ammonium sulfate); column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when polypeptides are being purified. For example, polypeptides having established molecular adhesion properties can be reversible fused to recombinant polypeptides. With the appropriate ligand, the recombinant polypeptides can be selectively adsorbed to a purification column and then freed from the column in a relatively pure form. The fused polypeptide is then removed by enzymatic activity. Finally, the polypeptides may be purified using immunoaffinity columns.

IV. Methods of Identifying Polypeptides with Desired Activity

The polypeptides or peptidomimetics of the present invention can be readily screened for their ability to mediate cholesterol efflux and/or stabilize ABCA (e.g., ABCA1) using methods well known to those of skill in the art.

A number of different screening protocols can be utilized to identify polypeptides or peptidomimetics of the present invention that mediate cholesterol efflux and/or stabilize ABCA (e.g., ABCA1). In one embodiment, the screening methods involve screening a plurality of test polypeptides to identify those polypeptides that mediates cholesterol efflux and/or stabilizes ABCA (e.g., ABCA1) in, e.g., mammalian cells, including human cells.

In addition to screening for their ability to mediate cholesterol efflux and/or stabilize ABCA, candidate test polypeptides can also be screened for other activities including, e.g., anti-oxidant activities and anti-inflammatory activities. A number of different screening protocols can be utilized to identify polypeptides or peptidomimetics of the present invention that have anti-oxidant activity and/or anti-inflammatory activity.

It will be readily apparent to those of skill in the art that numerous other screening assays, in addition to those disclosed herein, can be used to screen the polypeptides or peptidomimetics of the present invention for the desired biological activities.

A. Screening for Cholesterol Efflux Activity

Suitable cholesterol efflux assays are described in, e.g., Bielicki, J. K and Oda, M. N., *Biochemistry*, 41:2089-2096 (2002); Jia et al., *Biochem. Biophys. Res. Common.*, 297:206-213 (2002). In some embodiments, a polypeptide known to mediate cholesterol efflux (e.g., helix 9/10 of Apo A-I) is used to screen for additional mediators of cholesterol efflux in a cell based assay. For example, cell lines in which cholesterol efflux can be enhanced using a cAMP analog that up-regulates ABCA1 protein expression (e.g., J774 macrophages) can conveniently be used to assess the ability of a polypeptide of the present invention to mediate cholesterol efflux. The cells are incubated with labeled cholesterol (e.g., [$^3$H]cholesterol) under conditions appropriate for cholesterol uptake by the cells. Thus, cAMP or cAMP analogs (e.g., CPT-cAMP) are incubated with the cells for a suitable time before the initiation of cellular cholesterol efflux, i.e., prior to contacting the cells with a test polypeptide. Measurement of labeled cholesterol appearing in the medium is used to determine the cholesterol efflux mediating activity of the test polypeptide.

B. Screening for ABCA Stabilization Activity

Multiple assays known in the art can be used to measure the ABCA stabilization activity of a polypeptide of the invention. For example, binding assays can be used to test the ability of the test polypeptide to bind to ABCA (e.g., ABCA1). It has been found that polypeptides having ABCA stabilization activity are also likely mediators of cholesterol efflux. As such, in a preferred embodiment, the polypeptides or peptidomimetics of the present invention have the ability to mediate cholesterol efflux and to stabilize ABCA. In one screening embodiment, the binding assays can be competitive assays. Other assays include, for example, direct measurement of ABCA (e.g., ABCA protein or nucleic acids) following contact with the test polypeptide.

1. Binding Assays

Binding assays usually involve contacting ABCA with one or more test polypeptides, and allowing sufficient time for ABCA and the test polypeptides to form a binding complex. Any binding complexes formed can be detected using any of a number of established analytical techniques. Protein binding assays include, but are not limited to, immunohistochemical binding assays, flow cytometry or other assays. In some embodiments, competition assays are used to determine whether a test polypeptide has ABCA stabilization activity. Competition assays are well known in the art. Typically, a competitor compound, i.e., a compound known to bind ABCA, is labeled so that differences in binding to ABCA (e.g., in the presence of increasing amount of a test polypeptide of the invention that may bind to ABCA) can be measured. The particular label or detectable group used in the assay is not a critical aspect of the invention, as long as it does not significantly interfere with the binding of the test compound to ABCA. As described herein, the detectable group (or, alternatively, detectable moiety or label) can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include, but are not limited to, magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

In some embodiments, ABCA expressing and non-expressing cells are used to measure the ABCA (e.g., ABCA1) stabilization activity of a test polypeptide by measuring the relative ABCA binding affinities of the test polypeptide and a competitor compound (e.g., full-length Apo A-I A or Apo A-I 9/10 polypeptide) for ABCA. In some embodiments, the binding affinity of full-length Apo A-I A to ABCA is compared to the binding affinity of a labeled polypeptide of the invention as described in, e.g., Remaley et al., *J. Lipid Res.*, 44:828-836 (2003). Cells expressing ABCA are incubated in the presence and absence of the competitor compound, and then exposed to a range of concentrations of individual labeled test polypeptides (e.g., a radiolabeled polypeptide of the invention). Typically, the concentrations of test polypeptides will range from about 0.1 µg/ml to about 200 µg/ml, about 0.5 µg/ml to about 100 µg/ml, about 1 µg/ml to about 40 µg/ml, or about 5 µg/ml to about 20 µg/ml.

2. Direct Measurement of ABCA

In some embodiments, the stabilization of ABCA is measured by direct measurement of ABCA (e.g., ABCA protein, or nucleic acid) using a cell based assay. Cell based assays can be performed in any cells in which ABCA is expressed (e.g., J774 macrophages), including cells which have been transfected with ABCA (e.g. HeLa cells). Any cell type can be used. For example, J774 macrophages can be used to assess relative ABCA1 protein levels in the presence and absence of polypeptides of the invention. The cells are first contacted with a compound that will induce ABCA (e.g., cAMP or a cAMP analogue such as, 8-bromo-cAMP) to upregulate ABCA (e.g., ABCA1) expression, then exposed to synthetic ABCA1 protein levels in the presence and absence of polypeptides of the invention in the absence of the cAMP stimulus to evaluate whether ABCA1 protein was stabilized or degraded. Relative levels of ABCA1 protein can be assessed using any means known in the art including, e.g., immunoblot analysis of cell membranes (Oram et al., *J. Biol. Chem.*, 278:52379-52385 (2003)) or hybridization of nucleic acid probes to ABCA mRNA.

C. Screening for Antioxidant Activity

Polypeptides or peptidomimetics of the invention can be screened for antioxidant activity using methods known in the art. For example, U.S. Patent Publication No. 2003/0087819 describes multiple assays that can be used to determine the antioxidant activity of a polypeptide, including, e.g., micelle substrate assays. A micelle substrate comprising a phospholipids (e.g., 1-palmitoyl-2-linoleoylphosphatidylcholine) is used to measure rates of lipid peroxidation catalyzed by specific enzymes (e.g., soybean lipoxygenase and/or xanthine/xanthine oxidase). The enzymes initiate lipid peroxidation following the addition of recombinant polypeptides of the invention to the phospholipid micelles. Increases in conjugated dienes (a product of lipid peroxidation) are monitored by ultraviolet absorption spectroscopy (234 nm) at 25° C. The mass of phospholipid hydroperoxides is calculated using the molar absorptivity coefficient ($\epsilon$=29,500 Lcm$^{-1}$ mol$^{-1}$) of conjugated dienes. Initial rates of lipoxygenase mediated lipid peroxidation are calculated from the slopes of the linear portion of the oxidation curves and results can be expressed as nmoles of phospholipid peroxide formed/min. Based on the maximum levels of lipid peroxide accumulation obtained in the absence of polypeptide (i.e., the plateau associated with the oxidation curves), it is possible to derive quantitative information regarding the potency of the polypeptides of the invention (e.g., a concentration of polypeptides resulting in 50% protection against lipid peroxidation). Other methods relates to screening for polypeptides capacity to prevent oxidation of ApoB lipoproteins as LDL, VLDL and Lp(A).

Other assays for screening for anti-oxidant activity are disclosed in PCT Publication No. WO 02/15923, the teachings of which are incorporated herein by reference.

D. Screening for Anti-Inflammatory Activity

Polypeptides or peptidomimetics of the invention can be screened for anti-inflammatory activity using any means known in the art. For example, assays to assess the activity of enzymes (e.g., lecithin:cholesterol acetyltransferase (LCAT) or paraoxonase (PON)) sensitive to inflammatory events can be used to assess the anti-inflammatory activity of the polypeptides of the inventions. Suitable assays are described in, e.g., Chen et al., *J. Lipid Res.*, 23:680-691 (1982), which describes quantification of LCAT activity using an exogenous proteoliposome substrate, and Forte et al., *J. Lipid Res.*, 43:477-485 (2002), which describes quantification of PON activity. Other screens can include monitoring the polypeptides capacity to inhibit the mRNA expression and/or protein production of target cells following various stimulations (for example, adhesion molecules, TNF-$\alpha$, LPS or combinations thereof).

E. Pre-$\beta$ Formation

Peptide of the invention may also be screened for the ability to induce pre$\beta$-1 HDL formation in human plasma. In one example of such an analysis, a peptide to be tested is added to human plasma. Plasma with and without peptide are incubated and then evaluated, e.g., by agarose gel electrophoresis in the first dimension followed by native gradient gel electrophoresis in the second dimension to evaluate the population of HDL particles present in the human plasma samples. A peptide of interest typically exhibits potent activity, e.g., at a molar ratio of peptide:ApoAI (in the plasma) of about 1:1 or less.

F. Further Testing

Polypeptides that are initially identified as mediating cholesterol efflux or interacting with ABCA can be further tested to validate their ability to mediate cholesterol efflux and/or stabilize ABCA. The basic format of such methods involves administering a lead compound identified during an initial screen to an animal that serves as a model. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like). In a preferred embodiment, Apo E −/− mice, Apo A-II −/− mice, or Apo C-III −/− mice are used. Additional animal models are described in, e.g., Marschang et al. *Sem. Cell Dev. Biol.*, 14:25-35 (2003).

G. High Throughput Screening

In one embodiment, high throughput screening (HTS) methods are used to identify polypeptides or peptidomimetics of the present invention that mediate cholesterol efflux and/or stabilize ABCA. HTS methods involve providing a combinatorial polypeptide library containing a large number of potential therapeutic compounds (i.e., polypeptides or peptidomimetics that mediate cholesterol efflux or stabilize ABCA). Such "libraries" are then screened in one or more assays, as described herein, to identify those library members (i.e., particular polypeptides or peptidomimetics) that display a desired characteristic activity. The compounds thus identified can serve as conventional "lead compounds" or can themselves be used as potential or actual therapeutics.

A combinatorial polypeptide library is a collection of diverse polypeptides generated by either chemical synthesis or biological synthesis, by combining a number of chemical "building blocks," i.e., amino acids. More particularly, a linear combinatorial polypeptide library is formed by combining a set of chemical building blocks (amino acids) in every possible way for a given compound length (i.e., the number of amino acids in a polypeptide compound). Millions of polypeptide compounds can be synthesized through such combinatorial mixing of chemical building blocks. In a preferred embodiment, conservative variants of the polypeptides of SEQ ID NOS:2-26 and 31-33 are generated and screened for desired biological activities (e.g., cholesterol efflux activity) in a high-throughput manner.

Devices for the preparation of combinatorial libraries are known to those of skill in the art and are commercially available from a number of different sources (see, e.g., ECIS™, Applied BioPhysics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

V. Methods of Use

The non-naturally occurring polypeptides of the present invention use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-oxidant activity as well as anti-inflammatory activity, any combination of these activities and, preferably, all of these activities.

In view of their biological activities and, in particular, their ability to mediate cholesterol efflux, the polypeptides of the present invention (or peptidomimetics thereof) can be used to treat elevated cholesterol levels in a mammal, or to treat prophylactically a mammal at risk of developing elevated cholesterol levels. In addition, the polypeptides or peptidomimetics can also be used for improving the lipid parameters in a mammal. An improvement in "lipid parameters" includes, for example, one or more of a decrease in the propensity of lipoproteins to adhere to a blood vessel, a decrease in the amount of atherosclerotic plaque (even though plasma LDL and/or HDL concentrations may not significantly changed), a reduction in the oxidative potential of an HDL or LDL particle, a regression in atherosclerosis (e.g., as measured by carotid angiography or ultrasound) and a reduction in cardiac events. Thus, the polypeptides or peptidomimetics of the present invention can be used to treat or prevent (i.e., prophylactically treat) diseases and conditions associated with dyslipidemia, hypercholesterolemia and inflammation, or diseases and conditions that are treatable by altering lipid parameters, such as those diseases and conditions disclosed herein.

In addition to the diseases and conditions specifically disclosed herein, those of skill in the art will know of other diseases and conditions associated with dyslipidemia, hypercholesterolemia and inflammation that can be treated or prevented using the polypeptides or peptidomimetics of the present invention.

A. Treating or Preventing a Symptom(s) of Atherosclerosis

In one embodiment, the present invention provides methods for treating, ameliorating and/or preventing one or more symptoms of atherosclerosis. The methods preferably involve administering to an organism, preferably a mammal and, more preferably, a human, one or more of the polypeptides of this invention (or peptidomimetics of such polypeptides). The polypeptide(s) can be administered, as described herein, according to any of a number of standard methods including, but not limited to, injection, suppository, nasal spray, time-release implant, transdermal patch, orally and the like. In one particularly preferred embodiment, the polypeptide(s) is administered orally (e.g., as a syrup, capsule, tablet, etc.).

The methods of the present invention are not limited to treating humans or non-human animals having one or more symptom(s) of atherosclerosis (e.g., hypertension, narrowing of vessels, plaque formation and rupture, heart attack, angina, or stroke, high levels of plasma cholesterol, high levels of low density lipoprotein, high levels of very low density lipoprotein, or inflammatory proteins, etc.), but are also very useful in a prophylactic context. Thus, the polypeptides of this invention (or peptidomimetics thereof) can be administered to an organism, such as a human or non-human animal, to prevent the onset, i.e., development, of one or more symptoms of atherosclerosis. Suitable candidate subjects for prophylactic treatment include, for example, those subjects having one or more risk factors for atherosclerosis (e.g., family history, genetic markers that correlate with atherosclerosis, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

Treatment can complement or obviate the need for vascular surgery making anti-atherosclerosis treatment systemic and sustainable. Thus, the peptide can be given before intervention to optimize circulation before surgery, during surgery for regional administration in the vasculature or its vicinity, or post-surgery to lessen inflammation and atherosclerosis caused by mechanical trauma by surgical intervention.

B. Treating or Preventing a Symptom(s) of Atherosclerosis Associated with an Acute Inflammatory Response The atherosclerosis-inhibiting polypeptides of this invention are also useful in a number of other contexts. In particular, it has been found that cardiovascular complications (e.g., atherosclerosis, stroke, etc.) frequently accompany or follow the onset of an acute phase inflammatory response. Such an acute phase inflammatory response is often associated with a recurrent inflammatory disease (e.g., leprosy, tuberculosis, systemic lupus erythematosus, rheumatoid arthritis, etc.), a viral infection (e.g., influenza, HIV, etc.), a bacterial infection, a fungal infection, an organ transplant, a wound or other trauma, an implanted prosthesis, a biofilm, and the like.

In view of their antioxidant activity, the polypeptides described herein can be used to reduce or prevent the formation of oxidized phospholipids during or following an acute phase inflammatory response, thereby mitigating or eliminating cardiovascular complications associated with such a condition.

Thus, in certain embodiments, this invention contemplates administering one or more of the polypeptides of this invention to a subject at risk for, or incurring, an acute phase inflammatory response and/or at risk for or incurring a symptom of atherosclerosis.

The peptides of the invention effects lipids and thereby can be useful for the treatment of disease states in which lipids and lipid metabolism play a role. Thus, for example, a person having or at risk for coronary disease can prophylactically be administered a polypeptide of this invention during flu season. A human (or other animal) subject to a recurrent inflammatory condition, e.g., rheumatoid arthritis, various autoimmune diseases, etc., can be treated with a polypeptide of this invention to mitigate or prevent the development of atherosclerosis or stroke. Similarly, a human (or other animal) subject to trauma, e.g., acute injury, tissue transplant, etc., can be treated with a polypeptide of this invention to mitigate or prevent the development of atherosclerosis or stroke.

In certain instances, such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example, cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase inflammatory response, or risk therefore is evaluated by measuring one or more APPs. Measuring such markers is well known to those of skill in the art, and commercial companies exist that provide such measurement (e.g., AGP measured by Cardiotech Services, Louisville, Ky.). Once it has been determined that a person is experiencing an acute phase inflammatory response or is at risk of experiencing an acute phase inflammatory response, the polypeptides of the present invention can be administered to reduce or prevent the formation of oxidized phospholipids during or following the acute phase inflammatory response, thereby mitigating or eliminating cardiovascular complications associated with such a condition.

C. Treating or Preventing a Symptom(s) or Condition Associated with Coronary Calcification and Osteoporosis It has also been found that oxidized lipids can be a cause of coronary calcification and osteoporosis. It is also thought that oxidized lipids can be involved in the pathogenesis of calcific aortic stenosis.

Thus, in another embodiment, the polypeptides of the present invention are used to treat, inhibit or prevent a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis and the like. In such methods, the polypeptides or peptidomimetics of the present invention can be administered to a human or non-human animal to reduce or prevent the formation of oxidized phospholipids, thereby inhibiting or preventing a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis and the like.

Typically, all of the above methods involve the administration of a single polypeptide of this invention or, alternatively, the administration of two or more different polypeptides of this invention. Such polypeptides can be administered alone or in combination with other therapeutic agents, such as those disclosed herein. The polypeptides can be provided as monomers or in dimeric, oligomeric or polymeric forms. In certain embodiments, the multimeric forms may comprise associated monomers (e.g., ionically or hydrophobically linked); whereas, in other embodiments, other multimeric forms comprise covalently linked monomers (directly linked or through a linker).

In addition, although all of the foregoing methods are described herein with respect to humans, it will be readily apparent to those of skill that such methods are also useful for other animals, i.e., for veterinary use. Thus, preferred organisms include, but are not limited to, humans, non-human primates, canines, equines, felines, porcines, ungulates, largomorphs, and the like.

D. Stabilization of Vulnerable Plaques

As explained herein, heart disease, specifically coronary artery disease, is a major cause of death, disability, and healthcare expense in the United States and other industrialized countries. Until recently, most heart disease was considered to be primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot (thrombus). The clot may choke off the flow of oxygen-rich blood (ischemia) to heart muscles, causing a heart attack. Alternatively, the clot may break off and lodge in the vessel of another organ, such as the brain, resulting in a thrombotic stroke.

Within the past decade, however, evidence has emerged changing to some extent the paradigm of atherosclerosis, coronary artery disease, and heart attacks. While the buildup of hard plaque may produce angina and severe ischemia in the coronary arteries, new clinical data suggest that the rupture of vulnerable plaques, which are often non-occlusive, per se, causes the vast majority of heart attacks. The rate is estimated as high as 60-80 percent.

In many instances, vulnerable plaques do not impinge on the vessel lumen; rather, much like an abscess, they are ingrained within the arterial wall. The majority of vulnerable plaques include a lipid pool, smooth muscle (endothelial) cells, and a dense infiltrate of cholesterol filled macrophages/foam cells contained by a thin fibrous cap. The lipid pool is believed to be formed as a result of pathological process involving low density lipoprotein (LDL), macrophages, and the inflammatory process. The macrophages oxidize the LDL, producing foam cells.

The macrophages, foam cells and associated endothelial cells release various substances, such as tumor necrosis factor, tissue factor, and matrix proteinases, which result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque may then spill into the blood stream, thereby initiating a clotting cascade. The cascade produces a blood clot that potentially results in a heart attack and/or stroke. The process is exacerbated due to the release of collagen and plaque components (e.g., collagen and tissue factor), which enhance clotting upon their release.

It has been found that the polypeptides of the present invention can stabilize vulnerable plaques by reducing plaque lipid content through reverse cholesterol transport. Thus, in another embodiment, the present invention provides methods for stabilizing a vulnerable plaque in a blood vessel of a mammal by administering to the mammal (and, more preferably, a human), one or more of the polypeptides of this invention (or peptidomimetics of such polypeptides). A "vulnerable" plaque is generally defined as a lipid-rich plaque with a thinned fibrous cap lacking proper collagen and smooth muscle cell support. Again, the polypeptides of the present invention can reduce plaque lipid content, thereby stabilizing such "vulnerable" plaques.

In one embodiment, the mammal is a mammal diagnosed as having one or more vulnerable plaques. In this embodiment, a number of different diagnostic assays have been developed for the detection (e.g., diagnosis and localization) of vulnerable plaques, including temperature detection strategies, labeling strategies, imaging strategies (e.g., devices utilizing magnetic resonance, ultrasound, infra-red, fluorescence, visible light, radio waves, x-ray, etc.), general strategies for discriminating the vulnerable plaque from surround healthy vascular tissue and the like (see, e.g., U.S. Pat. Nos. 6,245,026, 6,475,159, 6,475,210 and 7,118,567). One strategy involves the measurement of temperature within a blood vessel. For example, vulnerable plaque tissue temperature is generally elevated compared to healthy vascular tissue. Measurement of this temperature discrepancy allows detection of the vulnerable plaque. Another detection strategy involves labeling vulnerable plaque with a marker. The marker can be a substance specific for a component and/or characteristic of the vulnerable plaque (such as C-reactive protein). For example, the marker may have an affinity for the vulnerable plaque, more so than for healthy tissue. Detection of the marker may thus allow detection of the vulnerable plaque. Alternatively, the marker may not necessarily have an affinity for the vulnerable plaque, but will simply change properties while associated with the vulnerable plaque. The property change may be detected and thus allow detection of the vulnerable plaque.

In another embodiment, the mammal is at risk of having one or more vulnerable plaques. In this embodiment, a clinical symptom has developed and/or a clinical event has occurred that leads one of skill in the art to believe that the mammal is at risk of having one or more vulnerable plaques.

In connection with the above methods of stabilizing a vulnerable plaque, the polypeptide(s) can be administered, as described herein, according to any of a number of standard methods including, but not limited to, injection, infusion, suppository, nasal spray, time-release implant, transdermal patch, orally and the like. In one particularly preferred embodiment, the polypeptide(s) is administered orally (e.g., as a syrup, capsule, tablet, etc.). In addition, the polypeptides (or peptidomimetics) of the present invention can be used alone or in combination with other known pharmaceutical agents for the treatment of dyslipidemia, hypercholesterolemia and inflammation to raise plasma HDL concentrations and/or to promote reverse cholesterol transport.

VI. Combination Therapy

In some embodiments, the polypeptides or peptidomimetics of the present invention are administered in combination with one or more additional therapeutic agents for treating or preventing diseases and disorders associated with dyslipidemia, hypercholesterolemia and inflammation, such as cardiovascular disease, including atherosclerosis. For instance, in one embodiment, a polypeptide of the present invention is administered in conjunction with any of the standard treatments for atherosclerosis including, for example, statins (e.g., atorvastatin, lovastatin, pravastatin, simvastatin, fluvastatin, or rosuvastatin); a Nieman-Pick C1-Like 1 sterol transporter channel inhibitor (e.g., Ezetimibe); bile acid binders (e.g., cholestyramine or colestipol); platelet clumping inhibitors (e.g., aspirin, ticlopidine, or clopidogrel); niacin/nicotinamide; PPAR activators; Vitamin E; surgical intervention (e.g., angioplasty, stents, stents, or endarterectomy); and lifestyle changes (e.g., low-fat diets, weight loss, and exercise).

More particularly, the polypeptides or peptidomimetics of the present invention can be used in combination, either as separate units or fixed combinations, with one or more of the following: an antibody which binds to an unwanted inflammatory molecule or cytokine such as interleukin-6, interleukin-8, granulocyte macrophage colony stimulating factor, and tumor necrosis factor-α; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional therapeutic agents.

The polypeptides or peptidomimetics of the present invention can be used in combination with drugs commonly used to treat lipid disorders in, for example, diabetic patients. Such drugs include, but are not limited to, HMG-CoA reductase inhibitors, nicotinic acid, ezetimide, bile acid sequestrants, fibric acid derivatives, MTP inhibitor, ACAT inhibitor and CETP inhibitors. Examples of HMG-CoA reductase inhibitors include lovastatin, pravastatin, simvastatin, rosuvastatin, fluvastatin and atorvastatin. Examples of bile acid sequestrants include cholestyramine, colestipol and colesevelam. Examples of fibric acid derivatives include gemfibrozil and fenofibrate, The polypeptides or peptidomimetics of the invention can also be used in combination with anti-hypertensive drugs, such as, for example, diuretics, β-blockers, cathepsin S inhibitors, methyldopa, α2-adrenergic agonists, guanadrel, reserpine, β-adrenergic receptor antagonists, α1-adrenergic receptor antagonists, hydralazine, minoxidil, calcium channel antagonists, ACE inhibitors and angiotensin II-receptor antagonists. Examples of β-blockers include acebutolol, bisoprolol, esmolol, propanolol, atenolol, labetalol, carvedilol and metoprolol. Examples of ACE inhibitors include captopril, enalapril, lisinopril, benazepril, fosinopril, ramipril, quinapril, perindopril, trandolapril and moexipril.

The polypeptides or peptidomimetics of the invention can also be used in combination with cardiovascular drugs such as calcium channel antagonists, β-adrenergic receptor antagonists and agonists, aldosterone antagonists, ACE inhibitors, angiotensin II receptor antagonists, nitrovasodilators, and cardiac glycosides. The polypeptides or peptidomimetics of the invention can also be used in combination with anti-inflammatory drugs such as H1-receptor antagonists, H2-receptor mediated agonists and antagonists, COX-2 inhibitors, NSAID, salicylates, acetaminophen, propionic acid derivatives, enolic cids, diaryl substituted fuanones, cyclooxygenase inhibitors, and bradykinin agonists and antagonists.

Other therapeutic agents suitable for use in combination with the polypeptides or peptidomimetics of the present invention are disclosed in U.S. Patent Application Publication No. 2005/0142180, which was published Jun. 30, 2005, the teachings of which are incorporated herein by reference.

The polypetide (or peptidomimetics thereof) and the additional therapeutic agent can be administered simultaneously or sequentially. For example, the polypeptide may be administered first, followed by the additional therapeutic agent. Alternatively, the additional therapeutic agent may be administered first, followed by the polypeptide of the invention. In some cases, the polypeptide of the invention and the additional therapeutic agent are administered in the same formulation. In other cases, the polypeptide and the additional therapeutic agent are administered in different formulations. When the polypeptide and the additional therapeutic agent are administered in different formulations, their administration may be simultaneous or sequential.

VII. Pharmaceutical Formulations

In order to carry out the methods of the invention, one or more polypeptides of this invention or peptidomimetics thereof are administered to an individual diagnosed as having or at risk of having a disease or disorder associated with dyslipidemia, hypercholesterolemia and inflammation (e.g., to an individual diagnosed as having one or more symptoms of atherosclerosis, or as being at risk for atherosclerosis). The polypeptides or peptidomimetics thereof can be administered in their "native" form or, if desired, in the form of, for example, salts, esters, amides, prodrugs, derivatives, and the like, provided that the salt, ester, amide, prodrug or derivative is suitable pharmacologically, i.e., effective in the methods of the present invention.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectibles, implantable sustained-release formulations, etc.

As such, in another aspect, the present invention provides pharmaceutical compositions comprising a pharmaceutically effective amount of a polypeptide or peptidomimetic of the present invention and an acceptable carrier and/or excipients. A pharmaceutically acceptable carrier includes any solvents, dispersion media, or coatings that are physiologically compatible and that preferably does not interfere with or otherwise inhibit the activity of the polypeptide or peptidomimetic. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include, but are not limited to, wetting agents, emulsifying agents, dispersing agents or preservatives which are particularly useful for preventing the growth or action of microorganisms. Various preservatives are well known and include, for example, phenol and ascorbic acid. One skilled in the art will appreciate that the choice of pharmaceutically acceptable carrier(s), including a physiologically acceptable compound depends, for example, on the route of administration of the polypeptide(s) or peptidomimetic(s) and on the particular physio-chemical characteristics of the polypeptide(s) or peptidomimetic(s).

In a preferred embodiment, the pharmaceutically acceptable carrier is physiological saline. Other pharmaceutically acceptable carriers and their formulations are well-known and generally described in, for example, *Remington: The Science and Practice of Pharmacy,* 21st Edition, Philadelphia, Pa. Lippincott Williams & Wilkins, 2005. Various pharmaceutically acceptable excipients are well-known in the art and can be found in, for example, Handbook of Pharmaceutical Excipients ($5^{th}$ ed., Ed. Rowe et al., Pharmaceutical Press, Washington, D.C.). Again, the pharmaceutical composition can be formulated as a solution, microemulsion, liposome, capsule, tablet, or other suitable form. The active component may be coated in a material to protect it from inactivation by the environment prior to reaching the target site of action.

In certain preferred embodiments, the polypeptides or peptidomimetics of this invention can be administered orally (e.g., via a tablet) or as an injectable in accordance with standard methods well known to those of skill in the art. In other preferred embodiments, the polypeptides or peptidomimetics can also be delivered through the skin using conventional transdermal drug delivery systems, i.e., transdermal "patches," wherein the polypeptide(s) or peptidomimetic(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

In some embodiments, implanted devices (e.g., arterial and intravenous stents, including eluting stents, and catheters) are used to deliver the formulations comprising the polypeptides and peptidomimetics of the invention. For example, aqueous solutions comprising the polypeptides and peptidomimetics of the invention are administered directly through the stents and catheters. In some embodiments, the stents and catheters may be coated with formulations comprising the polypeptides and peptidomimetics described herein. In some embodiments, the polypeptides and peptidomimetics will be in time-release formulations an eluted from the stents. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829,497; 6,827,798; 6,827,730; 6,827,703; 6,824,554; 6,824,553; 6,824,551; 6,824,532; and 6,819,951.

Unlike typical polypeptide formulations, the polypeptides of this invention comprising L-form or D-form amino acids can be administered, even orally, without protection against proteolysis by stomach acid, etc. Nevertheless, in certain embodiments, polypeptide delivery can be enhanced by the use of protective excipients. This is typically accomplished either by complexing the polypeptide with a composition to render it resistant to acidic and enzymatic hydrolysis, or by packaging the polypeptide in an appropriately resistant carrier such as a liposome. Means of protecting polypeptides for oral delivery are well known in the art (see, e.g., U.S. Pat. No. 5,391,377, which describes lipid compositions for oral delivery of therapeutic agents).

Elevated serum half-life can be maintained by the use of sustained-release polypeptide "packaging" systems. Such sustained release systems are well known to those of skill in the art. In one preferred embodiment, the ProLease biodegradable microsphere delivery system for proteins and polypeptides is used (Tracy, *Biotechnol. Prog.*, 14:108 (1998); Johnson et al., *Nature Med.*, 2:795 (1996); Herbert et al., *Pharmaceut. Res.*, 15:357 (1998)), which involves the use of a dry powder composed of biodegradable polymeric microspheres containing the polypeptide in a polymer matrix that can be compounded as a dry formulation with or without other agents.

The ProLease microsphere fabrication process was designed to achieve a high polypeptide encapsulation efficiency while maintaining protein integrity. The process consists of (i) preparation of freeze-dried protein particles from bulk polypeptide by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the polypeptide, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., $-40°$ C.). During encapsulation, the polypeptide is maintained in the solid state in the absence of water, thus minimizing water-induced conformational mobility of the polypeptide, preventing polypeptide degradation reactions that include water as a reactant, and avoiding organic-aqueous interfaces where polypeptides may undergo denaturation. A preferred process uses solvents in which most polypeptides are insoluble, thus yielding high encapsulation efficiencies (e.g., greater than 95%).

In another embodiment, one or more components of the solution can be provided as a "concentrate," e.g., in a storage container (e.g., in a premeasured volume) ready for dilution, or in a soluble capsule ready for addition to a volume of water.

In certain embodiments of the present invention, the pharmaceutical compositions are sustained release formulations. Polypeptides or peptidomimetics of the present invention may be admixed with biologically compatible polymers or matrices which control the release rate of the copolymers into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. Acceptable carriers include carboxymethyl cellulose (CMC) and modified CMC.

The pharmaceutical composition of the present invention is preferably sterile and non-pyrogenic at the time of delivery, and is preferably stable under the conditions of manufacture and storage. These pharmaceutical compositions can be sterilized by conventional, well known sterilization techniques.

In therapeutic applications, the compositions of this invention are administered to an individual diagnosed as having or at risk of having a disease or disorder associated with dyslipidemia, hypercholesterolemia and inflammation (and, in preferred embodiments, to an individual diagnosed as having one or more symptoms of atherosclerosis or as being at risk for atherosclerosis) in an amount sufficient to cure or at least partially prevent or arrest the disease, condition and/or its complications. An amount adequate to accomplish this is defined as a "therapeutically effective dose." Amounts effective for this use will depend upon the severity of the disease and the general state of the patient's health. Single or multiple administrations of the compositions can be administered depending on the dosage and frequency as required and tolerated by the patient. In any event, the composition should provide a sufficient quantity of the active agents, i.e., polypeptides or peptidomimetics, of the formulations of this invention to effectively treat (ameliorate one or more symptoms) the individual or patient.

The concentration of polypeptide or peptidomimetic can vary widely, and will be selected primarily based on fluid volumes, viscosities, body weight, circulating plasma levels of the polypeptide, polypeptide toxicities, progression of the disease (e.g., atherosclerosis), the production of antibodies that specifically bind to the polypeptide, and the like in accordance with the particular mode of administration selected and the patient's needs. Typically, the dose equivalent of a polypeptide or peptidomimetic is from about 0.1 to about 50 mg per kg, preferably from about 1 to about 25 mg per kg, most preferably from about 1 to about 20 mg per kg body weight. It will be appreciated that such dosages may be varied to optimize a therapeutic regimen in a particular subject or group of subjects.

For administration, polypeptides of the present invention can be administered at a rate determined by the LD50 of the polypeptide, and the side-effects of the polypeptide at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

As explained herein, the polypeptides or peptidomimetics of the present invention can be modified in a number of different ways. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. In addition, to enhance delivery and/or biological activities in vivo, salts, esters, amides, prodrugs and other derivatives of the polypeptides or peptidomimetics of the present invention can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology, which typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the polypeptides described herein are halide salts, such as may be prepared using hydrochloric or hydrobromic acids. Conversely, preparation of basic salts of the polypeptides or peptidomimetics of the present invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., sodium salts and copper salts.

Preparation of Esters Typically Involves Functionalization of Hydroxyl and/or Carboxyl groups that may be present within the polypeptides or peptidomimetics of the present invention. The esters are typically acyl-substituted derivatives of free alcohol groups, i.e., moieties that are derived from carboxylic acids of the formula RCOOH, wherein R is alkyl and, preferably, lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The foregoing formulations and administration methods are clearly intended to be illustrative and not limiting in any way. It will be appreciated that, using the teaching provided herein, other suitable formulations and modes of administration can be readily devised.

VIII. Lipid-Based Formulations

In another aspect, the polypeptides and peptidomimetics of the present invention are preferably administered in conjunction with one or more lipids. The lipids can be formulated as an excipient to protect and/or enhance transport/uptake of the polypeptides or peptidomimetics or they can be administered separately.

The lipids can be formulated into liposomes, nanocapsules, microparticles, microspheres, lipids particles, lipid vesicles and the like. Such lipid formulations can be used to encapsulate the polypeptides and peptidomimetics of the present invention and/or they can be simply complexed/admixed with such polypeptides and peptidomimetics. Those of skill in the art will know how to use such lipid formulations to either encapsulate or complex the polypeptides or peptidomimetics of the present invention. For instance, the formation and use of liposomes is generally known to those of skill in the art. Recently, liposomes were developed with improved serum stability and circulation half-times (see, U.S. Pat. No. 5,741, 516). Further, various methods of liposome and liposome-like preparations as potential drug carriers have been reviewed (see, U.S. Pat. Nos. 5,567,434; 5,552,157; 5,565, 213; 5,738,868 and 5,795,587).

In one embodiment, the polypeptides or peptidomimetics of the present invention are complexed with a lipid, such as a phospholipid (e.g., 1-palmitoyl-2-oleoyl-sn-glycerol-phosphatidylcholine ("POPC") in a manner similar to that disclosed in U.S. Patent Application Publication No. 2005/0142180, which was published Jun. 30, 2005, the teachings of which are incorporated herein by reference. It has surprisingly been found that when the polypeptides and peptidomimetics of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells.

As such, the present invention provides polypeptide-lipid complexes (or, alternatively, peptidomimetic-lipid complexes) having an increased ability to efflux cholesterol from cells. Typically, the lipid is mixed with the polypeptide prior to administration. The polypeptides of the present invention and lipids can be mixed in an aqueous solution in appropriate ratios and can be complexed by methods known in the art, including, but not limited to, freeze-drying, detergent solubilization followed by dialysis, microfluidization, sonication, and homogenization. Complex efficiency can be optimized, for example, by varying pressure, ultrasonic frequency or detergent concentration. An example of a detergent commonly used to prepare polypeptide-lipid complexes is sodium cholate.

In certain embodiments, the polypeptide-lipid (e.g., phospholipids) complex can be in solution with an appropriate pharmaceutical diluent or carrier. In other embodiments, freeze-dried or lyophilized preparations of the polypeptide-lipid complexes can be hydrated or reconstituted with an appropriate pharmaceutical diluent prior to administration. In another embodiment, the polypeptide-lipid complexes can be frozen preparations that are thawed until a homogenous solution is achieved prior to administration to a subject in need thereof.

The lipid can be any suitable lipid known to those of skill in the art. In one embodiment, non-phosphorus containing lipids can be used, including stearylamine, dodecylamine, acetyl palmitate, (1,3)-D-mannosyl-(1,3)digly-ceride, aminophenylglycoside, 3-cholesteryl-6'-(glycosylthio)hexyl ether glycolipids, N-(2,3-di(9-(Z)-octadecenyloxy))-prop-1-yl-N,N, N-trimethylammonium chloride and fatty acid amides.

In another embodiment, a phospholipids or a mixture of phospholipids is used. Suitable phospholipids include, but are not limited to, can be a small alkyl chain phospholipid, phosphatidylcholine, egg phosphatidylcholine, soybean phosphatidylcholine, dipalmitoylphosphatidylcholine, soy phosphatidylglycerol, egg phosphatidylglycerol, distearoylphosphatidylgly-cerol, dimyristoylphosphatidylcholine, distearoylphosphatidylcholine, dilaurylphosphatidylcholine, 1-myristoyl-2-palmitoylphosphatidylcholine, 1-palmitoyl-2-myristoylphosphatidylcholine, 1-palmitoyl-2-stearoylphospha-tidylcholine, 1-stearoyl-2-palmitoylphosphatidylcholine, dioleoylphosphatidylcholine, 1-palmitoyl-2-oleoylphosphatidylcholine, 1-oleoyl-2-palmitylphosphatidylcholine, dioleoylphosphatidyl ethanolamine, dilauroylphosphatidylglycerol, phosphatidylserine, phosphatidylethanolamine, phosphatidylinositol, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, phosphatidic acid, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, sphingolipids, brain sphingomyelin, dipalmitoylsphingomyelin, distearoylsphingomyelin, galactocerebroside, gangliosides, cerebrosides, phosphatidylglycerol, phosphatidic acid, lysolecithin, lysophosphatidylethanolamine, cephalin, cardiolipin, dicetylphosphate, distearoyl-phosphatidylethanolamine and cholesterol and its derivatives. Similarly, the phospholipid can be a derivative or analogue of any of the foregoing phospholipids or, again, a mixture of two or more of any of the foregoing phospholipids. Such phospholipids can be obtained from commercial sources, natural sources or by synthetic or semi-synthetic means known to those of skill in the art.

In preferred embodiments, the polypeptide-lipid complex is a polypeptide-phospholipid-complex. In a more preferred embodiment, the lipid is 1-palmitoyl-2-oleoyl phosphatidylcholine ("POPC") or ("1-palmitoyl-2-oleoyl-sn-glycero-3-phosphocholine").

It will be readily apparent to those of skill in the art that the complex comprising a polypeptide of the present invention and a lipid, preferably a phospholipids, can comprise any amount of lipid and any amount of the polypeptide, provided the complex is effective to mediate cholesterol efflux and, in turn, to treat diseases or symptoms associate therewith. As previously mentioned, it has surprisingly been found that when the polypeptides of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells. However, the polypeptide-lipid complexes of the present invention can comprise complexes with other ratios of phospholipid to polypeptide, such as about 100:1, about 10:1, about 5:1, about 3:1, about 2:1, about 1:1, about 1:2, about 1:3, about 1:5, about 1:10 and about 1:100 (wt of polypeptide/wt of lipid).

The polypeptide-lipid complexes of the present invention can be made by any method known to one of skill in the art. In some cases, it is desirable to mix the lipid and the polypeptide prior to administration. Lipids can be in solution or in the form of liposomes or emulsions formed using standard techniques, such as homogenization, sonication or extrusion. Sonication is generally performed with a tip sonifier, such as a Branson tip sonifier, in an ice bath. Typically, the suspension is subjected to several sonication cycles. Extrusion can be carried out by biomembrane extruders, such as the Lipex Biomembrane Extruder™ (Lipex Biomembrane Extruder, Inc. Vancouver, Canada). Defined pore size in the extrusion filters can generate unilamellar liposomal vesicles of specific sizes. The liposomes can also be formed by extrusion through an asymmetric ceramic filter, such as a Ceraflow Microfilter™, which is commercially available from the Norton Company, Worcester, Mass., or through a polycarbonate filter or other types of polymerized materials (i.e., plastics) known to those of skill in the art.

As previously mentioned, the polypeptide-lipid complexes of the present invention can be prepared in a variety of forms including, but not limited to, vesicles, liposomes or proteoliposomes. A variety of methods well known to those skilled in the art can be used to prepare the polypeptide-lipid complexes. A number of available techniques for preparing liposomes or proteoliposomes can be used. For example, a polypeptide of the present invention (e.g., a polypeptide of SEQ ID NOS:1-26 or 31-33), can be co-sonicated (using a bath or probe sonicator) with the appropriate lipid to form the polypeptide-lipid complexes. In certain embodiments, the polypeptide can be combined with preformed lipid vesicles resulting in the spontaneous formation of an polypeptide-lipid complex. In another embodiment, the polypeptide-lipid complex can also be made by a detergent dialysis method. In this method, a mixture of the polypeptide, lipid and a detergent, such as sodium cholate, can be dialyzed to remove the detergent and reconstituted to make the polypeptide-lipid complexes (see, e.g., Jonas et al., *Methods Enzymol.*, 128:553-82 (1986)).

In other embodiments, the polypeptide-lipid complexes can be made by co-lyophilization as described in U.S. Pat. Nos. 6,287,590 and 6,455,088, the teachings of both of which are hereby incorporated by reference in their entirety. Other methods are disclosed in, for example, U.S. Pat. Nos. 6,004, 925, 6,037,323 and 6,046,166, the teachings of all of which are incorporated herein by reference in their entireties. Other methods of preparing polypeptide-lipid complexes will be apparent to those of skill in the art.

In one preferred embodiment, the polypeptide-lipid complexes can be made by homogenization.

In an additional aspect, the invention provides a synthetic lipid particle comprising a polypeptide of the invention. Such a particle can be used for the delivery of a therapeutic or diagnostic agent. In some embodiments, a polypeptide of the invention is a component of a synthetic LDL particle. In other embodiments, a polypeptide of the invention is a component of a synthetic HDL particle. In some embodiments, the particle is less than about 500 nm in diameter or less than about 200 nm in diameter. In other embodiments, the particle is than about 80 nm in diameter. In some embodiments the particle is less than about 25 nm in diameter. Methods of making such particles are known in the art (see, e.g., U.S. Patent Application Publication Nos. 20040229794 and 20070167351 and references described therein).

In some embodiments, the synthetic lipid particle comprises an antibiotic or drug for the treatment of an infection. Such an agent can include antibiotic or antimicrobial (e.g., antibacterial, antifungal, and antiviral) agents.

In further embodiments, a synthetic lipid particle comprising a peptide of the invention comprises an agent for the treatment or diagnosis of cancer or an agent for the treatment of a nervous system disorder. For example, a synthetic particle comprising a peptide as described here can be administered for the treatment or diagnosis of tumors or for the treatment or diagnosis of blood cell cancers. Tumors includes carcinomas and sarcomas. Exemplary cancers that can be treated include cancers of the kidney, breast, lung, bladder, colon, ovarian, prostate, pancreas, stomach, brain, head and neck, skin, uterine cancer, testicular cancer, glioma, esophageal cancer, and liver cancer. Blood cell cancers include B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers.

In some embodiments, the synthetic lipid particle of the present invention is used to treat diseases of the central nervous system. In some embodiments, the disease of the central nervous system is selected from the group consisting of stroke, epilepsy, head trauma, viral infection (e.g., HIV-associated cognitive dysfunction, meningitis caused by picornavirus, togavirus, herpesvirus paramyxovirus, and areanavirus), bacterial infection (e.g., meningitis such as cryptococcal meningitis and fulminant bacterial meningitis, neurotuberculosis, toxoplasmosis, and neurosyphilis), fungal, rickettsial, protozoan, or helminthic infections, Alzheimer's disease, Parkinson's disease, multiple sclerosis, and hereditary metabolic diseases of the brain.

Such synthetic particles can be administered to the patient systemically or locally.

In some embodiments, a peptide of the invention that is incorporated into a particle is joined to a targeting moiety, e.g., a peptide that binds to a cell surface receptor, to direct the particle to cells of interest.

As appreciated by one of skill in the art, in another aspect of the invention, the peptides described herein may also be used in formulating particles that may not comprise lipids, which can also be used for the delivery of diagnostic or therapeutic agents as described above. Examples of particles that may not be lipid-based are described, e.g., in U.S. Patent Application Publication Nos. 20070128290 and 20050238725 and references described therein. For example, a peptide of the invention may be employed as a water soluble component that is adsorbed to or associated with the surface of a particle comprising a therapeutically or diagnostically active agent. Such particles are generally less than about 1000 nm or 500 nm in diameter or less than about 200 nm in diameter. In other embodiments, the particle is than about 80 nm in diameter. In some embodiments the particle is less than about 25 nm in diameter.

IX. Nucleic Acids and Gene Therapy

In another embodiment, the present invention provides isolated nucleic acids encoding the polypeptides disclosed herein, expression vectors comprising the nucleic acids, and host cells comprising the expression vectors. More particularly, the present invention provides isolated nucleic acids encoding the polypeptides of the present invention having cholesterol efflux activities similar to full-length apolipoproteins, on a per molecule basis, and having high selectivity for ABAC1 in a manner similar to full-length apolipoproteins, the polypeptides including, but not limited to, the polypeptides having an amino acid sequence comprising SEQ ID NOS:1-33.

In certain embodiments, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with dyslipidemia, hypercholesterolemia and inflammation.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science*, 256:808-813 (1992); Nabel et al., *TIBTECH*, 11:211-217 (1993); Mitani et al., *TIBTECH*, 11:162-166 (1993); Mulligan, *Science*, 926-932 (1993); Dillon, *TIBTECH*, 11:167-175 (1993); Miller, *Nature*, 357:455-460 (1992); Van Brunt, *Biotechnology*, 6(10):1149-1154 (1998); Vigne, *Restorative Neurology and Neuroscience*, 8:35-36 (1995); Kremer et al., *British Medical Bulletin*, 51(1):31-44 (1995); Haddada et al., in *Current Topics in Microbiology and Immunology* (Doerfler & Bohm eds., 1995); and Yu et al., *Gene Therapy*, 1:13-26 (1994)).

For delivery of nucleic acids, viral vectors may be used. Suitable vectors include, for example, herpes simplex virus vectors as described in Lilley et al., *Curr. Gene Ther.*, 1(4): 339-58 (2001), alphavirus DNA and particle replicons as described in e.g., Polo et al., *Dev. Biol.* (Basel), 104:181-5 (2000), Epstein-Barr virus (EBV)-based plasmid vectors as described in, e.g., Mazda, *Curr. Gene Ther.*, 2(3):379-92 (2002), EBV replicon vector systems as described in e.g., Otomo et al., *J. Gene Med.*, 3(4):345-52 (2001), adeno-virus associated viruses from rhesus monkeys as described in e.g., Gao et al., *PNAS USA.*, 99(18):11854 (2002), adenoviral and adeno-associated viral vectors as described in, e.g., Nicklin et al., *Curr. Gene Ther.*, 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al., *Mol. Cell. Biol.*, 8:3988-3996 (1988); Vincent et al. (1990) *Vaccines* 90 (Cold Spring Harbor Laboratory Press); Carter, *Current Opinion in Biotechnology* 3:533-539 (1992); Muzyczka, *Current Topics in Microbiol. and Immunol.*, 158:97-129

(1992); Kotin, *Human Gene Therapy*, 5:793-801 (1994); Shelling et al., *Gene Therapy*, 1:165-169 (1994); and Zhou et al., *J. Exp. Med.*, 179:1867-1875 (1994)). Additional suitable vectors include E1B gene-attenuated replicating adenoviruses described in, e.g., Kim et al., *Cancer Gene Ther.*, 9(9):725-36 (2002) and nonreplicating adenovirus vectors described in e.g., Pascual et al., *J. Immunol.*, 160(9):4465-72 (1998) Exemplary vectors can be constructed as disclosed by Okayama et al., *Mol. Cell. Biol.*, 3:280 (1983).

Molecular conjugate vectors, such as the adenovirus chimeric vectors described in Michael et al., *J. Biol. Chem.*, 268:6866-6869 (1993) and Wagner et al., *Proc. Natl. Acad. Sci. USA*, 89:6099-6103 (1992), can also be used for gene delivery according to the methods of the invention.

In one illustrative embodiment, retroviruses provide a convenient and effective platform for gene delivery systems. A selected nucleotide sequence encoding a polypeptide of the invention is inserted into a vector and packaged in retroviral particles using techniques known in the art. The recombinant virus can then be isolated and delivered to a subject. Suitable vectors include lentiviral vectors as described in e.g., Scherr et al., *Curr. Gene Ther.*, 2(1):45-55 (2002). Additional illustrative retroviral systems have been described (e.g., U.S. Pat. No. 5,219,740; Miller et al., *Bio Techniques*, 7:980-990 (1989); Miller, *Human Gene Therapy*, 1:5-14 (1990); Scarpa et al., *Virology*, 180:849-852 (1991); Burns et al., *Proc. Natl. Acad. Sci. USA*, 90:8033-8037 (1993); and Boris-Lawrie et al., *Curr. Opin. Genet. Develop.*, 3:102-109 (1993).

Other known viral-based delivery systems are described in, e.g., Fisher-Hoch et al., *Proc. Natl. Acad. Sci. USA*, 86:317-321 (1989); Flexner et al., *Ann. N.Y. Acad. Sci.*, 569:86-103 (1989); Flexner et al., *Vaccine*, 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques*, 6:616-627 (1988); Rosenfeld et al., *Science*, 252:431-434 (1991); Kolls et al., *Proc. Natl. Acad. Sci. USA*, 91:215-219 (1994); Kass-Eisler et al., *Proc. Natl. Acad. Sci. USA*, 90:11498-11502 (1993); Guzman et al., *Circulation*, 88:2838-2848 (1993); Guzman et al., *Cir. Res.*, 73:1202-1207 (1993); and Lotze et al., *Cancer Gene Ther.*, 9(8):692-9 (2002).

X. Use as Research Tools and in Methods of Diagnosis

The polypeptides and peptidomimetics of the invention are also useful as research tools. For example, the polypeptides or peptidomimetics of the invention can be used for investigating lipoprotein-receptor interactions in animals and animal models, particularly when a polypeptide or peptidomimetic thereof is labeled with a detectable moiety, e.g., a radioactive label, a fluorescent label, etc. In addition, the polypeptides of the invention can also be used to identify appropriate animal models for elucidation of lipid metabolic pathways. For example, the polypeptides can be used to identify animal models where lipid peroxidation contributes to the progression of atherosclerosis. Moreover, the polypeptides of the invention can be used to evaluate the anti-atherosclerotic potential of other compounds (including, e.g., polypeptide variants and other peptidomimetics).

In some cases, the polypeptides or peptidomimetics of the invention are used to target therapeutic agents to cells and tissues expressing ABCA.

In other embodiments, the polypeptides or peptidomimetics of the invention can be used in methods of diagnosing diseases and disorders associated with aberrant cholesterol efflux or with ABCA. For example, the peptides can be used in assays to diagnose reverse cholesterol transport deficiency and to identify individuals predicted to be responders to peptide treatment. Such diagnostic assays include in vitro assays. For example, cholesterol efflux can be evaluated in an assay in which a polypeptide of the invention, e.g., any one of NO:1-33, is mixed with plasma from a subject and exposed to cells to indicate whether a subject would respond to treatment (e.g., a large increase in efflux in the presence of the peptide compared with plasma-mediated efflux in the absence of the peptide suggests that the subject would be responsive). Similarly, a polypeptide of the invention, e.g., any one of SEQ ID NO:1-33, can be mixed with plasma from a subject to detect changes in HDL subclass distribution and/or to detect changes in anti-oxidative properties of the plasma in the presence of the peptide.

In some embodiments, the polypeptides or peptidomimetics are used for in vivo imaging methods. The polypeptides or peptidomimetics are conjugated to a detectable moiety and administered to a subject (e.g., a mammal such as a human). Detection of the detectable moiety allows imaging of a cell, tissue, or organ of interest, including, e.g., an atherosclerotic lesion or an amyloid plaque.)

The term "imaging" refers to a procedure or modality for generating an image of a detectable moiety in vivo, ex vivo, or in vitro as described herein or known to one of skill in the art. Examples of imaging modalities include, but are not limited to, magnetic resonance, nuclear magnetic resonance, radioscintigraphy, positron emission tomography, computed tomography, near-infrared fluorescence, X-ray, ultra sound, ultraviolet light, or visible light (see, e.g., Dahnhert, Radiology Review Manual (4th ed. 1999); Brant et al., Fundamentals of Diagnostic Radiobiology (2nd ed. 1999); Weissleder et al., Primer of Diagnostic Imaging (2nd ed. 1997); Buddinger et al., Medical Magnetic Resonance A Primer, Society of Magnetic Resonance, Inc. (1988); and Weissleder et al., *Nature Biotech.*, 17:375-378 (1999)).

The phrase "detectable moiety," as used herein, refers to a moiety or label that can be imaged and/or detected in vivo, ex vivo, or in vitro by a procedure or modality described herein or known to one of skill in the art. As used herein, the detectable moiety can be directly or indirectly linked to a polypeptide or peptidomimetic of the invention. A linker may serve to link the polypeptide or peptidomimetic to one detectable moiety. Alternatively, a linker may link the polypeptide to more than one detectable moiety. Likewise, a detectable moiety may be linked to more than one linker. The use of a plurality of detectable moieties attached to one polypeptide enables the detectability of the detectable moiety to be increased (e.g., by increasing its radiopacity, echogenicity or relaxivity) or, alternatively, it may enable the polypeptide to be detected in more than one imaging modality.

Linking of a detectable moiety to a polypeptide or peptidomimetic of the invention may be achieved by covalent or non-covalent means, usually involving interaction with one or more functional groups located on the detectable moiety, the linker and/or the polypeptide. Examples of chemically reactive functional groups that may be employed for this purpose include, but are not limited to, amino, hydroxyl, sulfhydryl, carboxyl, and carbonyl groups, as well as carbohydrate groups, vicinal dials, thioethers, 2-amino alcohols, 2-amino thiols, guanidinyl, imidazolyl and phenolic groups. In some embodiments, labile linkages, e.g., containing spacer arms that are biodegradable or chemically sensitive or which incorporate enzymatic cleavage sites, are used. The particular linker is not a critical aspect of the invention. Any linker known in the art may be used as long it binds the polypeptide or peptidomimetic and the detectable moiety together for an adequate period, i.e., a period sufficient for the polypeptide the desired target and be detected.

The detectable moieties used in the methods of the present invention can be any moiety capable of detection either directly or indirectly in an imaging procedure described herein or known to one of skill in the art. For example, the following detectable moieties may be used: moieties which emit or may be caused to emit detectable radiation (e.g., by radioactive decay, fluorescence excitation, spin resonance excitation, etc.), moieties which affect local electromagnetic fields (e.g., paramagnetic, superparamagnetic, ferrimagnetic or ferromagnetic species), moieties which absorb or scatter radiation energy (e.g., chromophores, particles (including gas or liquid containing vesicles), heavy elements and compounds thereof, etc.), and moieties which generate a detectable substance (e.g., gas microbubble generators).

A very wide range of materials detectable by imaging modalities is known from the art and the detectable moiety will be selected according to the imaging modality to be used. Thus, for example, for ultrasound imaging, an echogenic material or a material capable of generating an echogenic material will normally be selected; for X-ray imaging, the detectable moiety will generally be or contain a heavy atom (e.g., of atomic weight 38 or above); for MR imaging, the detectable moiety will either be a non zero nuclear spin isotope (such as $^{19}$F) or a material having unpaired electron spins and hence paramagnetic, superparamagnetic, ferrimagnetic or ferromagnetic properties; for light imaging, the detectable moiety will be a light scatterer (e.g., a colored or uncolored particle), a light absorber or a light emitter; for magnetometric imaging, the detectable moiety will have detectable magnetic properties; for electrical impedance imaging, the detectable moiety will affect electrical impedance; and for scintigraphy, SPECT, PET, etc., the detectable moiety will be a radionuclide.

Examples of suitable detectable moieties that are well known from the diagnostic imaging literature include, e.g., magnetic iron oxide particles, gas-containing vesicles, chelated paramagnetic metals (such as Gd, Dy, Mn, Fe, etc.) (see, for example, U.S. Pat. Nos. 5,228,446; 4,647,447; 4,863,715; 4,770,183, and 5,387,080; PCT Publication No. WO 97/25073, WO 96/09840, WO 85/02772, WO 92/17212, WO 97/29783, WO 91/15243, WO 93/05818, WO 96/23524, WO 95/26205 and WO 96/17628; EP-A-554213; and GB 9624918.0; metal radionuclides, paramagnetic metal ions, fluorescent metal ions, heavy metal ions and cluster ions as described in PCT Publication No. WO 91/14460, WO 89/00557, WO 92/17215, WO 96/40287 and WO 96/22914; and U.S. Pat. Nos. 4,647,447, 5,367,080 and 5,364,613; non-metal atomic moieties such as, e.g., $^{123}$I, $^{131}$I, and $^{18}$F, and heavy atoms such as I; organic chromophoric or fluorophoric moieties as described in Matsuoka, Topics in Applied Chemistry: Infrared absorbing dyes (1990); Waring et al., Topics in Applied Chemistry: The Chemistry and Application of Dyes (1990); "Handbook of Fluorescent Probes and Research Chemicals" Haugland, Molecular Probes Inc, 1996, DE-A-4445065, DE-A-4326466, JP-A-3/228046, Narayanan et al., *J. Org. Chem.*, 60:2391-2395 (1995), Lipowska et al., *Heterocyclic Comm.*, 1:427-430 (1995), Fabian et al., *Chem. Rev.*, 92:1197 (1992); PCT Publication No. W096/23525: Strekowska et al., *J. Org. Chem.*, 57:4578-4580 (1992); and PCT Publication No. WO 96/17628; visible dyes as described in, Waring and Hallas, The Chemistry and Application of Dyes, Topics in Applied Chemistry (1990); Haugland, Handbook of Fluorescent Probes and Research Chemicals (6th ed. 1996).

Examples of imaging modalities suitable for detecting the detectable moiety linked to the ligand include, but are not limited to, magnetic resonance, nuclear magnetic resonance, radioscintigraphy, positron emission tomography, computed tomography, near-infrared fluorescence, X-ray, ultra sound, ultraviolet light, or visible light, wherein the image of the detectable moiety is indicative of the activity of a specific extracellular protease (see, for example, Dahnhert, Radiology Review Manual (4th ed. 1999); Brant et al., Fundamentals of Diagnostic Radiobiology, (2nd ed. 1999); Weissleder et al., Primer of Diagnostic Imaging, (2nd ed. 1997); Buddinger et al., Medical Magnetic Resonance A Primer, Society of Magnetic Resonance, Inc. (1988); and Weissleder et al., *Nature Biotech.*, 17:375-378 (1999)).

In certain circumstances, it may be desirable that the linker biodegrade after administration. By selecting an appropriately biodegradable linker, it is possible to modify the biodistribution and bioelimination patterns for the polypeptide and/or detectable moiety. Where polypeptide and/or detectable moiety are biologically active or are capable of exerting undesired effects if retained after the imaging procedure is over, it may be desirable to design biodegradability into the linker that ensures appropriate bioelimination or metabolic breakdown of the polypeptide and/or detectable moieties. Thus, a linker may contain a biodegradable function that on breakdown yields breakdown products with modified biodistribution patterns that result from the release of the detectable moiety from the polypeptide or from fragmentation of a macromolecular structure. By way of example, for linkers that carry chelated metal ion moieties, it is possible to have the linker incorporate a biodegradable function that on breakdown releases an excretable chelate compound containing the detectable moiety. Accordingly, biodegradable functions may, if desired, be incorporated within the linker structure, preferably at sites which are (a) branching sites, (b) at or near attachment sites for ligands or detectable moieties, or (c) such that biodegradation yields physiologically tolerable or rapidly excretable fragments.

XI. Kits

In another aspect, the present invention provides kits for the treatment, i.e., amelioration, or prevention of a disease or disorder, i.e., condition, associated with dyslipidemia, hypercholesterolemia and inflammation. In a preferred embodiment, the present invention provides kits for the treatment, i.e., amelioration, of one or more symptoms of atherosclerosis or for the prophylactic treatment of a subject (e.g., human or animal) at risk for atherosclerosis. The kits preferably comprise a container containing one or more of the polypeptides (or peptidomimetics) of this invention. The polypeptide or peptidomimetic can be provided in a unit dosage formulation (e.g., tablet, caplet, patch, suppository, etc.) and/or can be optionally combined with one or more pharmaceutically acceptable excipients.

The kit can, optionally, further comprise one or more other agents used in the treatment of a disease or condition associated with dyslipidemia, hypercholesterolemia and inflammation (such as heart disease and/or atherosclerosis). Such agents include, but are not limited to, those set forth above in connection with the section on "Combination Therapy." For instance, in certain embodiments, the kit can include beta blockers, vasodilators, aspirin, statins, ace inhibitors or ace receptor inhibitors (ARBs) and the like.

In addition, the kits can optionally include labeling and/or instructional materials providing directions (i.e., protocols) for the practice of the methods or use of the "therapeutics" or "prophylactics" of this invention. Preferred instructional materials describe the use of one or more polypeptides or peptidomimetics of this invention, for example, to mitigate one or more symptoms of atherosclerosis and/or to prevent the onset or increase of one or more of such symptoms in an individual at risk for atherosclerosis. The instructional materials can also, optionally, teach preferred dosages/therapeutic regiment, counter indications and the like.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips, etc.), optical media (e.g., CD ROM), and the like. Such media may include addresses to internet sites that provide such instructional materials.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

XII. Examples

Example 1

Cholesterol Efflux Activity of 22-Mer Peptides

The peptides are listed in groups reflecting changes in composition made to increase efficiency in stimulating ABCA1 cholesterol efflux. The sequences are identified by numbers that correspond to synthesis lot numbers.

257-11 corresponds to a 22-mer peptide successfully engineered with biological activity. The amino acid sequence of peptide N257-11 is ELREKLEAWREAFEEFFARFKS (SEQ ID NO:34) (FIG. 1, which shows a helical wheel diagram of the peptide). N257-11 stimulated ABCA1 cholesterol efflux with generally high capacity, although high concentrations were required for activity and thus the peptide displayed weak efflux efficiency.

Peptide Series #: N257-11,
22-mer peptide with ABCA1 cholesterol efflux activity

```
ELREKLEAWREAFEEFFARFKS       SEQ ID NO: 34
```

| | 8 hour efflux data (J774 macrophages ± cAMP to upregulate ABCA1) % cholesterol efflux (8 hours) | |
|---|---|---|
| No cAMP | 0.91 ± 0.1 | Peptide stimulates ABCA1-cholesterol efflux |
| + cAMP | 6.99 ± 1.4 | Km approx 10-20 μg/ml |

Example 2

Cholesterol Efflux Activity of 20-mer, 21-mer, and 22-mer Peptides

Peptides comprising series N356 were designed with amino acid substitutions to increase the cholesterol efflux efficiency of the parent N257-11 peptide. One substitution (R10→F, N356-1 peptide) was intended to expand the non-polar surface to 140 degrees; this disrupted one of the putative salt-bridges in the parent peptide. The changes produced peptides that were more potent than N257-11 in stimulating cholesterol efflux, although the concentration dependence curves displayed a threshold-type response uncharacteristic of native proteins.

Peptides in series N965 were based on a composite design of series N257 and N356 and were engineered to maintain salt-bridge configurations, a broad non-polar surface and key topographical aspects of acidic residues on the polar surface. Subsequent engineering (N1154 series) lead to the surprising finding that a relatively few choices of amino acids can be used to artificially engineer biologically active peptides, including the use of all Leucine residues to replace all Phenylalanine residues.

TABLE A

Peptide Series #: N356, 22-, 21- and 20-mer peptides based on N257-11 design
Substitutions designed to increase efficiency of cholesterol efflux. ELREKLEAWREAFEEFFARFKS
SEQ ID NO: 34 parent N257-11 sequence (listed above)

| Sequence | series # | number of amino acids | SEQ ID NO: |
|---|---|---|---|
| ELREKLEAWFEAFEEFFARFKS | N356-1 | 22-mer | 35 |
| ELREKLEAWRELFEEFFARFKS | N356-2 | 22-mer | 36 |
| ELREKLEAWFELFEEFFARFKS | N356-3 | 22-mer | 37 |
| ELREKLEAWFELAEFFARFKS | N356-4 | 22-mer | 38 |
| ELREKLEAWFELAEFFARFK | N356-5 | 21-mer | 39 |
| ELREKLEAWFELAEFFARF | N356-6 | 20-mer | 40 |
| ELRAKLEAWFEAAEFFARF | N356-7 | 20-mer | 41 |

The underlined residues represent changes made to the first sequence in the list (i.e. N257-11).

| | % cholesterol efflux/8 hours | | | | | | |
|---|---|---|---|---|---|---|---|
| | N356-1 | N356-2 | N356-3 | N356-4 | N356-5 | N356-6 | N356-7 |
| No cAMP | 0.86 ± 0.06 | 1.27 ± 0.14 | 0.82 ± 0.07 | 1.72 ± 0.14 | 2.18 ± 0.17 | 2.09 ± 0.15 | 2.78 ± 0.40 |
| Plus cAMP | 4.16 ± 0.38 | 6.52 ± 0.37 | 3.94 ± 0.50 | 4.25 ± 0.60 | 5.97 ± 0.47 | 4.04 ± 0.72 | 7.00 ± 0.94 |

Concentration dependence (cholesterol efflux efficiency)

| | % cholesterol efflux/4 hours | | | | | | |
|---|---|---|---|---|---|---|---|
| μg/ml | N356-1 | N356-2 | N356-3 | N356-4 | N356-5 | N356-6 | N356-7 |
| 0.1 | 0 | 0 | 0 | 0.14 | 0.02 | 0.01 | 0.15 |
| 0.3 | 0 | 0 | 0.57 | 0.61 | 0.31 | 0.23 | 0.23 |
| 1.0 | 0.23 | 0.02 | 1.20 | 1.89 | 1.59 | 0.67 | 1.17 |
| 3.0 | 4.71 | 1.30 | 4.34 | 5.68 | 4.27 | 4.07 | 4.99 |
| 10 | 5.61 | 5.70 | 5.13 | 6.06 | 3.86 | 3.78 | 5.49 |
| 30 | 3.50 | 5.92 | 3.24 | 6.52 | 3.20 | 3.91 | 5.66 |

TABLE B

Peptide Series #: N965, 22-, 21- and 20-mer peptides based on N257-11 & N365 designs

| Sequence | series # | number of amino acids | SEQ ID NO: |
|---|---|---|---|
| EVREKLEAWFEAFREFAERFKS | N965-1 | 22-mer | 42 |
| EVREKLEAWFELFREFAERFKS | N965-2 | 22-mer | 43 |
| EVREKLEAWFELFREFAERFLS | N965-3 | 22-mer | 44 |
| EVREKLEAWFELFREFLERFKS | N965-4 | 22-mer | 45 |
| EVREKLEAWFELFREFLERFLS | N965-5 | 22-mer | 46 |
| EVREKLEAWFELFREFLERFL | N965-6 | 21-mer | 47 |
| EVREKLEAWFELFREFLERF | N965-7 | 20-mer | 48 |
| ELREKLEAWFELFREFLERF | N965-8 | 20-mer | 49 |
| ELREKLEAWRELFEEFFARFLS | N965-9 | 22-mer | 50 |

TABLE C

Peptide Series #: N1154 20-mer peptides based on N965-8 ELREKLEAWFELFREFLERF SEQ ID NO: 49 parent N965-8 (ATI-185)

| Sequence | series # | number of amino acids | SEQ ID NO: |
|---|---|---|---|
| ELRERLEAWFELFREFLERF | N1154-1 | 20-mer | 51 |
| ELRDKLEAWFDLFREFLERF | N1154-2 | 20-mer | 52 |
| DLRDKLDAWFDLFRDFLDRF | N1154-3 | 20-mer | 53 |
| ELRDRLEAWFDLFREFLERF | N1154-4 | 20-mer | 54 |
| DLRDRLDAWFDLFRDFLDRF | N1154-5 | 20-mer | 55 |
| ELREKLEAWLELLRELLERL | N1154-6 | 20-mer | 56 |
| ELRERLEAWLELLRELLERL | N1154-7 | 20-mer | 57 |
| ELRDKLEAWLDLLRELLERL | N1154-8 | 20-mer | 58 |
| DLRDKLDAWLDLLRDLLDRL | N1154-9 | 20-mer | 59 |
| ELRDRLEAWLDLLRELLERL | N1154-10 | 20-mer | 60 |
| DLRDRLDAWLDLLRDLLDRL | N1154-11 | 20-mer | 61 |

The underlined residues represent changes made to the first sequence in the list (i.e. N965-1)

Results

N965 peptide series: Cholesterol efflux data (J774 macrophages+cAMP, upregulates ABCA1)

The underlined residues represent changes made to ATI-185.

Results

N1154 peptides 1-5: Cholesterol efflux data (J774 macrophages+cAMP, upregulates ABCA1)

| | % cholesterol efflux/8 hours | | | | | | | | |
|---|---|---|---|---|---|---|---|---|---|
| | N965-1 | N965-2 | N965-3 | N965-4 | N965-5 | N965-6 | N965-7 | N965-8 | N965-9 |
| −cAMP | 1.75 ± 0.20 | 1.28 ± 0.18 | 1.45 ± 0.12 | 1.52 ± 0.07 | 2.91 ± 0.44 | 3.15 ± 0.36 | 1.50 ± 0.14 | 2.29 ± 0.16 | 1.06 ± 0.19 |
| +cAMP | 9.90 ± 1.04 | 6.97 ± 0.77 | 3.85 ± 0.65 | 4.76 ± 0.33 | 5.52 ± 0.38 | 6.18 ± 0.34 | 4.03 ± 0.37 | 5.26 ± 0.95 | 2.94 ± 0.34 |

Concentration dependence (cholesterol efflux efficiency)

| | % cholesterol efflux/4 hours | | | | | | | | |
|---|---|---|---|---|---|---|---|---|---|
| μg/ml | N965-1 | N965-2 | N965-3 | N965-4 | N965-5 | N965-6 | N965-7 | N965-8 | N965-9 |
| 0.1 | 0 | 0 | 0.23 | 0.29 | 0.12 | 0.11 | 0.03 | 0.15 | 0.03 |
| 0.3 | 0.13 | 0.13 | 0.47 | 0.67 | 0.90 | 0.49 | 0.30 | 0.52 | 0.41 |
| 1.0 | 0 | 0.01 | 1.06 | 2.70 | 2.13 | 1.59 | 1.39 | 1.72 | 0.72 |
| 3.0 | 0.44 | 2.23 | 3.48 | 4.72 | 4.89 | 1.98 | 4.94 | 4.60 | 2.45 |
| 10 | 2.90 | 5.96 | 3.05 | 4.00 | 4.06 | 2.22 | 3.65 | 3.62 | 1.77 |
| 30 | 6.01 | 3.98 | 2.53 | 2.94 | 3.82 | 2.75 | 2.66 | 3.66 | 1.41 |

| | % cholesterol efflux/8 hours | | | | |
|---|---|---|---|---|---|
| | N1154-1 | N1154-2 | N1154-3 | N1154-4 | N1154-5 |
| No cAMP | 1.85 ± 0.28 | 1.47 ± 0.15 | 1.61 ± 0.34 | 2.59 ± 0.35 | 3.06 ± 1.01 |
| Plus cAMP | 5.20 ± 0.25 | 3.00 ± 0.21 | 3.29 ± 0.44 | 11.4 ± 0.70 | 9.88 ± 0.53 |

Concentration dependence (cholesterol efflux efficiency)

| | % cholesterol efflux/4 hours | | | | |
|---|---|---|---|---|---|
| μg/ml | N1154-1 | N1154-2 | N1154-3 | N1154-4 | N1154-5 |
| 0.1 | 0.10 | 0.03 | 0 | 0 | 0 |
| 0.3 | 0.41 | 0.51 | 0.19 | 1.30 | 1.92 |
| 1.0 | 2.06 | 2.17 | 1.31 | 3.51 | 2.77 |
| 3.0 | 5.11 | 2.59 | 2.66 | 4.14 | 5.28 |
| 10 | 4.44 | 2.14 | 2.12 | 5.02 | 5.29 |
| 30 | 3.67 | 1.66 | 2.21 | 3.65 | 3.53 |

N1154 peptides 6-11: Cholesterol efflux data (J774 macrophages+cAMP, upregulates ABCA1)

| | % cholesterol efflux/8 hours | | | | | |
|---|---|---|---|---|---|---|
| | N1154-6 | N1154-7 | N1154-8 | N1154-9 | N1154-10 | N1154-11 |
| No cAMP | 1.17 ± 0.09 | 1.23 ± 0.10 | 1.31 ± 0.08 | 1.81 ± 0.14 | 2.66 ± 0.41 | 4.20 ± 0.75 |
| Plus cAMP | 4.29 ± 0.68 | 4.14 ± 0.84 | 4.38 ± 0.43 | 4.83 ± 0.32 | 8.25 ± 0.33 | 9.04 ± 1.96 |

Concentration dependence (cholesterol efflux efficiency)

| | % cholesterol efflux/4 hours | | | | | |
|---|---|---|---|---|---|---|
| μg/ml | N1154-6 | N1154-7 | N1154-8 | N1154-9 | N1154-10 | N1154-11 |
| 0.1 | 0.18 | 0.23 | 0 | 0.08 | 0.58 | 0.58 |
| 0.3 | 0.46 | 0.83 | 0.48 | 0.43 | 1.00 | 1.34 |
| 1.0 | 2.51 | 2.26 | 1.51 | 1.81 | 2.12 | 2.56 |
| 3.0 | 4.73 | 4.14 | 3.41 | 3.48 | 5.25 | 4.84 |
| 10 | 3.56 | 3.24 | 2.99 | 3.31 | 4.15 | 4.17 |
| 30 | 2.71 | 3.28 | 3.02 | 4.35 | 3.70 | 5.55 |

Example 3

Figure 2:
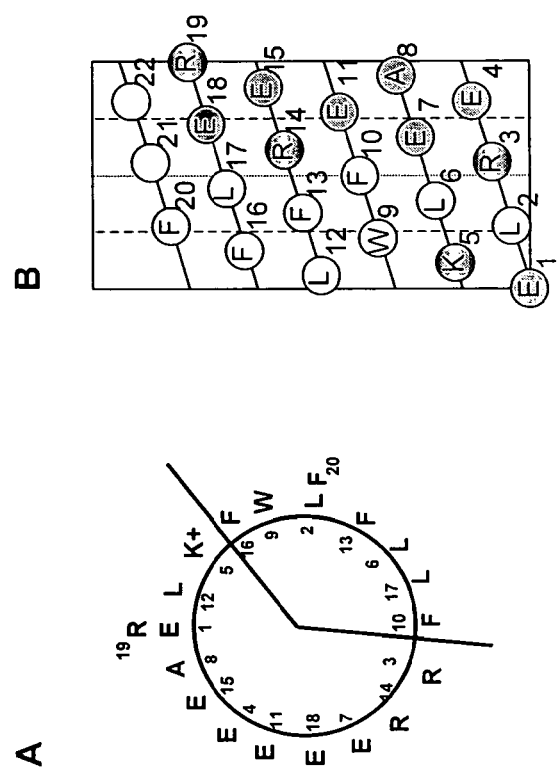
FIG. 2 shows a helical wheel diagram and helical net diagram of a peptide of the invention, SEQ ID NO:2. Panel A shows a helical wheel diagram showing amphipathic nature of the peptide. Panel B shows a helical net diagram showing the peptide cut down the long axis of the polar surface and flattened. Shaded circles indicate acidic amino acids and partially shaded circles cationic residues. Numbers in both panels refer to the primary sequence of amino acids.

The primary amino acid sequence and projected α-helical structure of potent ABCA1 cholesterol efflux peptide SEQ ID NO:2 (20-mer) (FIG. 2). Panel A shows α helical wheel diagram showing amphipathic nature of the peptide. Panel B shows α helical net diagram showing the peptide cut down the long axis of the polar surface and flattened. Shaded circles indicate acidic amino acids and partially shaded circles cationic residues. Numbers in both panels refer to the primary sequence of amino acids.

Example 4

Figure 3:
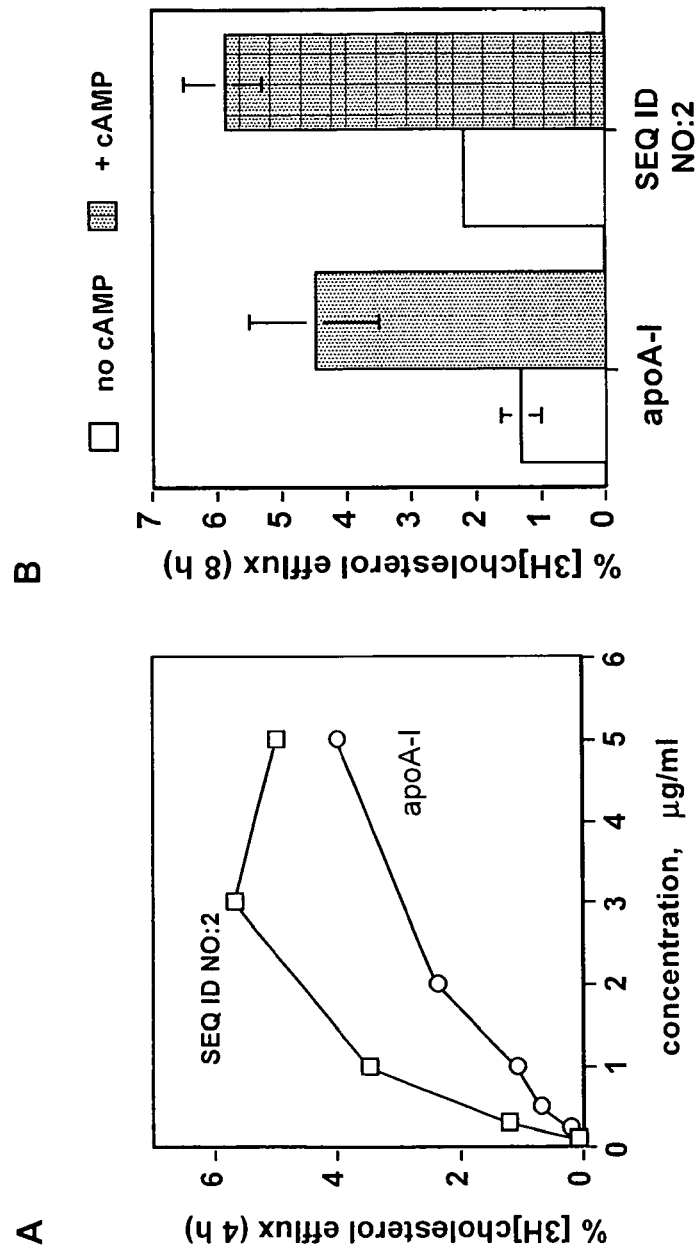
FIG. 3 provides data showing the cholesterol efflux activity of SEQ ID NO:2 vs. full-length apoA-I. Panel A shows the dependence of cholesterol efflux on concentration (lipid-free SEQ ID NO:2 peptide (squares); lipid-free apolipoprotein (apo)A-I (circles)). Panel B shows the dependence of cholesterol efflux on ABCA1 expression determined using cells treated with and without cAMP.

This examples shows the cholesterol efflux activity of SEQ ID NO:2 vs. full-length apoA-I. J774 macrophages labeled with [$^3$H]cholesterol were used to evaluate the cholesterol efflux activity of peptides of the present invention. J774 cells plated on 24-well culture plates were labeled (48 h) with 1 μCi/ml of [$^3$H]cholesterol in 1% FBS. A cAMP analog was added (0.3 mM) to some wells (12-18 h) to up-regulate ABCA1 expression. Following cAMP treatment, cells were rinsed, and then exposed to peptide in serum-free medium. The results are shown in FIG. 3. Panel A provides data showing the dependence of cholesterol efflux on concentration (lipid-free SEQ ID NO:2 peptide (squares) and lipid-free apolipoprotein(apo)A-I (circles)); cAMP-treated cells were used. The percentage of cellular [$^3$H]cholesterol that appeared in the medium at 8 h is shown, subtracting background efflux to serum-free medium alone. Values are means±SD; apoA-I, n=8; SEQ ID NO:2 peptide, n=3. Km values reflecting efficiency for cholesterol efflux stimulation were calculated (Prism 4 software) from concentration-dependence curves using the Michaelis-Menton equation and 4 h efflux data. The SEQ ID NO:2 peptide stimulated cholesterol efflux ~5-fold more efficiently compared to apoA-I on a mass basis (Km=0.7±0.3 vs. apoA-I Km=3.4±0.6 μg/ml, respectively). On a molar basis, the efflux efficiency of the peptide was nearly equivalent to apoA-I (Km=0.26±0.11 vs. apoA-I Km=0.12±0.02).

Panel B of FIG. 3 shows that lipid-free SEQ ID NO:2 peptide stimulated cholesterol efflux in an ABCA1-dependent manner, similar to apoA-I. J774 cells labelled with [$^3$H] cholesterol and treated with (shaded bars) and without (open bars) cAMP were exposed to SEQ ID NO:2 peptide or apoA-I; both at a concentration of 30 μg/ml. Percent cholesterol efflux to medium (8 h) is shown. The values are representative of two experiments.

Example 5

This example demonstrates that a 22-mer analog of SEQ ID NO:2 with residues KS added to the C-terminus stimulates ABCA1 cholesterol efflux, similar to 20-mer SEQ ID NO:2 peptide.

```
SEQ ID NO: 2      ELREKLEAWFELFREFLERF
SEQ ID NO: 31     ELREKLEAWFELFREFLERFKS
```

Figure 4:
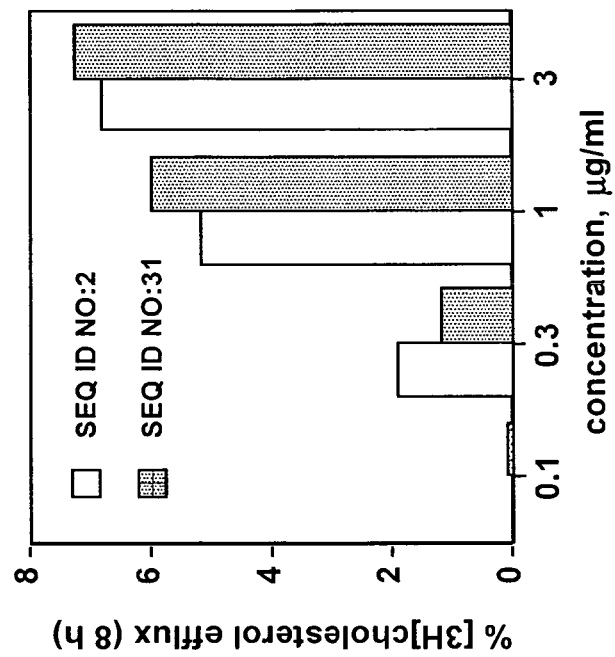
FIG. 4 provides data showing that a 22-mer analog of SEQ ID NO:2 with residues KS added to the C-terminus stimulates ABCA1 cholesterol efflux.

J774 cells labeled with [$^3$H]cholesterol and treated with cAMP (0.3 mM) were rinsed and exposed to lipid-free peptides in serum-free medium, as described in Example 4. The results are shown in FIG. 4. The percentage of cellular [$^3$H] cholesterol that appeared in the medium (8 h) in response to either the SEQ ID NO:2 peptide (open bars) or SEQ ID NO:31 peptide (shaded bars) is shown. Values are from a single experiment. Duplicate wells were used for each concentration. Duplicates differed by no more than twelve percent.

Example 6

This example demonstrates that leucine (L) or phenylalanine (F) can substitute for tryptophan (W) in a 20-mer peptide (SEQ ID NO:2) without adversely affecting ABCA1 cholesterol efflux activity

```
SEQ ID NO: 32      ELREKLEALFELFREFLERF
SEQ ID NO: 33      ELREKLEAFFELFREFLERF
```

Figure 5:
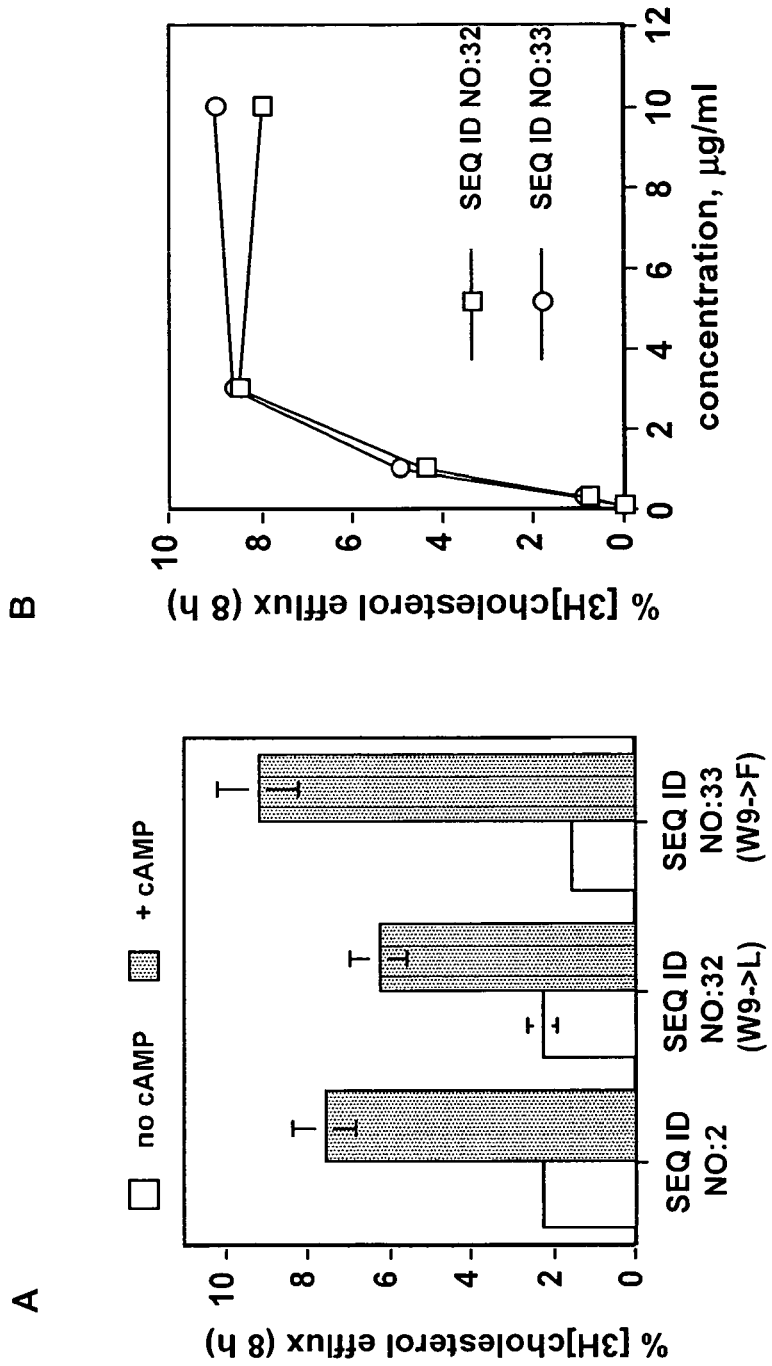
FIG. 5 provides data that demonstrates that leucine (L) or phenylalanine (F) can substitute for tryptophan (W) in SEQ ID NO:2 without adversely affecting ABCA1 cholesterol efflux activity. Panel A shows the percentage of cellular [$^3$H] cholesterol that appeared in the medium in response to treatment with the indicated peptides. Panel B shows the dependence of cholesterol efflux on the concentration of peptide.

J774 cells were labelled with [³H]cholesterol and exposed to peptides as described in Example 4. Panel A (FIG. 5) shows the percentage of cellular [³H]cholesterol appearing in the medium (8 h) in response to SEQ ID NO:2, SEQ ID NO:32, and SEQ ID NO:33 peptides. Peptides were used in lipid-free form at 30 µg/ml serum-free medium. Values are from a single experiment, using triplicate wells for each peptide/condition. Means±SD are shown. Peptides stimulated relatively high-levels of cholesterol efflux from cells induced for the ABCA1 response (i.e. +cAMP, shaded bars), compared to low levels with no cAMP (open bars). Panel B shows the dependence of cholesterol efflux on the concentration of SEQ ID NO:32 and SEQ ID NO:33 peptides; cAMP treated cells were used. Values are from single experiment with duplicate wells for each condition.

Example 7

Figure 6:
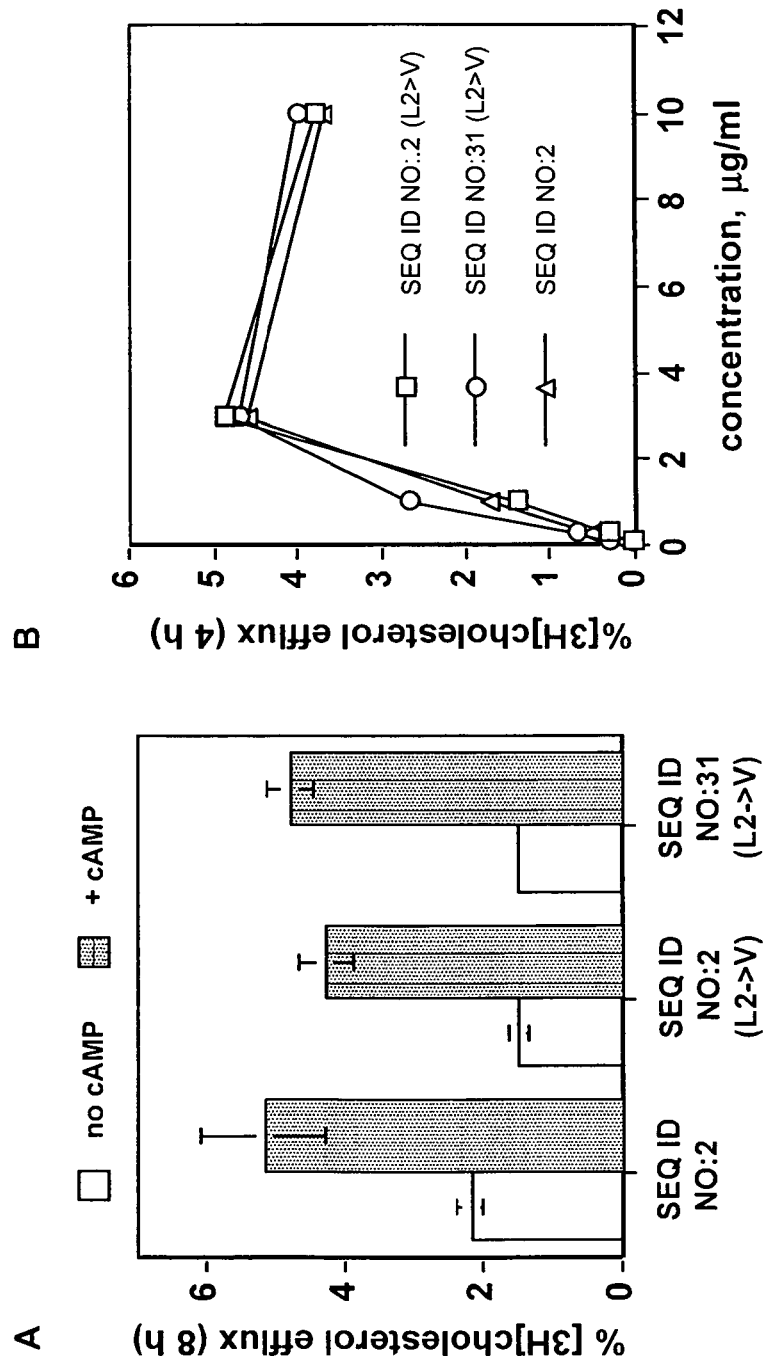
FIG. 6 provides data showing that valine can substitute for leucine on the non-polar surface of cholesterol efflux peptides without adversely affecting activity. Panel A shows the percentage of cellular [$^3$H]cholesterol that appeared in the medium (8 h) in response to treatment with the indicated peptides. Panel B shows the dependence of cholesterol efflux on concentration of peptides.

This example shows that valine can substitute for leucine on the non-polar surface of cholesterol efflux peptides without adversely affecting activity. J774 cells were labelled with [³H]cholesterol as described in Example 4. The results of the analysis are shown in FIG. 6. Panel A shows the percentage of cellular [³H]cholesterol that appeared in the medium (8 h) in response to SEQ ID NO:2 (20-mer) and SEQ ID NO:31 (22-mer) peptides, each containing valine (V) for leucine (L) at position two in primary sequence. Peptides were used in lipid-free form at 30 µg/ml serum-free medium. Values are from a single experiment, using triplicate wells for each peptide/condition. Means±SD are shown. Peptides stimulated relatively high-levels of cholesterol efflux from cells induced for the ABCA1 response (i.e. +cAMP, shaded bars), compared to low levels with no cAMP (open bars). Panel B provides data showing the dependence of cholesterol efflux on concentration of peptides (indicated by legend); cAMP treated cells were used. Values are from single experiment with duplicate wells for each condition.

Example 8

This example shows that stimulation of ABCA1 cholesterol efflux is influenced by the number of hydrophobic leucine residues in the peptide.

Figure 7:
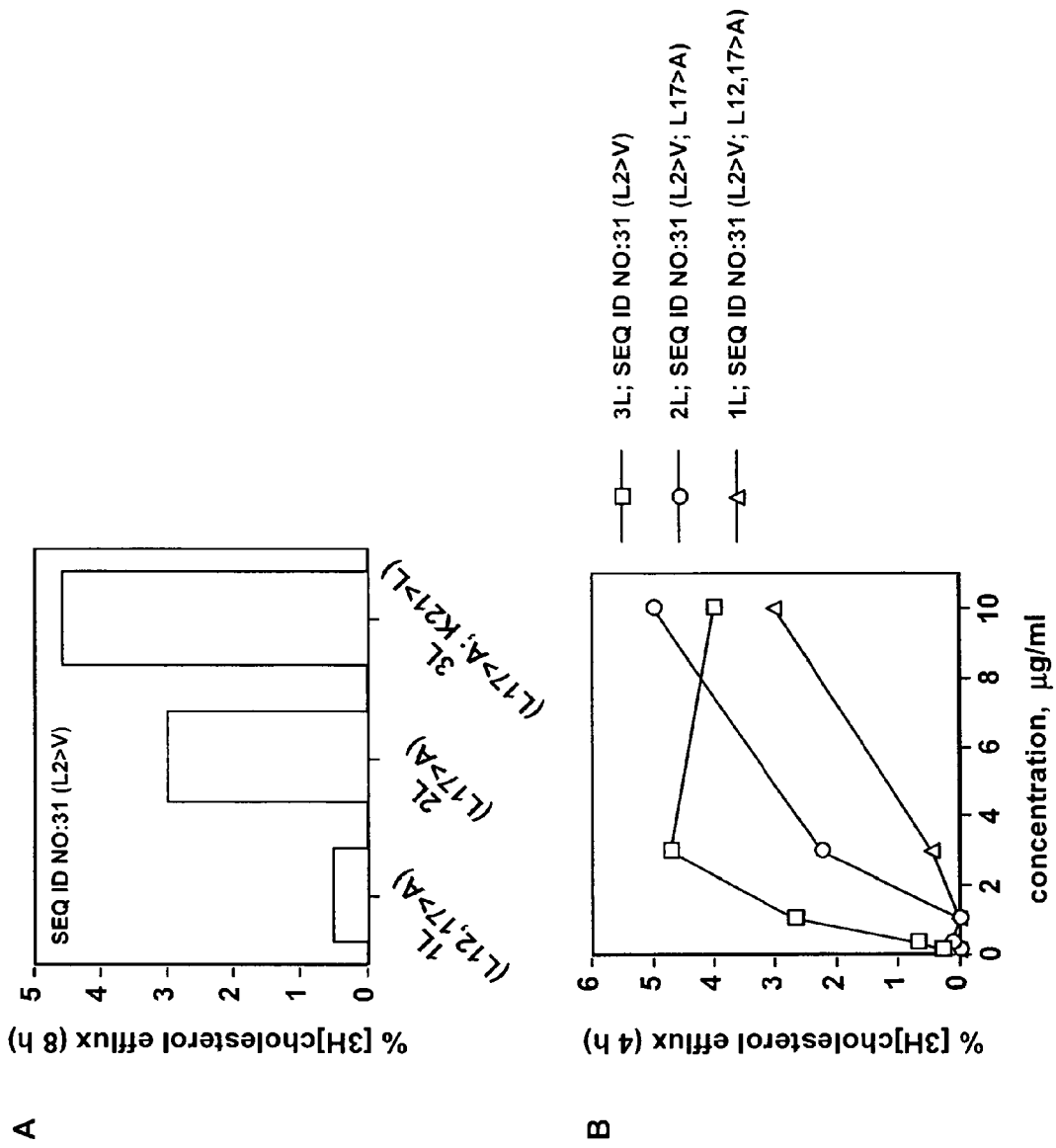
FIG. 7 providing data showing that stimulation of ABCA1 cholesterol efflux is influenced by the number of hydrophobic leucine residues in the peptide. Panel A shows the percentage of cellular [$^3$H]cholesterol that appeared in the medium in response to treatment with the indicated peptides. Panel B shows the dependence of cholesterol efflux on concentration of the peptides.

J774 cells were labeled with [3H]cholesterol as described in Example 4. Experiments were conducted by substituting Alanine (A) for Leucine (L) at important positions, 12 and 17, in the SEQ ID NO:31 peptide. The results are shown in FIG. 7. Panel A provides data showing the percentage of cellular [³H]cholesterol that appeared in the medium (8 h) in response to peptides; the control peptide corresponds to SEQ ID NO:31 containing V for L at position 2 (squares); this peptide contains a total of 3 leucine (L) residues. Peptides with 3 and 4 L residues possessed identical cholesterol efflux activity (FIG. 6, i.e. SEQ ID NO:2 with and without L2>V). In contrast, peptides with fewer than three L residues stimulated cholesterol efflux poorly. Panel B provides data showing the dependence of cholesterol efflux on concentration of peptides. As indicated, the number of hydrophobic L residues conferred cholesterol efflux efficiency for peptide of the present invention; cAMP treated cells were used.

Example 9

This examples demonstrates that peptides of the present invention can be engineered with leucine residues or combinations of leucine and isoleucine residues on the non-polar surface without adversely affecting ABCA1 cholesterol efflux activity.

Figure 8:
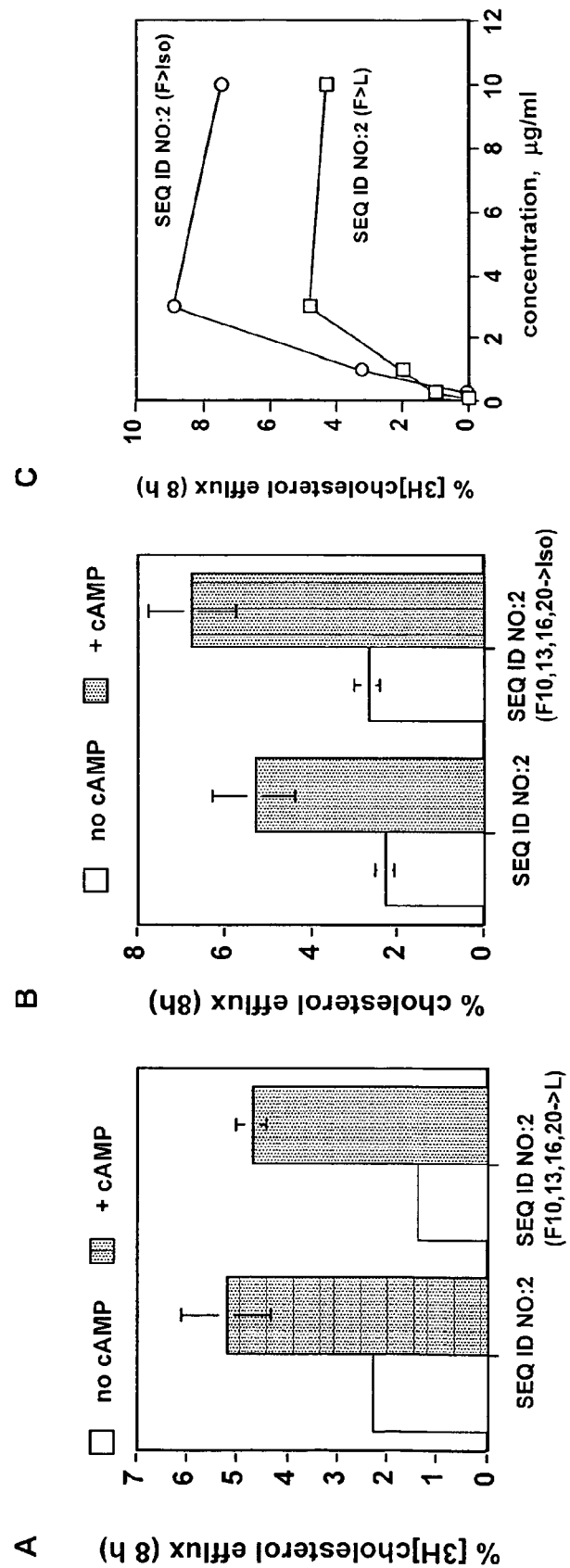
FIG. 8 provides data showing that peptides of the invention can be engineered with leucine residues or combinations of leucine and isoleucine residues on the non-polar surface without adversely affecting ABCA1 cholesterol efflux activity. Panels A and B show the percentage of cellular [$^3$H]cholesterol that appeared in the medium in response to treatment with the indicated peptide. Panel C shows the dependence of cholesterol efflux on concentration of the peptides.

J774 cells were labelled with [³H]cholesterol as described in Example 4. Experiments were conducted by substituting either isoleucine (I) or leucine (L) for hydrophobic phenylalanine (F) residues on the non-polar surface of the SEQ ID NO:2 peptide. The F>L substitutions create a peptide displaying a non-polar surface with all L residues (except W9). The results are shown in FIG. 8. Panel A shows the percentage of cellular [³H]cholesterol that appeared in the medium (8 h) in response to SEQ ID NO:2 peptide versus SEQ ID NO:2 with F>L substitutions. Panel B shows an experiment similar to that in panel A, except a SEQ ID NO:2 peptide with F>I substitutions was used. Peptides in both panels A and B were used in lipid-free form at 30 µg/ml serum-free medium. Panel C shows the dependence of cholesterol efflux on concentration of peptides, indicating that stimulation of ABCA1 cholesterol efflux is not dependent on aromatic (phenylalanine) residues; cAMP treated cells were used.

Example 10

This examples demonstrates that peptides of the present invention can be engineered with increasing numbers of phenylalanine residues on the non-polar surface without adversely affecting ability to stimulate ABCA1 cholesterol efflux.

Figure 9:
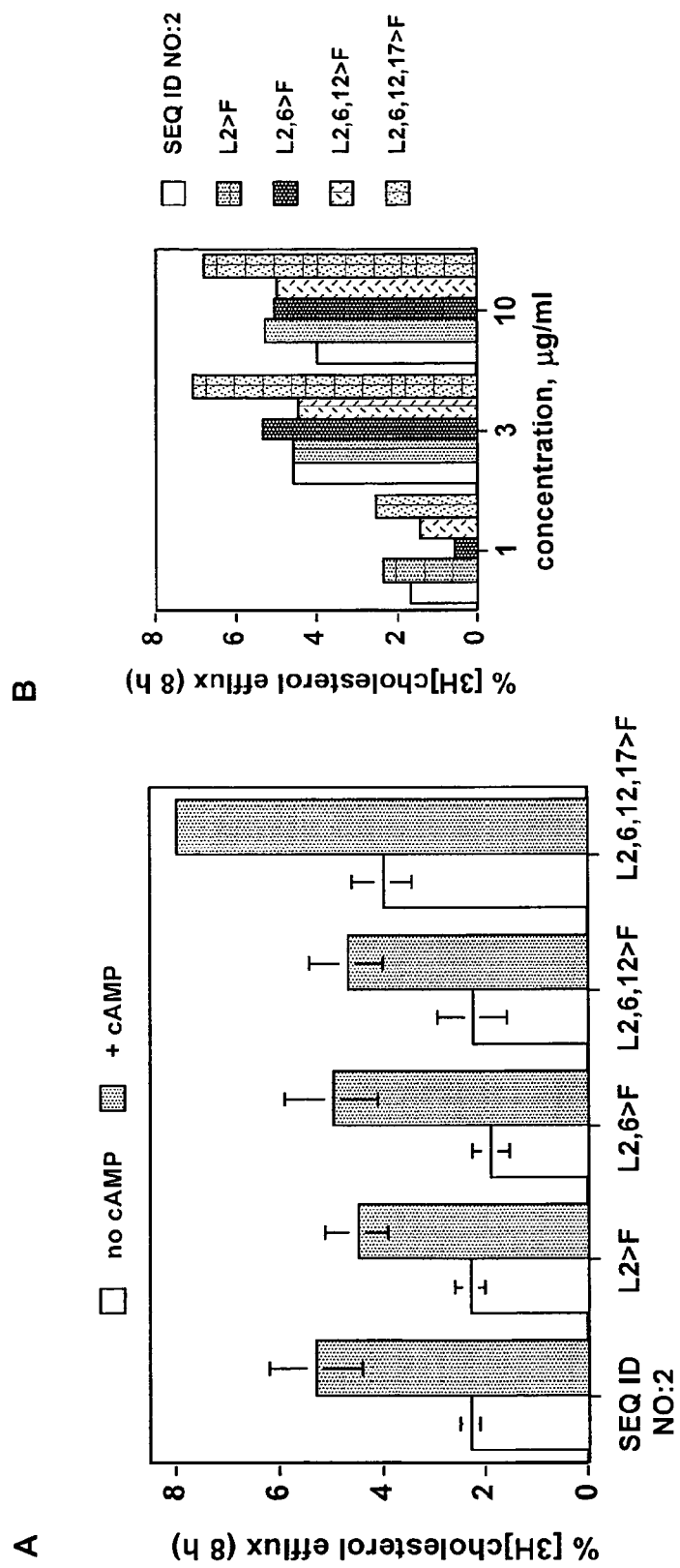
FIG. 9 provides data showing that peptides of the invention can be engineered with increasing numbers of phenylalanine residues on the non-polar surface without adversely affecting ability to stimulate ABCA1 cholesterol efflux. Panel A shows the percentage of cellular [$^3$H]cholesterol that appeared in the medium in response to treatment with the indicated peptide. Panel B shows the dependence of cholesterol efflux on the concentration of peptides.

J774 cells were labelled with [³H]cholesterol as described in Example 4. Experiments were conducted by substituting hydrophobic phenylalanine (F) residues for leucine (L) on the non-polar surface of the SEQ ID NO:2 peptide. The L>F substitutions at positions 2, 6, 12, and 17 create a peptide displaying a non-polar surface with all F residues (except W9). The results are shown in FIG. 9. Panel A shows the percentage of cellular [³H]cholesterol that appeared in the medium (8 h) in response to SEQ ID NO:2 peptide versus SEQ ID NO:2 with L>F substitutions. Peptides were used in lipid-free form at 30 µg/ml serum-free medium. Panel B shows the dependence of cholesterol efflux on the concentration of SEQ ID NO:2 peptides, with and without L>F substitutions; cAMP treated cells were used.

Example 11

This examples demonstrates that leucine and phenylalanine residues of peptides of the invention can be replaced with isoleucine without adversely affecting ability to stimulate ABCA1 cholesterol efflux.

Figure 10:
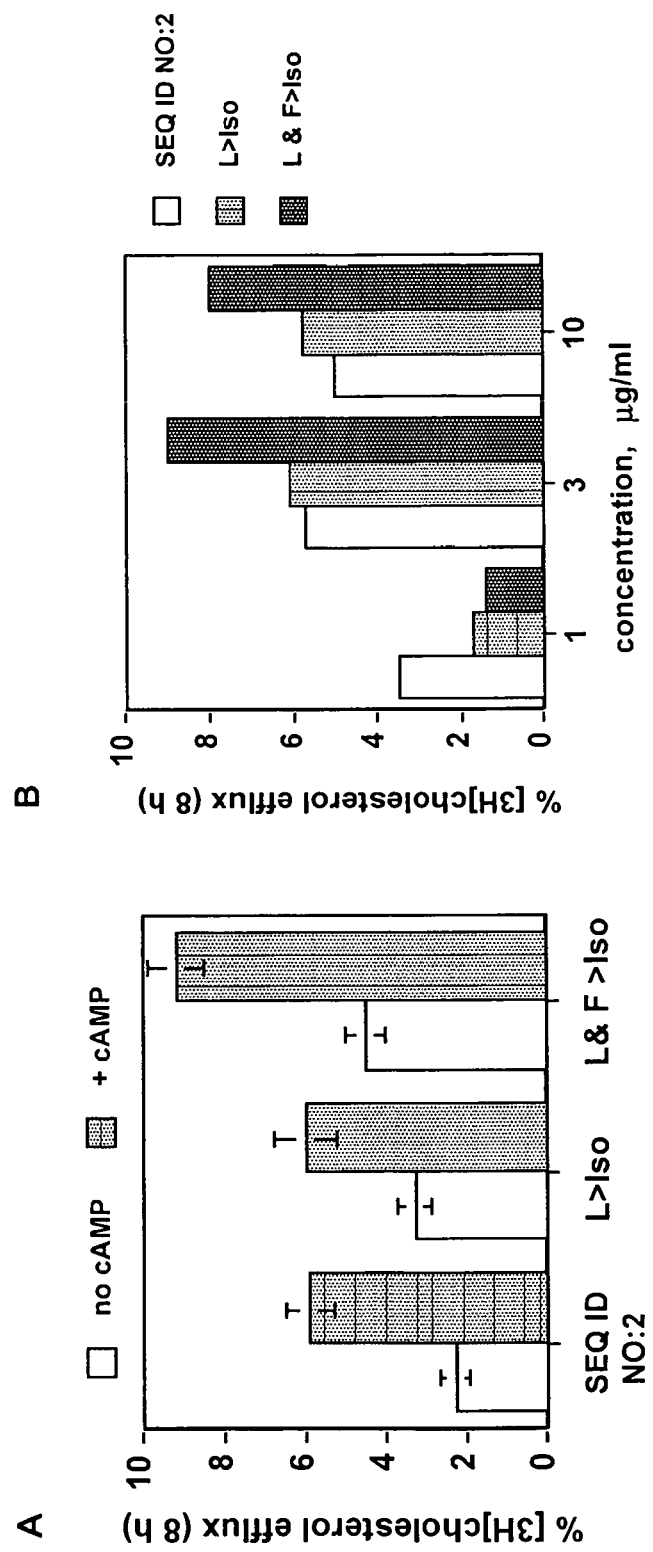
FIG. 10 provides data showing that leucine and phenylalanine residues of peptides of the invention can be replaced with isoleucine without adversely affecting ability to stimulate ABCA1 cholesterol efflux. Panel A shows the percentage of cellular [$^3$H]cholesterol that appeared in the medium in response to treatment with the indicated peptides. Panel B shows the dependence of cholesterol efflux on the concentration of peptides.

J774 cells were labelled with [³H]cholesterol as described in Example 4. Experiments were conducted by substituting hydrophobic isoleucine (I) for either all leucine (L) residues (positions 2, 6, 12, 17) or all (L) and phenylalanine (F) residues (10, 13, 16, 20) on the non-polar surface of the SEQ ID NO:2 peptide. The latter L & F>I substitutions create a peptide displaying a non-polar surface of all I residues (except W9). The results are shown in FIG. 10. Panel A shows the percentage of cellular [$^3$H]cholesterol that appeared in the medium (8 h) in response to SEQ ID NO:2 peptide versus SEQ ID NO:2 having L>I and L&F>I substitutions. Peptides were used in lipid-free form at 30 µg/ml serum-free medium. Panel B shows the dependence of cholesterol efflux on the concentration of SEQ ID NO:2 peptides with and without isoleucine substitutions, as indicated in legend; cAMP treated cells were used.

Example 12

This examples demonstrates that positively charged arginine can substitute for positively charged lysine in peptides without adversely affecting ability to stimulate ABCA1 cholesterol efflux.

Figure 11:
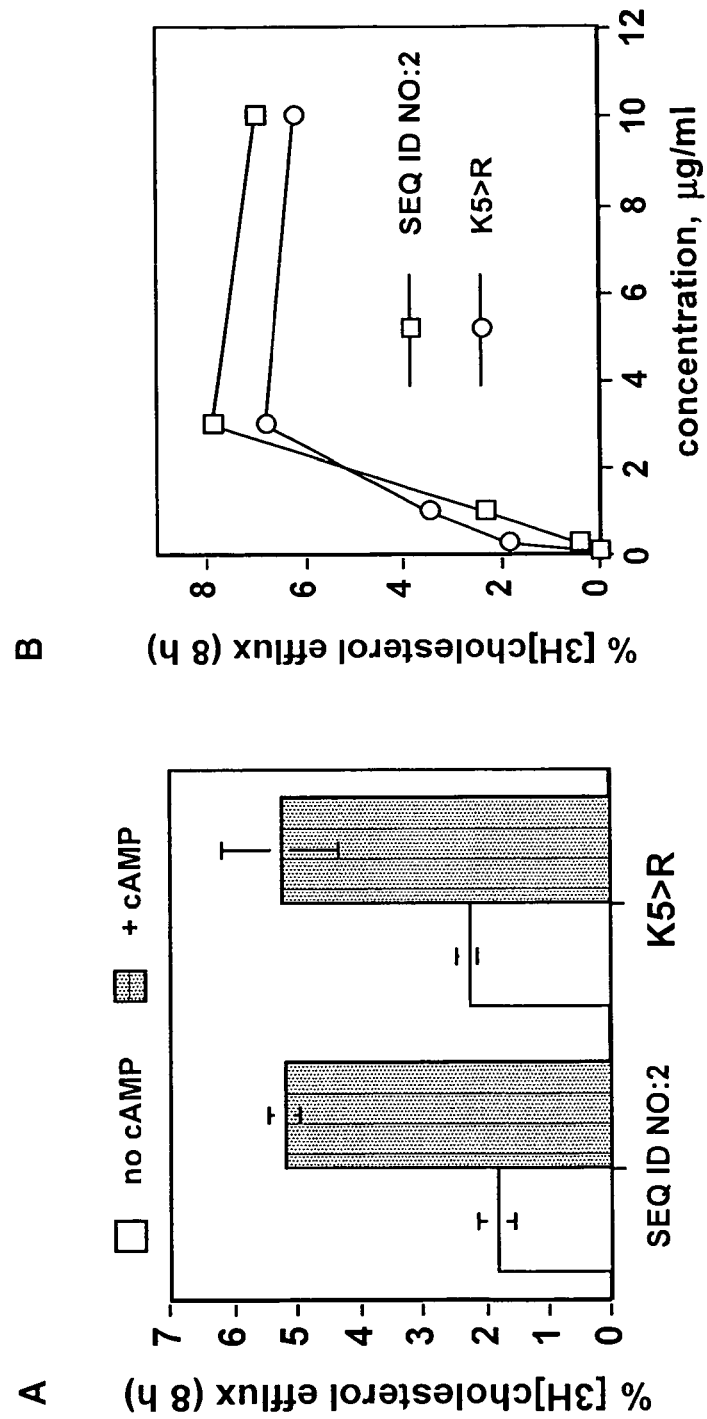
FIG. 11 provides data showing that positively charged arginine can substitute for positively charged lysine in peptides without adversely affecting ability to stimulate ABCA1 cholesterol efflux. Panel A shows the percentage of cellular [$^3$H]cholesterol that appeared in the medium in response to treatment with the indicated peptides. Panel B shows the dependence of cholesterol efflux on the concentration of peptides.

J774 cells were labeled with [$^3$H]cholesterol as described in Example 4. Experiments were conducted by substituting arginine (R) for lysine (K) at position 5 on the polar surface of the SEQ ID NO:2 peptide. The results are shown in FIG. 11. Panel A shows the percentage of cellular [$^3$H]cholesterol that appeared in the medium (8 h) in response to SEQ ID NO:2 peptide versus SEQ ID NO:2 having K5>R substitution. Peptides were used in lipid-free form at 30 µg/ml serum-free medium Panel B shows the dependence of cholesterol efflux on the concentration of SEQ ID NO:2 peptides, with and without K5>R substitution; cAMP treated cells were used.

Example 13

This example demonstrates that negatively charged aspartic acid can substitute for negatively charged glutamic acid in present peptides without adversely affecting ability to stimulate ABCA1 cholesterol efflux.

Figure 12:
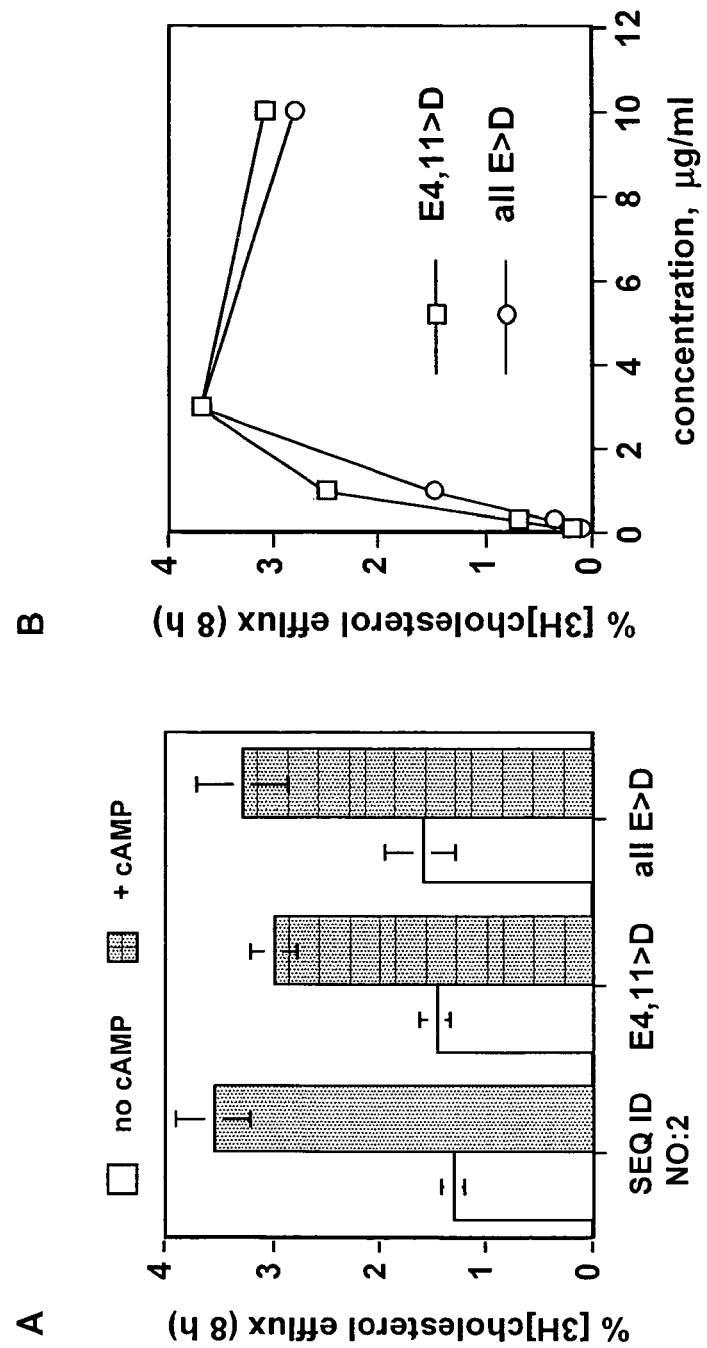
FIG. 12 provides data showing that negatively charged aspartic acid can substitute for negatively charged glutamic acid without adversely affecting ability to stimulate ABCA1 cholesterol efflux. Panel A shows the percentage of cellular [$^3$H]cholesterol that appeared in the medium in response to treatment with the indicated peptides. Panel B shows the dependence of cholesterol efflux on the concentration of peptides.

J774 cells were labeled with [$^3$H]cholesterol as described in Example 4. Experiments were conducted by substituting aspartic acid (D) for glutamic acid (E) at either positions 4,11 or positions 4,11 plus 1, 7, 15, 18 on the polar surface of the SEQ ID NO:2 peptide. The latter creates a peptide whereby all acidic residues are D; contrasting SEQ ID NO:2 where all acidic residues are E. The results are shown in FIG. 12. Panel A shows the percentage of cellular [$^3$H]cholesterol that appeared in the medium (8 h) in response to SEQ ID NO:2 peptide versus SEQ ID NO:2 having E>D substitutions. Peptides were used in lipid-free form at 30 µg/ml serum-free medium. Panel B shows the dependence of cholesterol efflux on the concentration of SEQ ID NO:2 peptides having E>D substitutions; cAMP treated cells were used.

Example 14

This example demonstrates that aspartic and glutamic acid residues are interchangeable in peptides and either can be used in combinations with other amino acid amino acid substitutions.

Figure 13:
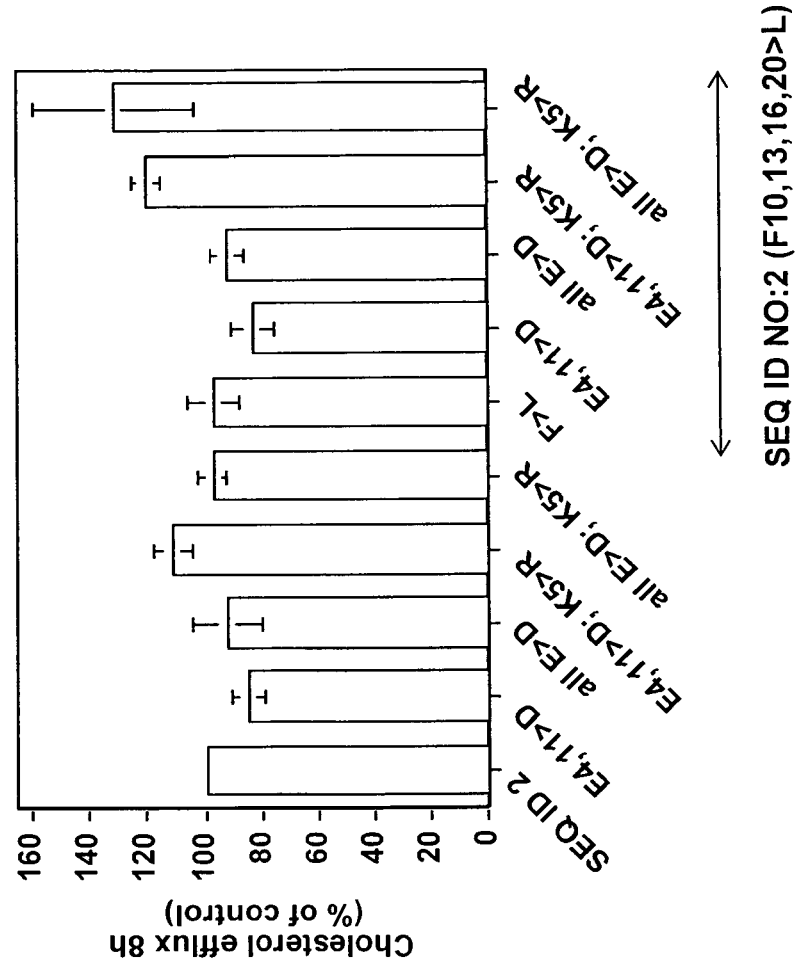
FIG. 13 provides data showing that aspartic and glutamic acid residues are interchangeable in peptides described herein and that either can be used in combinations with other amino acid substitutions. Results are expressed as a percentage of control activity (8 h) obtained using SEQ ID NO:2 peptide.

J774 cells were labelled with [$^3$H]cholesterol as described in Example 4. Experiments were conducted by substituting aspartic acid (D) for glutamic acid (E) at positions 4,11 or positions 4,11 plus 1, 7, 15, 18 on the polar surface of the SEQ ID NO:2 peptide or the SEQ ID NO:2 peptide having various other substitutions, such as K5>R and all leucine residues (i.e. F10, 13, 16, 20>L). The results are presented in FIG. 13. Peptides were used in lipid-free form at 30 µg/ml serum-free medium. Data from cAMP treated cells are shown. Results are expressed as a percentage of control activity (8 h) obtained using SEQ ID NO:2 peptide.

Example 15

This example demonstrates that tryptophan (W) or phenylalanine (F) can substitute for leucine (L) at position 12 without adversely affecting ability of peptides to stimulate ABCA1 cholesterol efflux.

Figure 14:
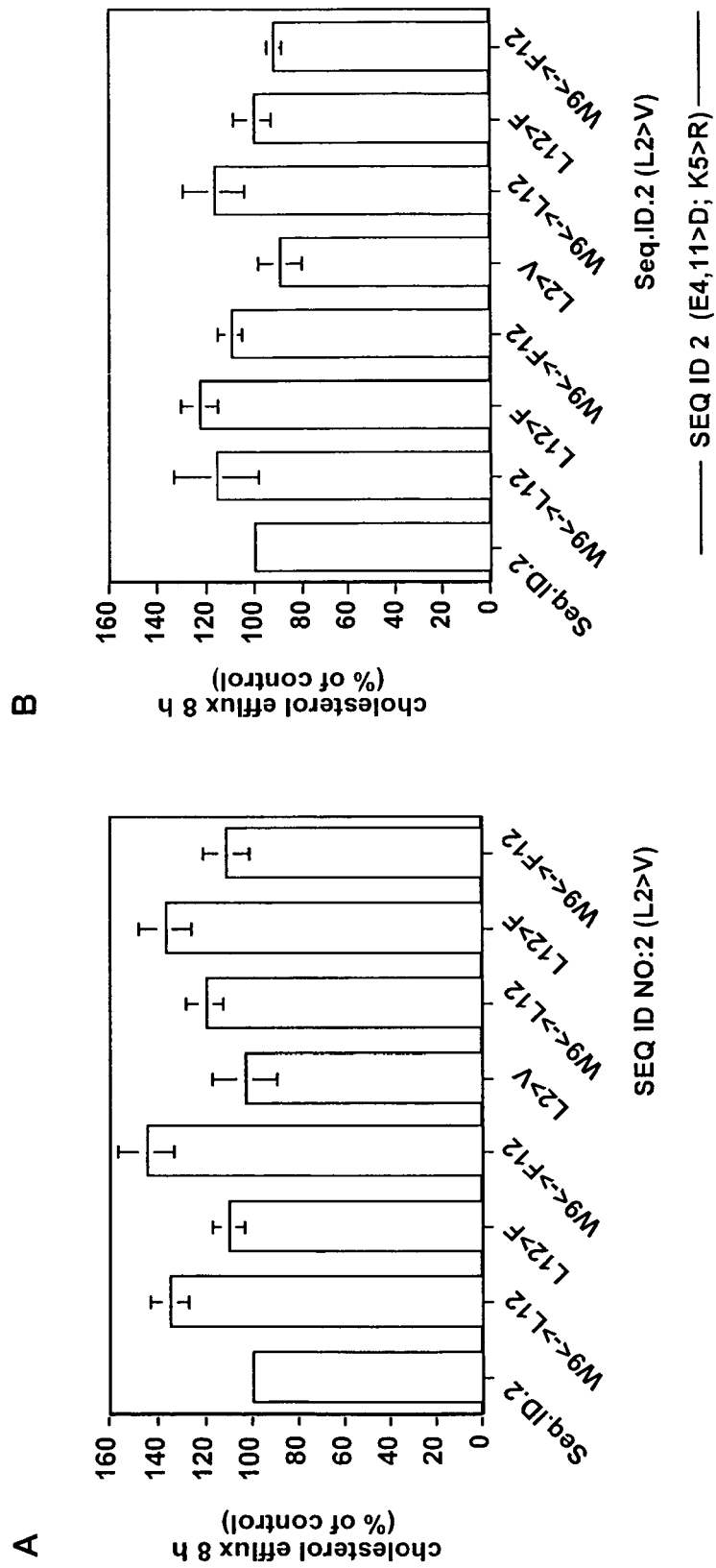
FIG. 14 provides data showing that tryptophan (W) or phenylalanine (F) can substitute for leucine (L) at position 12 without adversely affecting ability of peptides to stimulate ABCA 1 cholesterol efflux. Panels A and B show percentage of cellular [$^3$H]cholesterol that appeared in the medium in response to treatment with the indicated peptides.

J774 cells were labelled with [$^3$H]cholesterol as described in Example 4. Experiments were conducted by either exchanging positions of W9 and L12 (W9<->L12 swapping) in SEQ ID NO:2 peptide or by substituting phenylalanine (F) for leucine (L) at position 12 (L12>F) in SEQ ID NO:2 peptide or by taking the corresponding L12>F peptide and exchanging residues F12 with W9 (i.e. W9<->F12 swapping). The indicated amino acid substitutions in SEQ ID NO:2 peptide were also engineered into SEQ ID NO:2 peptide containing L2>V substitution, as described in Example 7. The results are shown in FIG. 14. Panel A shows percentage of cellular [$^3$H]cholesterol that appeared in the medium (8 h) in response to SEQ ID NO:2 peptide versus SEQ ID NO:2 peptides with indicated amino acid substitutions. Panel B shows an experiment similar to that performed for panel A, except all SEQ ID NO:2-based peptides were constructed with E4,11>D and K5>R substitutions. Peptides (Panels A and B) were used in lipid-free form at 30 µg/ml serum-free medium. Data from cAMP treated cells are shown. Results are expressed as a percentage of control activity obtained using SEQ ID NO:2 peptide.

Example 16

This example demonstrates that peptides of the present invention can be used with all D-amino acids or the reverse sequence without adversely affecting ability to stimulate ABCA 1 cholesterol efflux.

Figure 15:
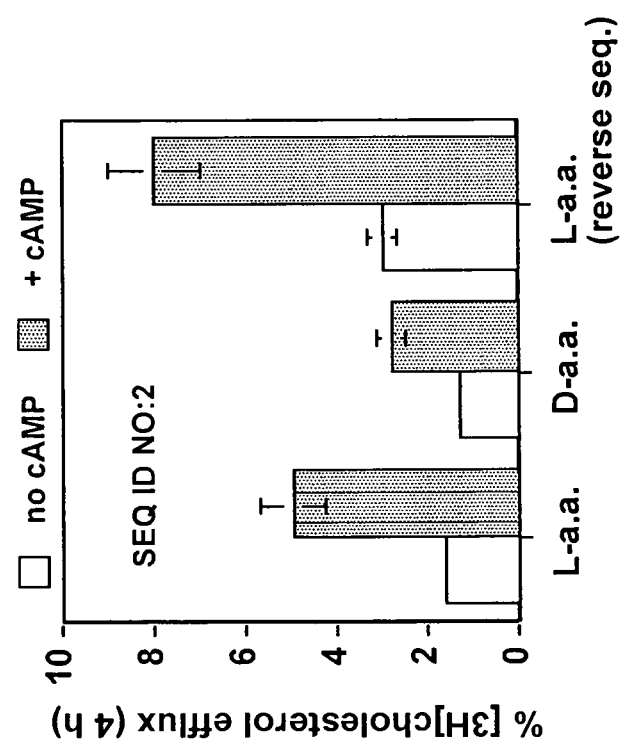
FIG. 15 provides data showing that peptides of the invention can be used with all D-amino acids or the reverse sequence without adversely affecting ability to stimulate ABCA1 cholesterol efflux.

J774 cells were labelled with [$^3$H]cholesterol as described in Example 4. Experiments were conducted using the SEQ ID NO:2 peptide composed of either all D-amino acids or by reversing primary amino acid sequence. The results are shown in FIG. 15. FIG. 15 shows the percentage of cellular [$^3$H]cholesterol that appeared in the medium (8 h) in response to the control SEQ ID NO:2 peptide (L-amino acids) versus SEQ ID NO:2 composed of D-amino acids and the reverse sequence peptidomimetic (L-amino acids). Peptides were used in lipid-free form at 30 µg/ml serum-free medium.

Example 17

Figure 16:
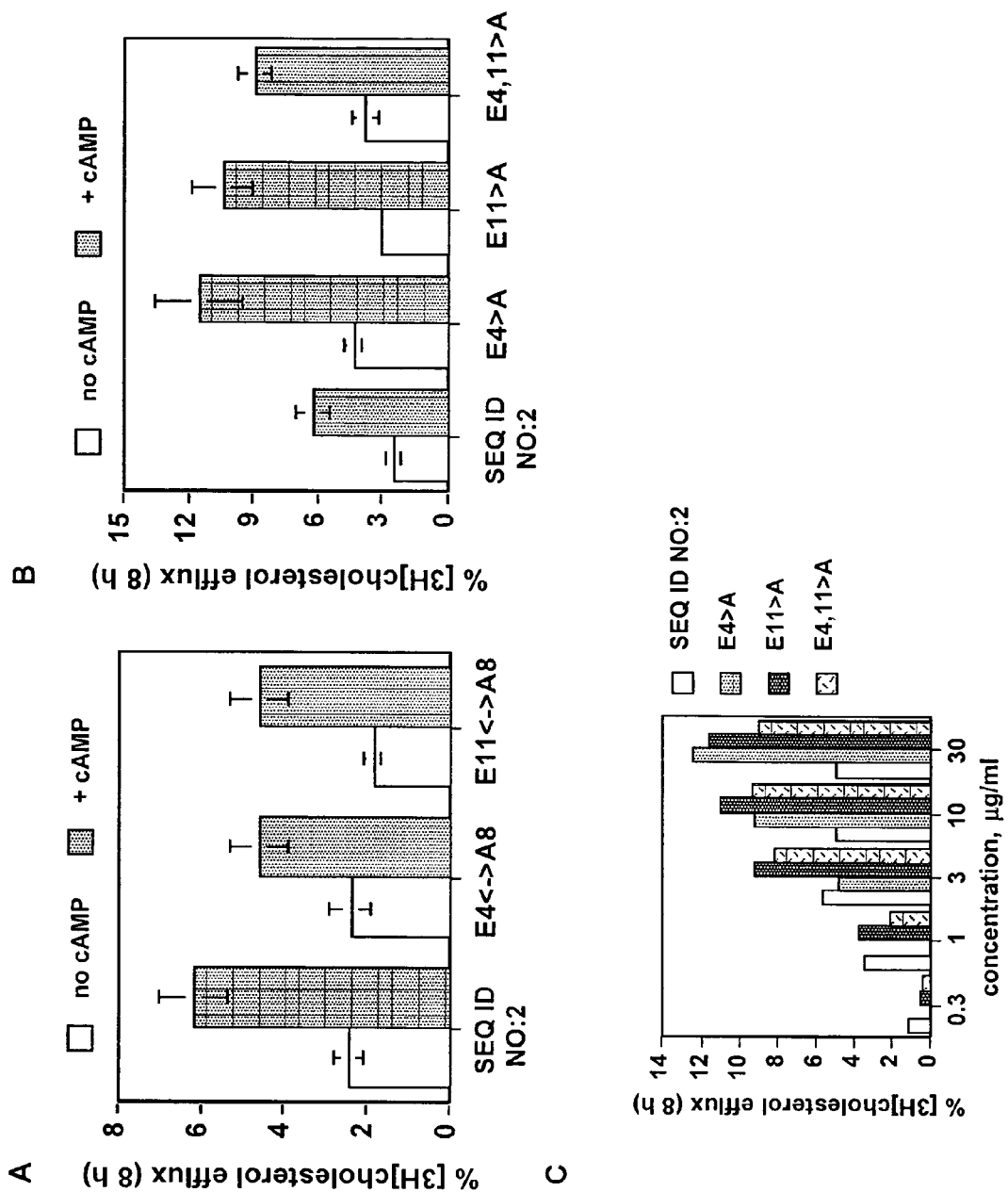
FIG. 16 provides data showing that alanine substitutions on the polar surface favorably increase ability of peptides of the present invention to stimulate ABCA1 cholesterol efflux. Panels A and B show the percentage of cellular [$^3$H]cholesterol that appeared in the medium in response to treatment with the indicated peptides. Panel C shows the dependence of cholesterol efflux on the concentration of peptides.

This examples demonstrates that alanine substitutions on the polar surface favorably increase ability of peptides of the present invention to stimulate ABCA1 cholesterol efflux J774 cells were labelled with [$^3$H]cholesterol as described in Example 4. Experiments were conducted by either exchanging positions of E4 and E 11 with A8 (E<->A swapping) or by substituting alanine (A) for glutamic acid (E) at positions 4 and 11. The results are shown in FIG. 16. Panel A shows the percentage of cellular [$^3$H]cholesterol that appeared in the medium (8 h) in response to SEQ ID NO:2 peptide versus SEQ ID NO:2 with E< >A exchanges. Both exchanges (E4< >A8 and E11< >A8) decreased efflux activity of the SEQ ID NO:2 peptide, indicating A at position 8 has importance for activity. Panel B shows the results of an experiment similar to that for panel A, except SEQ ID NO:2 peptides with E>A substitutions were used. Peptides (Panels A and B) were used in lipid-free form at 30 µg/ml serum-free medium Panel C shows the dependence of cholesterol efflux on concentration of SEQ ID NO:2 peptide and SEQ ID NO:2 peptides with increasing numbers of E>A substitutions on polar surface. The alanine substitutions (panels B and C) greatly increased the ability of SEQ ID NO:2 peptide to stimulate ABCA1 cholesterol efflux efficiently. This contrasts the poor outcome (decreasing efflux activity) when alanine substitutions are engineered into the non-polar surface of the peptides (FIG. 7).

Example 18

This example demonstrates that alanine can substitute for arginine 14 (R14) and glutamic acid 18 (E18) without adversely affecting ability to stimulate ABCA1 cholesterol efflux.

Figure 17:
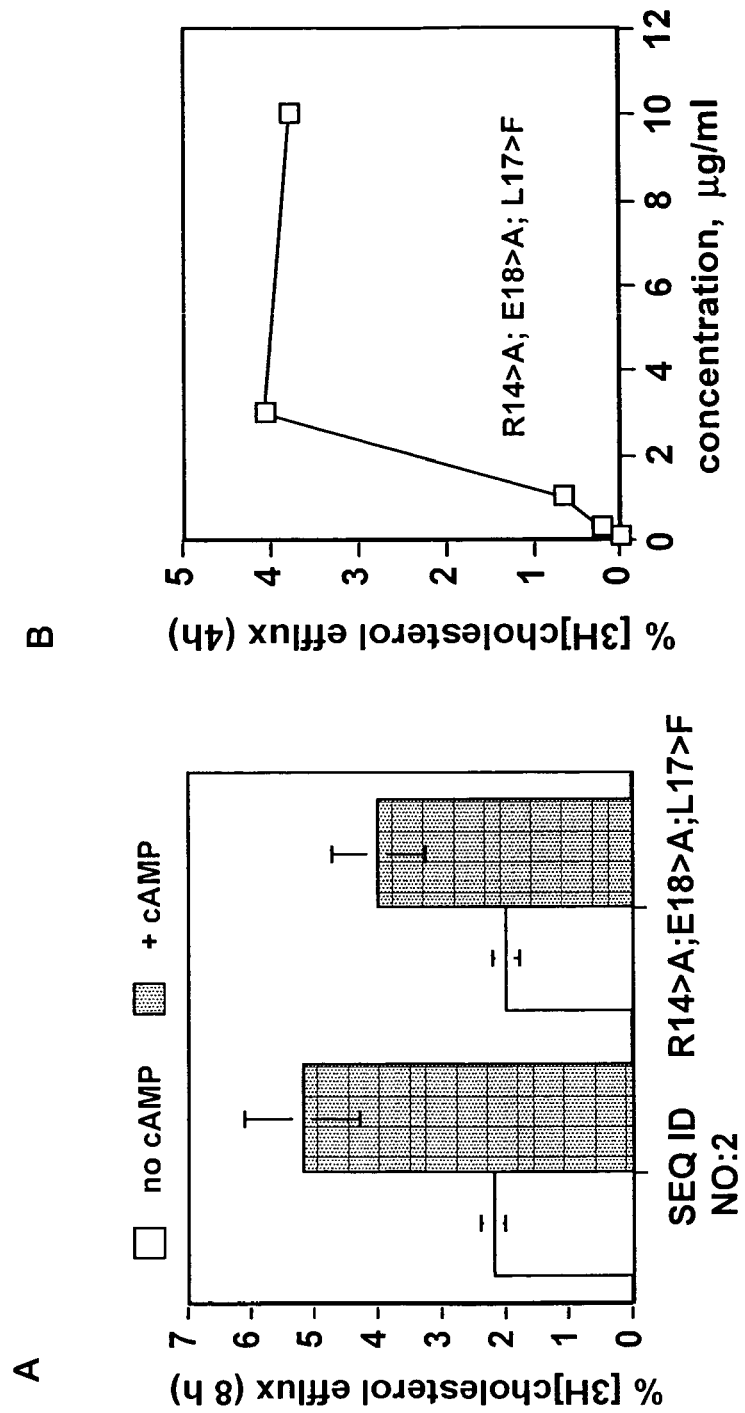
FIG. 17 provides data showing that alanine can substitute for arginine 14 (R14) and glutamic acid 18 (E18) without adversely affecting ability to stimulate ABCA1 cholesterol efflux. Panel A shows the percentage of cellular [$^3$H]cholesterol that appeared in the medium in response to treatment with the indicated peptides. Panel B shows the dependence of cholesterol efflux on the concentration of peptides.

J774 cells were labelled with [$^3$H]cholesterol as described in Example 4. Experiments were conducted by substituting alanine (A) for arginine and glutamic acid at positions 14 and 18, respectively, which represent a putative salt-bridge pair. Substitutions were engineered into a SEQ ID NO:2 peptide with the conservative L17>F substitution. The results are shown in FIG. 17. Panel A shows percentage of cellular [$^3$H]cholesterol that appeared in the medium (8 h) in response to peptides. Peptides were used in lipid-free form at 30 µg/ml serum-free medium. Panel B shows the dependence of cholesterol efflux on concentration of SEQ ID NO:2 peptide with alanine substitutions (as indicated). The peptide stimulated cholesterol with high efficiency (i.e. max. efflux at 3 µg/ml) similar to the parent SEQ ID NO:2 peptide (FIGS. 3 and 4).

Example 19

This example demonstrates that peptides of the present invention, e.g., SEQ ID NO:2 and peptide comprising substitutions of SEQ ID NO:2 described herein can be formulated with phospholipids to create complexes that support high levels of cellular cholesterol efflux via ABCA1-dependent and -independent mechanisms

```
ELRDRLEAWLDLLRELLERL    (SEQ ID NO: 12)

ELREKLEAWFELFREFLERF    (SEQ ID NO: 2)
```

Figure 18:
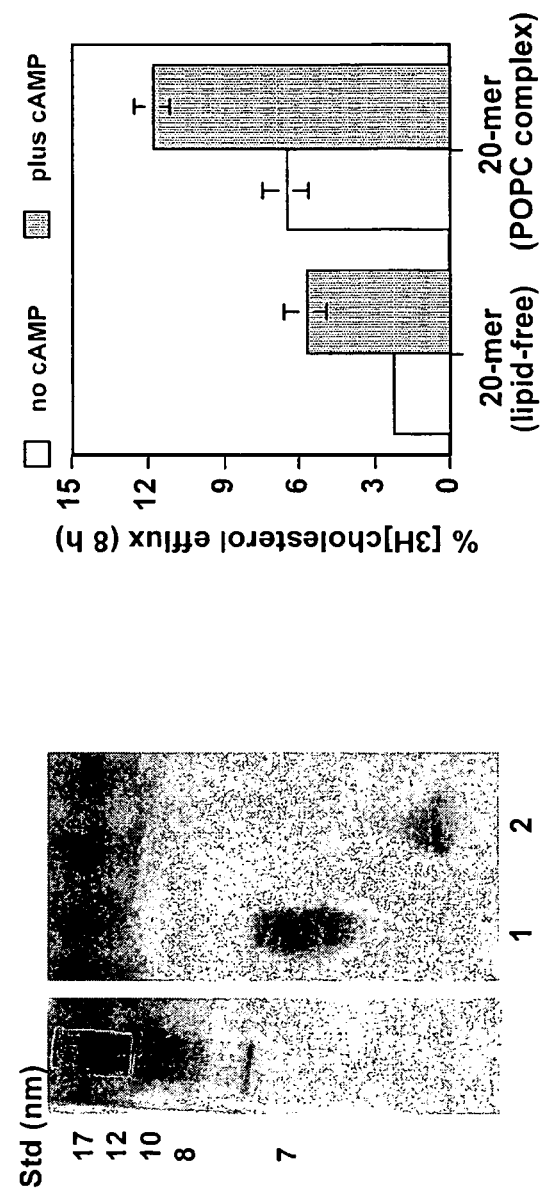
FIG. 18 provides data showing that peptides of the invention can be formulated with phospholipids to create complexes that support high levels of cellular cholesterol efflux via ABCA1-dependent and -independent mechanisms. Panel A shows a gel photograph that demonstrates the particle size of peptide:POPC complexes. Panel B shows the cholesterol efflux activity of peptide:POPC complexes.

A 20-mer peptide corresponding to SEQ ID N012 (described in Example 13) was formulated with 1-palmitoyl-2-oleoyl-phosphatidylcholine (POPC), using a modified cholate dialysis procedure. The results of an experiment evaluating cholesterol efflux are shown in FIG. 18. Panel A shows a gel photograph that demonstrates the particle size of peptide:POPC complexes determined by non-denaturing gradient (4-20%) gel electrophoresis. Lane 1 corresponds to peptide:POPC complexes and lane 2 to lipid-free peptide. Panel B shows the cholesterol efflux activity of peptide:POPC complexes, as judged using J774 macrophages labelled with [$^3$H]cholesterol and treated with (shaded bars) and without cAMP (open bars). For comparative purposes, cholesterol efflux in response to lipid-free SEQ ID NO:12 peptide is shown. Concentration of lipid-free peptide and peptide: POPC complexes were 50 µg/ml (based on peptide mass). Values are means±SD, n=3.

Example 20

This example demonstrates that peptides of the present invention, as exemplified by SEQ ID NO:12 in this example, reduced established atherosclerosis in apolipoprotein E-deficient mice fed high-fat western-diet.

Figure 19:
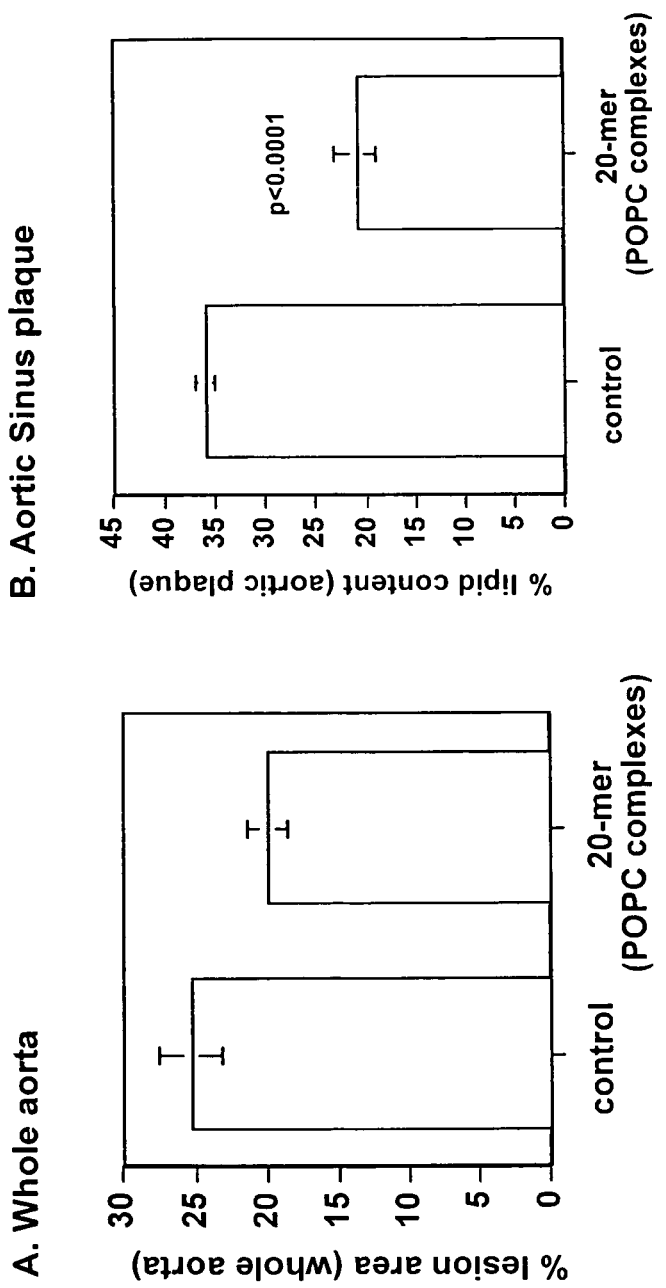
FIG. 19 provides data showing that peptides of the invention reduced established atherosclerosis in apolipoprotein E-deficient mice fed high-fat western-diet. Panel A shows the extent of atherosclerosis in control and peptide-treated mice, expressed as percentage of aorta covered with lesions. Panel B shows the lipid-content of aortic sinus plaque, determined by Oil Red O staining.

Male apolipoproteinE deficient (apoE−/−) mice at seven weeks of age were fed a high-fat western diet for a total of 26 weeks. During the last 6 weeks on the high fat diet, the mice received intraperitoneal (ip) injections every other day of either saline (control) or the SEQ ID NO:12 peptide formulated with POPC. The dose of peptide:POPC was 30 mg/kg BW, based on peptide mass. The results are shown in FIG. 19. Panel A provides data showing the extent of atherosclerosis in control and peptide-treated mice, expressed as percentage of aorta covered with lesions. Panel B shows the lipid-content of aortic sinus plaque, determined by Oil Red O staining. Values are means±SEM, n=7 mice per group in both panels.

Example 21

This examples demonstrates use of amino acid substitutions to confer resistance to myeloperoxidase (MPO)-derived oxidation products.

Figure 20:
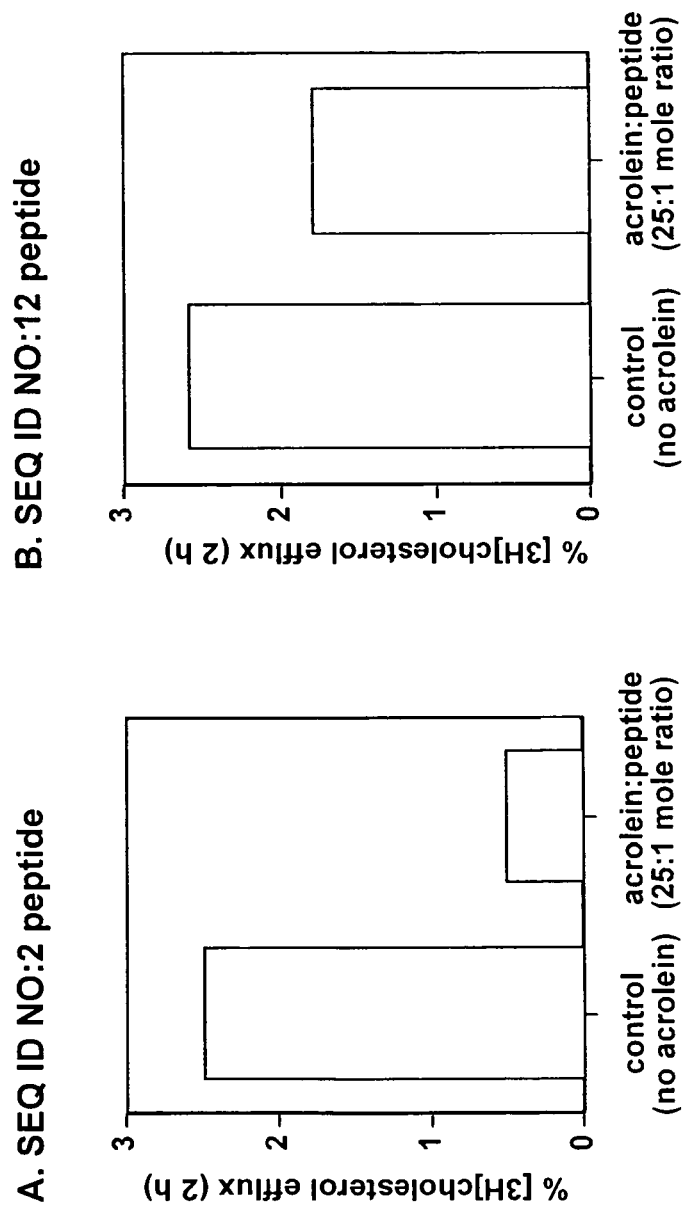
FIG. 20 provides data showing use of amino acid substitutions to confer resistance to myeloperoxidase (MPO)-derived oxidation products. Panel A shows the cholesterol efflux activity of the SEQ ID NO:2 peptide incubated with and without acrolein. Panel B shows the cholesterol efflux activity of the SEQ ID NO:12 peptide.

Peptides corresponding to SEQ ID NO:2 and SEQ ID NO:12 were exposed to acrolein (acrolein:peptide mole ratio=25:1) for 18 h at 37° C. Control peptides were similarly incubated in the absence of acrolein. Control and acrolein-treated peptides were then dialyzed and used for cholesterol efflux experiments. The results of this experiment are shown in FIG. 20. Panel A shows the cholesterol efflux activity of the SEQ ID NO:2 peptide incubated with and without acrolein. Acrolein greatly decreased the activity of the SEQ ID NO:2 peptide. Panel B shows the cholesterol efflux activity of the SEQ ID NO:12 peptide, showing modest effects of acrolein. J774 macrophages treated with cAMP, which up-regulates ABCA1, were used in both panels. Cholesterol efflux assays were conducted using peptides at 2 µg/ml serum free-medium.

Example 22

Peptides of the invention induce preβ-1 HDL formation in human plasma via a highly specific mechanism involving distinct HDL subpopulations.

Figure 21:
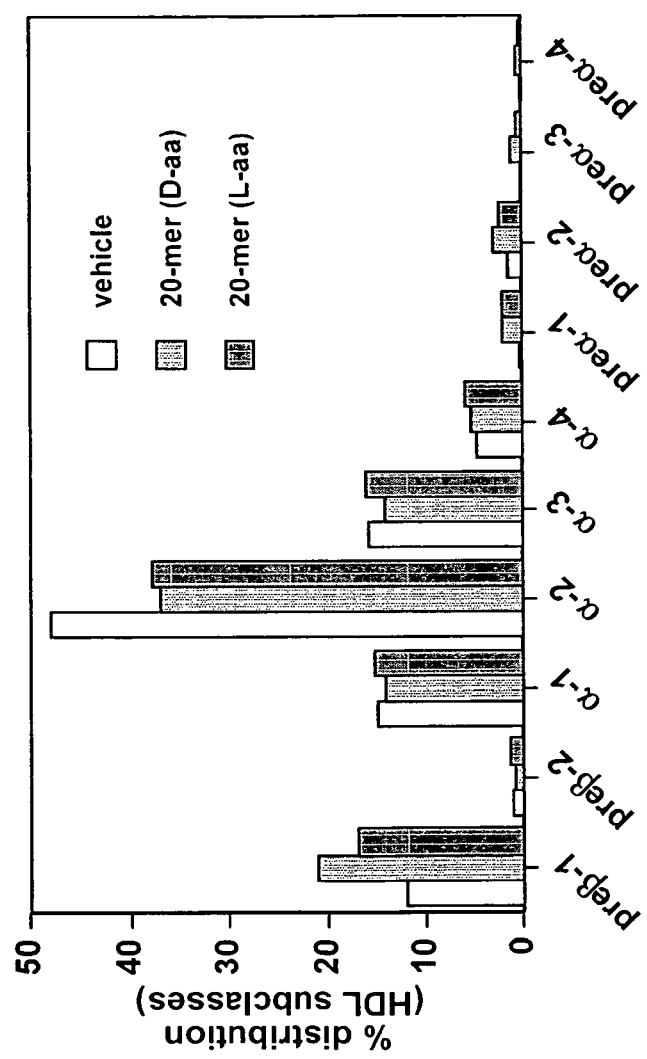
FIG. 21 provides data showing that peptides of the invention induced preβ-1 HDL formation in human plasma via a highly specific mechanism involving distinct HDL subpopulations.

Peptides corresponding to SEQ ID NO:2 were added to human plasma at a final concentration of 30 µg/ml (i.e. peptide:apoA-I mole ratio ~1:5). Plasma with and without peptide were subsequently incubated for 5 minutes at 37° C. Following incubations, samples of plasma were subjected to agarose gel electrophoresis in the first dimension followed by native gradient gel electrophoresis in the second dimension. Proteins on resulting gels were transferred to nitrocellulose and analyzed by Western-blot analysis using an apoA-I antibody. The results are shown in FIG. 21. The distribution of HDL subpopulations in plasma treated with vehicle alone (open bars), SEQ ID NO:2 peptide composed of all D-amino acids (intermediate shade), and SEQ ID NO:2 peptide composed of all L-amino acids (darkly shaded) is shown. Peptide treatment produced preferential increase in preβ-1 HDL. Reductions of α-HDL subpopulations indicate that peptides specifically interact with distinct HDL species to generate preβ-1 apoA-I particles.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An isolated polypeptide comprising a sequence of 20 amino acids in length that has at least 65% identity to SEQ ID NO:12, wherein the polypeptide has cholesterol efflux activity.

2. The isolated polypeptide of claim 1, wherein the sequence of 20 amino acids in length has at least 75% identity to SEQ ID NO:12.

3. The isolated polypeptide of claim 1, wherein the polypeptide further comprises a protecting group.

4. The isolated polypeptide of claim 3, wherein the protecting group is selected from the group consisting of acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl—Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-butyl (tBu), and trifluoroacetyl (TFA).

5. The isolated polypeptide of claim 3, wherein the protecting group is coupled to the amino or carboxy terminus.

6. The isolated polypeptide of claim 1, wherein the polypeptide comprises a first protecting group coupled to the amino terminus and a second protecting group coupled to the carboxyl terminus.

7. The isolated polypeptide of claim 6, wherein said first protecting group is selected from the group consisting of acetyl, propionyl, and a 3 to 20 carbon alkyl.

8. The isolated polypeptide of claim 7, wherein the first protecting group is an acetyl.

9. The isolated polypeptide of claim 8, wherein said second protecting group is an amide.

10. The isolated polypeptide of claim 1, wherein the polypeptide comprises at least one "D" amino acid.

11. The isolated polypeptide of claim 1, wherein all enantiomeric amino acids are "D" amino acids.

12. A composition comprising a polypeptide of claim 1 and a pharmaceutically acceptable carrier.

13. A composition comprising a polypeptide of claim 1 complexed with lipid.

14. The composition of claim 13, wherein said lipid is a phospholipid.

15. The composition of claim 14, wherein the phospholipid is 1-palmitoyl-2-oleoyl-sn-glycerol-3-phosphatidylcholine ("POPC").

16. The composition of claim 13, further comprising a pharmaceutically acceptable carrier.

17. A method for mediating cholesterol efflux in a mammal, said method comprising administering to said mammal the polypeptide of claim 1.

18. A method for treating a symptom of atherosclerosis in a mammal, said method comprising administering to said mammal a therapeutically effective amount of the polypeptide of claim 1.

19. A method for stabilizing a vulnerable plaque in a lumen wall of a mammal, said method comprising administering to said mammal the polypeptide of claim 1.

* * * * *